US010159670B2

(12) United States Patent
Hornstein et al.

(10) Patent No.: US 10,159,670 B2
(45) Date of Patent: Dec. 25, 2018

(54) METHODS OF DIAGNOSING AND TREATING MOTOR NEURON DISEASES AND OTHER CELLULAR STRESS-RELATED DISEASES

(71) Applicant: Yeda Research and Development Co. Ltd., Rehovot (IL)

(72) Inventors: Eran Hornstein, Rehovot (IL); Anna Maria Emde, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 28 days.

(21) Appl. No.: 14/612,034

(22) Filed: Feb. 2, 2015

(65) Prior Publication Data

US 2015/0164891 A1 Jun. 18, 2015

Related U.S. Application Data

(63) Continuation-in-part of application No. PCT/IL2013/050655, filed on Jul. 31, 2013.

(60) Provisional application No. 61/677,494, filed on Jul. 31, 2012.

(51) Int. Cl.
*A61K 31/496* (2006.01)
*A61K 31/538* (2006.01)
*A61K 45/06* (2006.01)

(52) U.S. Cl.
CPC .......... *A61K 31/496* (2013.01); *A61K 31/538* (2013.01); *A61K 45/06* (2013.01)

(58) Field of Classification Search
CPC ..... A61K 31/496; A61K 31/538; A61K 45/06
See application file for complete search history.

(56) References Cited

U.S. PATENT DOCUMENTS

| | | | |
|---|---|---|---|
| 6,756,369 B2 | 6/2004 | Mitchell et al. | |
| 2006/0247193 A1 | 11/2006 | Taira et al. | |
| 2007/0197548 A1* | 8/2007 | Murthy | A61K 9/0019 514/253.08 |
| 2008/0176766 A1 | 7/2008 | Brown et al. | |
| 2009/0246136 A1 | 10/2009 | Williams et al. | |
| 2012/0071539 A1 | 3/2012 | Jin | |
| 2014/0038927 A1* | 2/2014 | Cohen | A61K 31/137 514/171 |
| 2014/0080780 A1 | 3/2014 | Wolozin | |
| 2014/0348857 A1 | 11/2014 | Chang et al. | |

FOREIGN PATENT DOCUMENTS

| | | |
|---|---|---|
| CN | 1475215 | 2/2004 |
| CN | 101390854 | 3/2009 |
| JP | 2003-514858 | 4/2003 |
| WO | WO 2010/064248 | 6/2010 |
| WO | WO 2014/020608 | 2/2014 |

OTHER PUBLICATIONS

Kurzynska-Kokorniak et al. Nucleic Acids Research, 2015.*
Huang (Cell, Mar. 12, 2012, p. 933-946). (Year: 2012).*
International Preliminary Report on Patentability dated Feb. 12, 2015 From the International Bureau of WIPO Re. Application No. PCT/IL2013/050655.
International Search Report and the Written Opinion dated Oct. 8, 2013 From the International Searching Authority Re. Application No. PCT/IL2013/050655.
Buchan et al. "Eukaryotic Stress Granules Are Cleared by Autophagy and Cdc48/VCP Function", Cell, 153(7): 1461-1474, Jun. 20, 2013.
Buratti et al. "Nuclear Factor TDP-43 Can Affect Selected MicroRNA", The FEBS Journal, 277: 2268-2281, 2010.
Buratti et al. "The Multiple Roles of TDP-43 in Pre-mRNA Processing and Gene Expression Regulation", RNA Biology, 7(4): 420-429, Published Online Jul. 1, 2010.
Chen et al. "A Universal Activator of MicroRNAs Identified From Photoreaction Products", Chemical Communications, 48: 6432-6434, 2012.
Deiters "Small Molecule Modifiers of the MicroRNA and RNA Interference Pathway", The AAPS Journal, 12(1): 51-60, Mar. 2010.
Emde et al. "MiRNAs at the Interface of Cellular Stress and Disease", The EMBO Journal, 33(13): 1428-37, Epub May 27, 2014.
Gascon et al. "Cause or Effect: Misregulation of MicroRNA Pathways in Neurodegeneration", Frontiers in Neuroscience, XP055081041, 6: 1-10, Apr. 9, 2010. Abstract, "ALS and FTD", p. 5, l-h Col.—r-h Col., p. 5, r-h Col., line 3-23.
Kawahara et al. "TDP-43 Promotes MicroRNA Biogenesis as A Component of the Drosha and Dicer Complexes", Proc. Natl. Acad. Sci. USA, PNAS, XP055081044, 109(9): 3347-3352, Feb. 9, 2012.
Kim et al. "Mutations in Prion-Like Domains in HnRNPA2B1 and HnRNPA1 Cause Multisystem Proteinopathy and ALS", Nature, 495(7442): 467-473, Epub Mar. 3, 2013.
Melo et al. "Small Molecule Enoxacin Is A Cancer-Specific Growth Inhibitor That Acts by Enhancing TAR RNA-Binding Protein 2-Mediated MicroRNA Processing", Proc. Natl. Acad. Sci. USA, PNAS, XP055081058, 108(11): 4394-4399, Mar. 15, 2011. Abstract, p. 4394, r-h Col., Para 2.
Rosen et al. "Mutations in Cu/Zn Superoxide Dismutase Gene Are Associated With Familial Amyotrophic Lateral Sclerosis", Nature, 362: 59-62, Mar. 4, 1993.
Rowland et al. "Amyotrophic Lateral Sclerosis", The New England Journal of Medicine, 344(22): 1688-1700, May 31, 2001.
Shan et al. "A Small Molecule Enhances RNA Interference and Promotes MicroRNA Processing", Nature Biotechnology, XP055081064, 26(8): 933-940, Jul. 20, 2008. Abstract, p. 933-939, Line 4.
Notification of Office Action and Search Report dated Mar. 2, 2016 From the State Intellectual Property Office of the People's Republic of China Re. Application No. 201380051051.0 and Its Translation Into English.

(Continued)

*Primary Examiner* — Umamaheswari Ramachandran

(57) ABSTRACT

A method of treating a cellular stress-related disease in a subject in need thereof is provided. The method comprising administering to the subject a therapeutically effective amount of an agent capable of enhancing processing of a pre-miRNA, thereby treating the cellular stress-related disease in the subject. Methods for treating motor neuron disease (MND) are also provided as well as pharmaceutical compositions.

2 Claims, 16 Drawing Sheets
(16 of 16 Drawing Sheet(s) Filed in Color)
Specification includes a Sequence Listing.

(56) References Cited

OTHER PUBLICATIONS

Baldwin "A New Tool for In Vivo Manipulation of Brain MicroRNA Levels: The Work of Smalheiser et al. (2014)", Frontiers in Psychiatry, 6(Art.44): 1-3, Apr. 20, 2015.
Dwivedi et al. "Chronic Corticosterone-Mediated Dysregulation of MicroRNA Network in Prefrontal Cortex of Rats: Relevance to Depression Pathophysiology", Translational Psychiatry, 5: e682-1-e682-11, Published Online Nov. 17, 2015.
Sidrauski et al. "Pharmacological Dimerization and Activation of the Exchange Factor eIF2B Antagonizes the Integrated Stress Response", eLife, 4: e07314-1-e07314-27, Apr. 15, 2015.
Smalheiser et al. "Enoxacin Elevates MicroRNA Levels in Rat Frontal Cortex and Prevents Learned Helplessness", Frontiers in Psychiatry, 5(Art.6): 1-7, Feb. 10, 2014.
Smalheiser et al. "Expression of MicroRNAs and Other Small RNAs in Prefrontal Cortex in Schizophrenia, Bipolar Disorder and Depressed Subjects", PLOS ONE, 9(1): e86469-1-e86469-12, Jan. 27, 2014.
Smalheiser et al. "MicroRNA Expression Is Down-Regulated and Reorganized in Prefrontal Cortex of Depressed Suicide Subjects", PLoS ONE, 7(3): e33201-1-e33201-11, Mar. 9, 2012.
Di Prisco et al. "Translational Control of mGluR-Dependent Long-Term Depression and Object-Place Learning by E1F2[Alpha]", Nature Neuroscience, 17(8):1073-82, Aug. 2014.
Emde et al. "Dysregulation MiRNA Biogenesis Downstream of Cellular Stress and ALS-Causing Mutations: A New Mechanism for ALS", The EMBO Journal, 34(21): 2633-2651, 2015.
Notice of Reason for Rejection dated Jan. 31, 2017 From the Japan Patent Office Re. Application No. 2015-524902. (4 Pages).
Translation of Notice of Reason for Rejection dated Jan. 31, 2017 From the Japan Patent Office Re. Application No. 2015-524902. (5 Pages).
Haramati et al. "MiRNA Malfunction Causes Spinal Motor Neuron Disease", Proc. Natl. Acad. Sci. USA, PNAS, 107(29): 13111-13116, Jul. 20, 2010.
Williams et al. "MicroRNA-206 Delays ALS Progression and Promotes Regeneration of Neuromuscular Synapses in Mice", Science, 326(5959): 1549-1554, Dec. 11, 2009.
Notification of Office Action and Search Report dated Nov. 28, 2016 From the State Intellectual Property Office of the People's Republic of China Re. Application No. 201380051051.0 and Its Translation Into English. (18 Pages).
Notification of Office Action dated Jun. 15, 2017 From the State Intellectual Property Office of the People's Republic of China Re. Application No. 201380051051.0 and Its Translation Into English. (9 Pages).
Notice of Reason for Rejection dated Oct. 3, 2017 From the Japan Patent Office Re. Application No. 2015-524902. (3 Pages).
Translation of Notice of Reason for Rejection dated Oct. 3, 2017 From the Japan Patent Office Re. Application No. 2015-524902. (6 Pages).
Communication Pursuant to Article 94(3) EPC dated Jun. 29, 2018 From the European Patent Office Re. Application No. 13756208.8. (6 Pages).
Decision on Rejection dated Feb. 12, 2018 From the State Intellectual Property Office of the People's Republic of China Re. Application No. 201380051051.0 and Its Translation Into English. (11 Pages).

\* cited by examiner

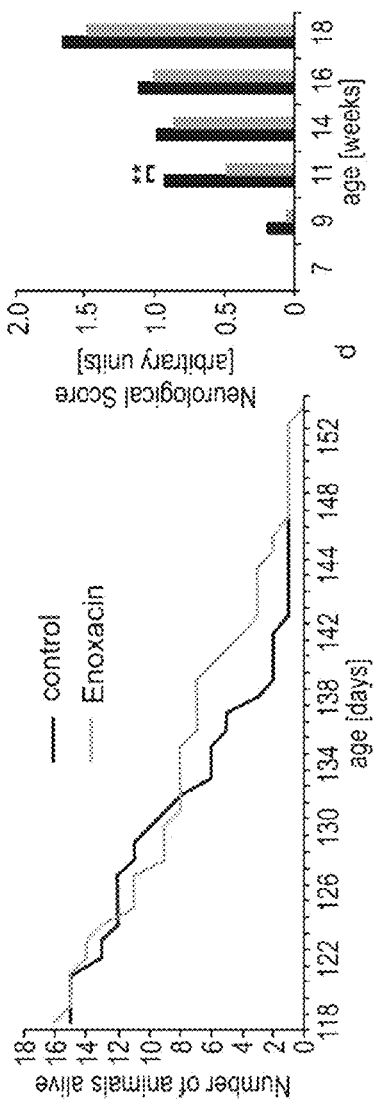
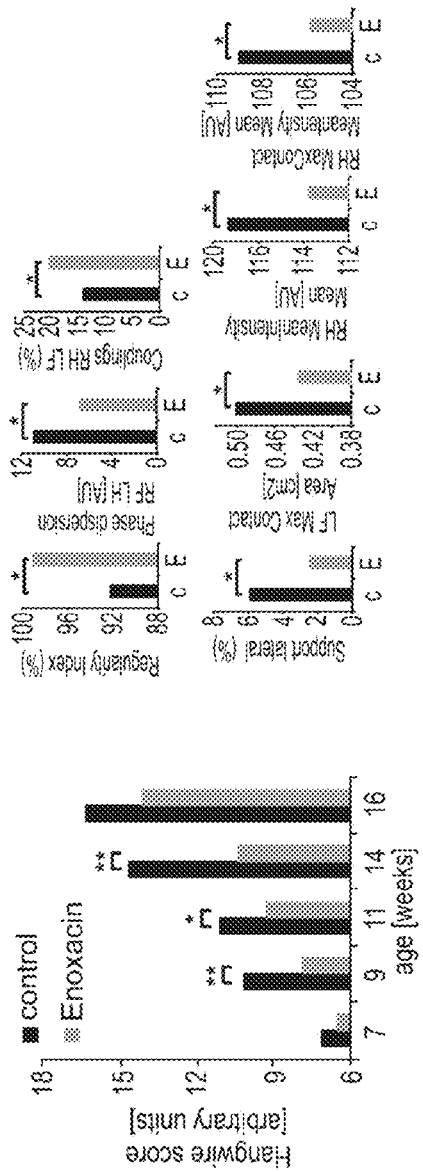
FIG. 4A
FIG. 4B
FIG. 4C
FIG. 4D

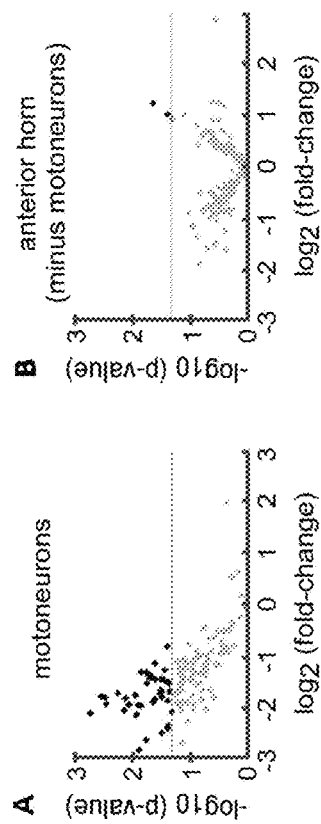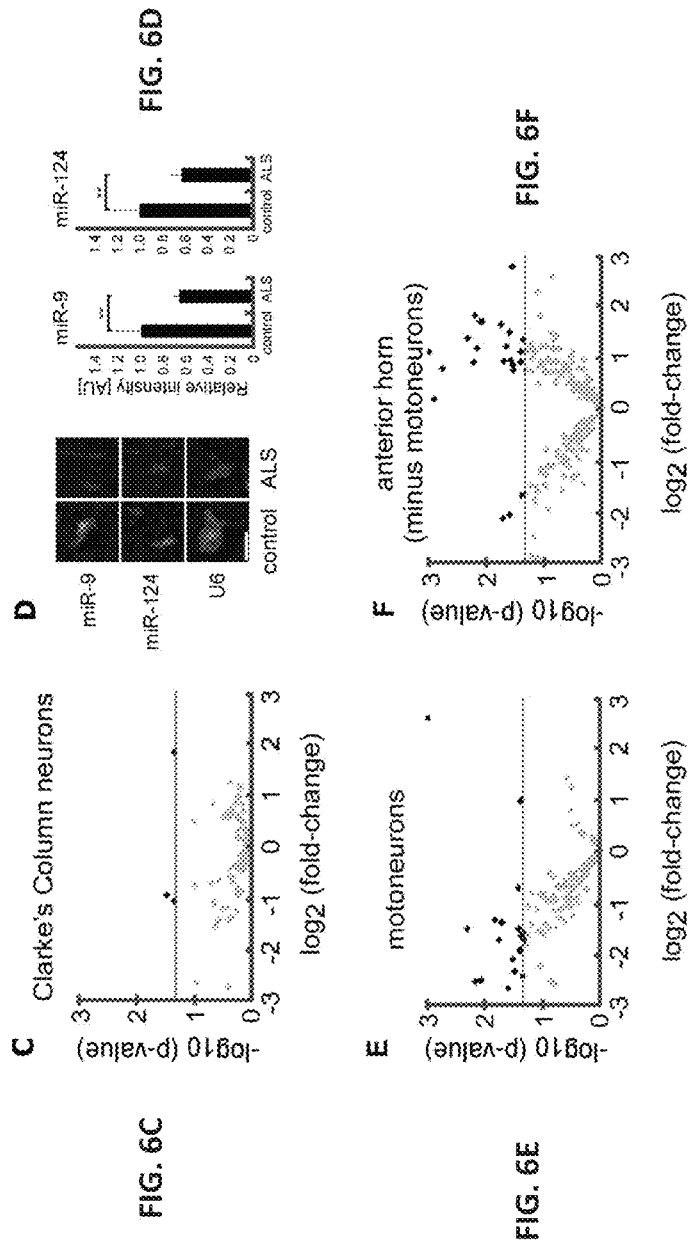
FIG. 6A FIG. 6B FIG. 6C FIG. 6D FIG. 6E FIG. 6F

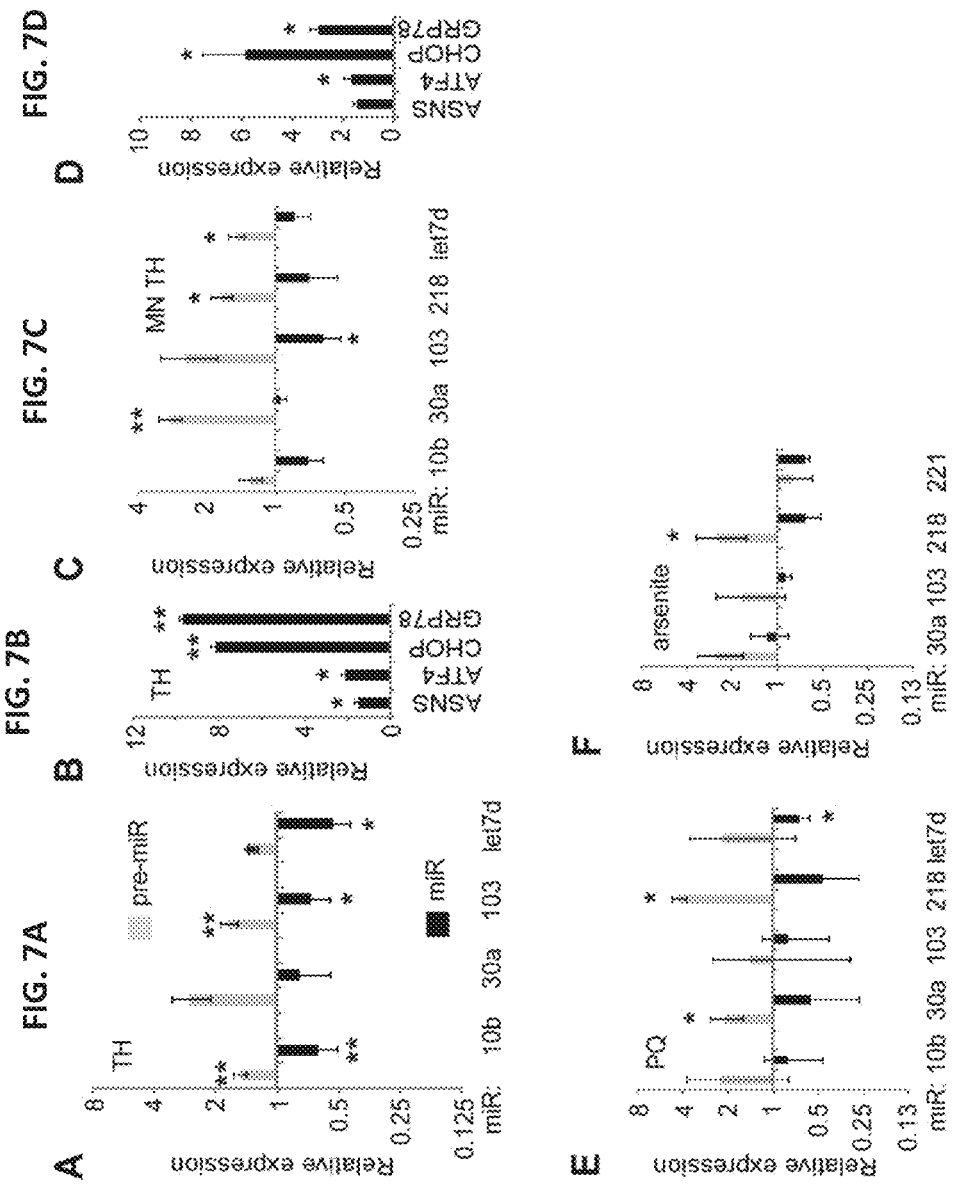

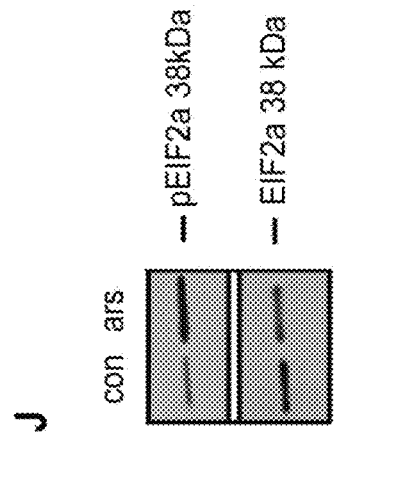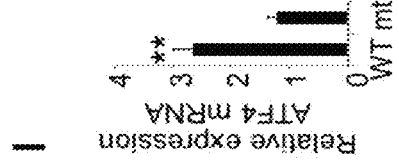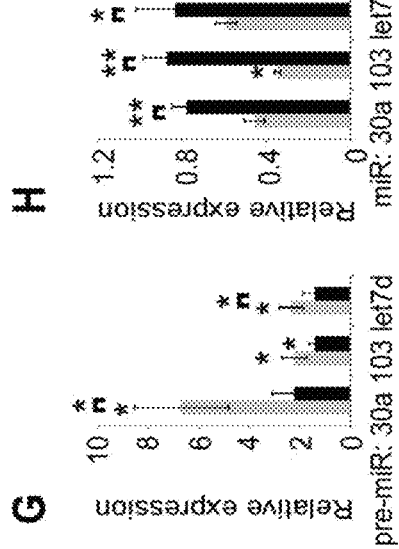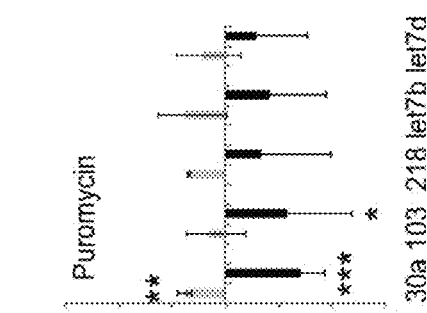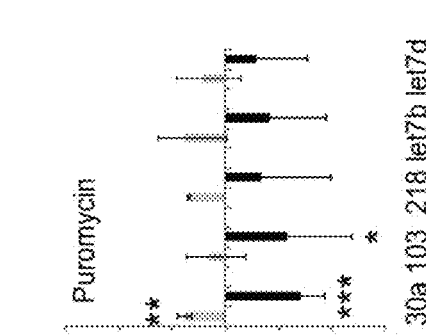
FIG. 7G FIG. 7H FIG. 7I FIG. 7J FIG. 7K FIG. 7L

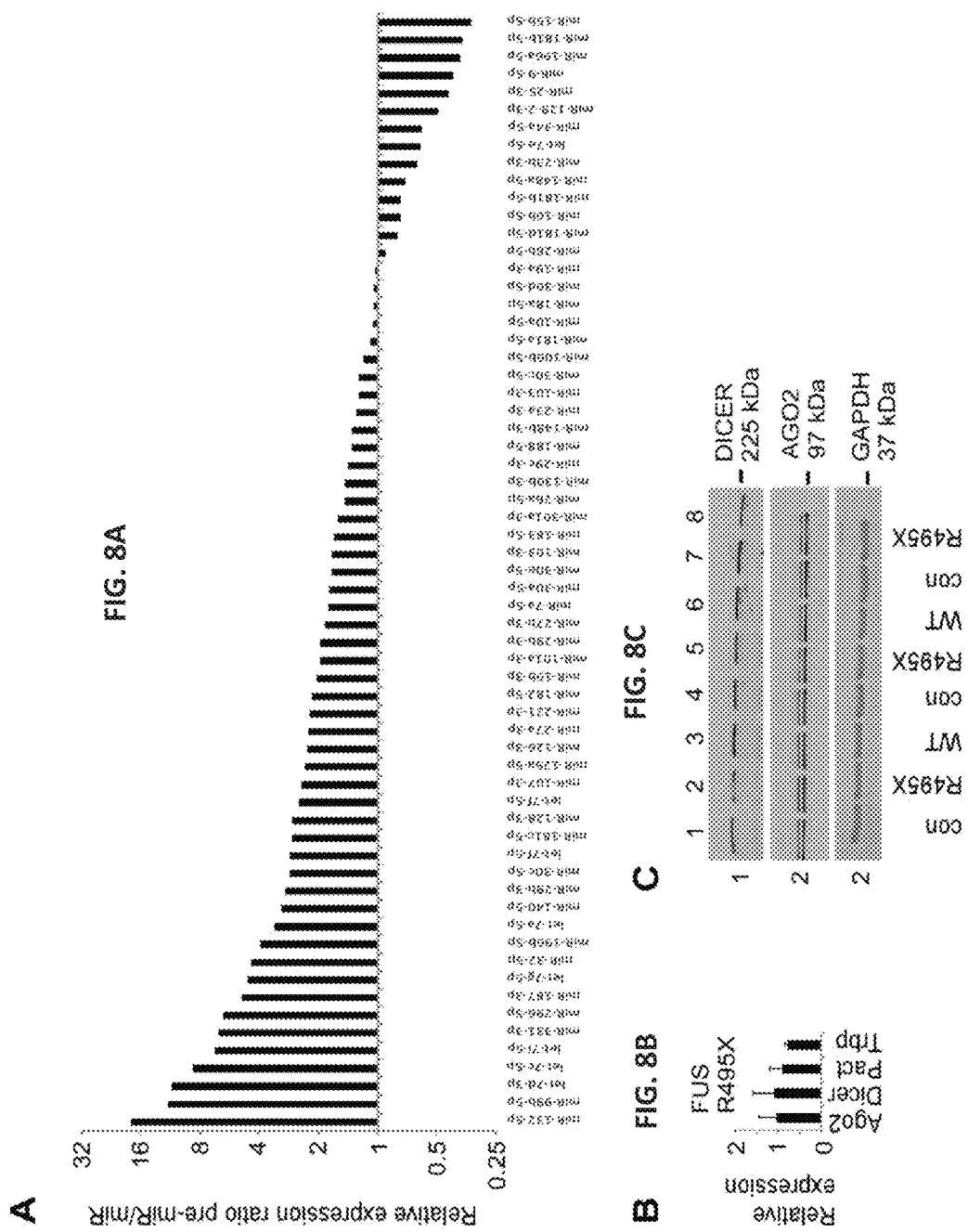

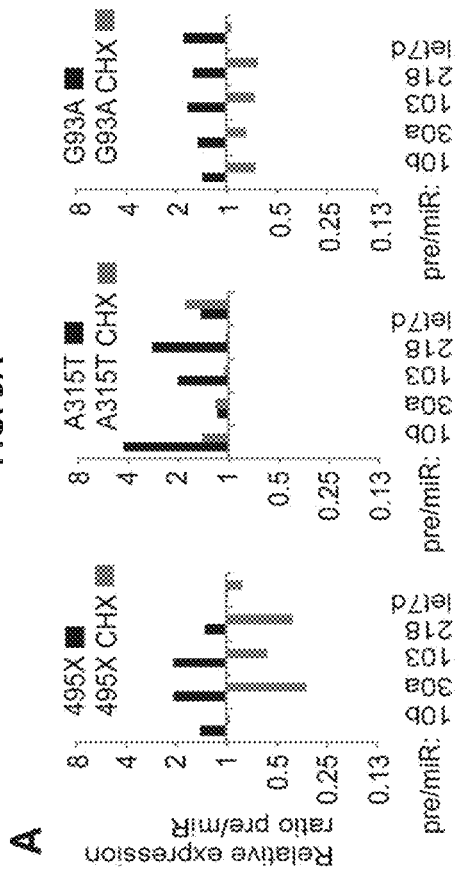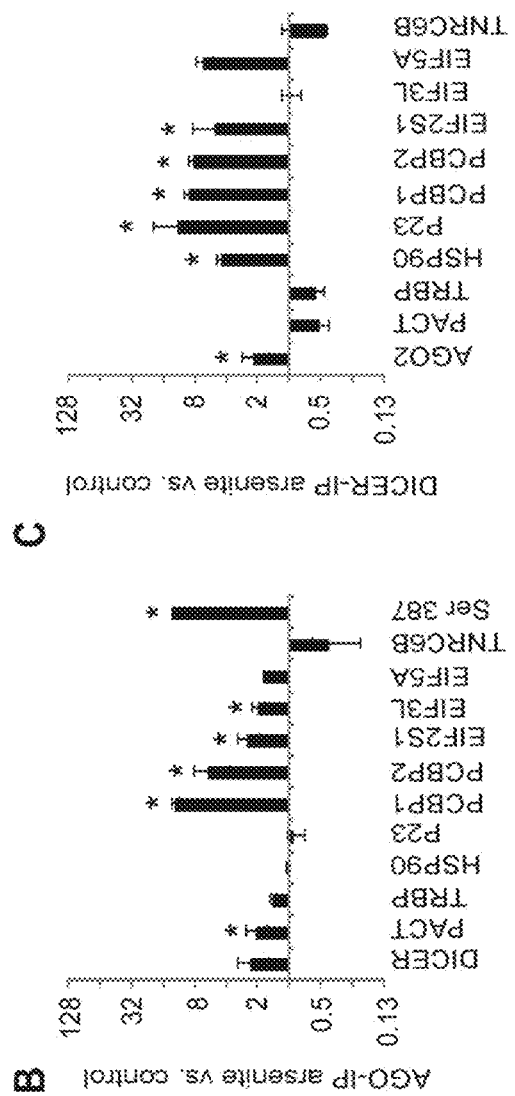

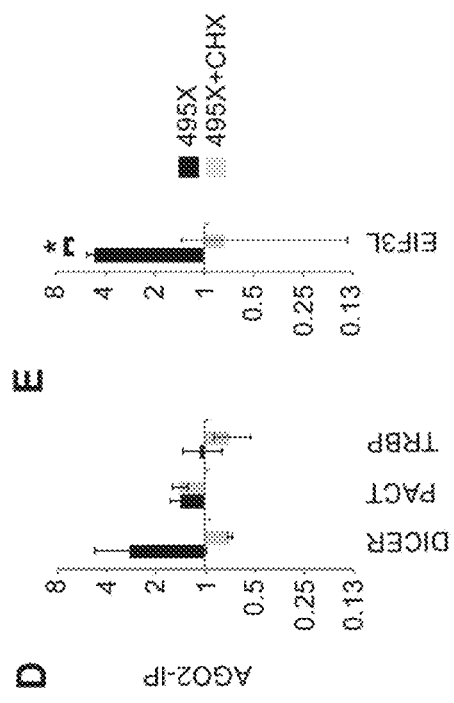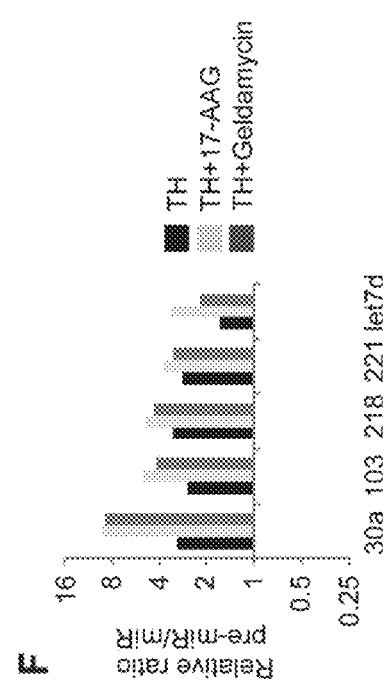
FIG. 9D  FIG. 9E  FIG. 9F

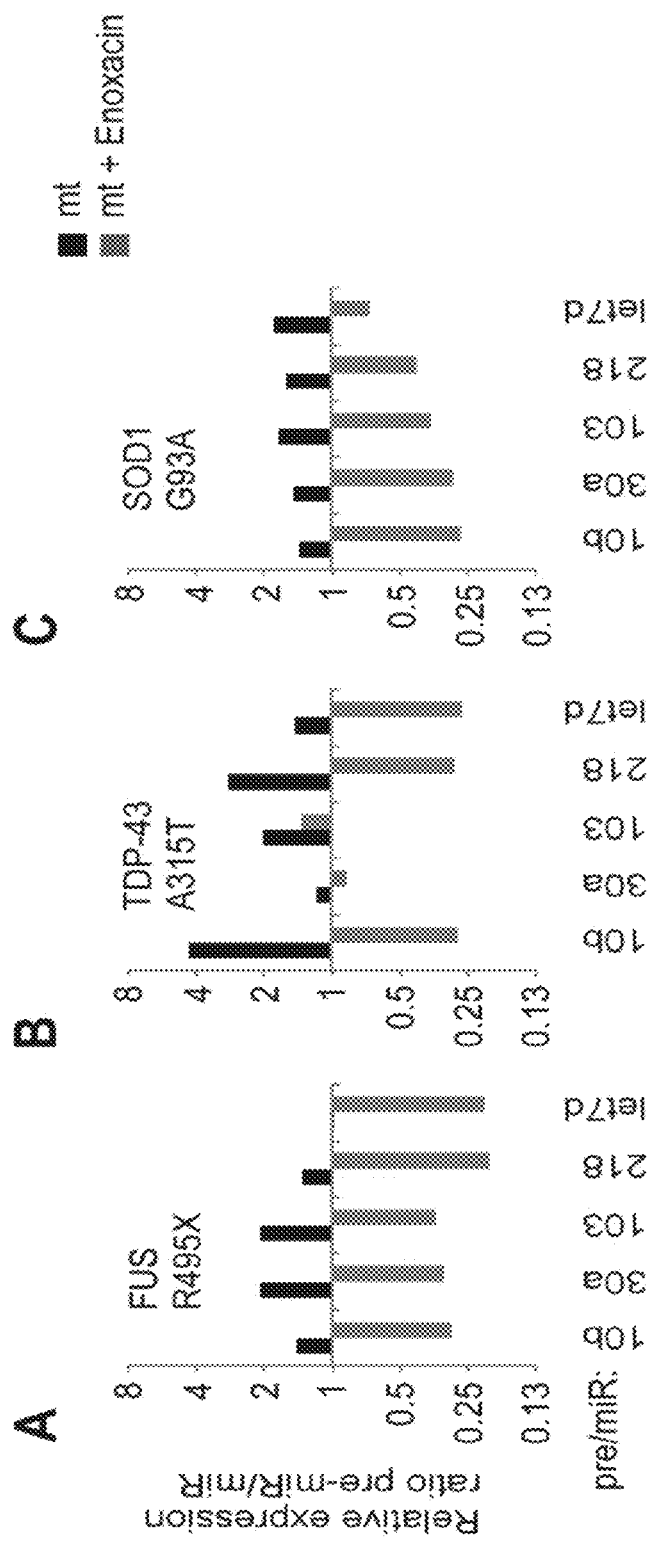

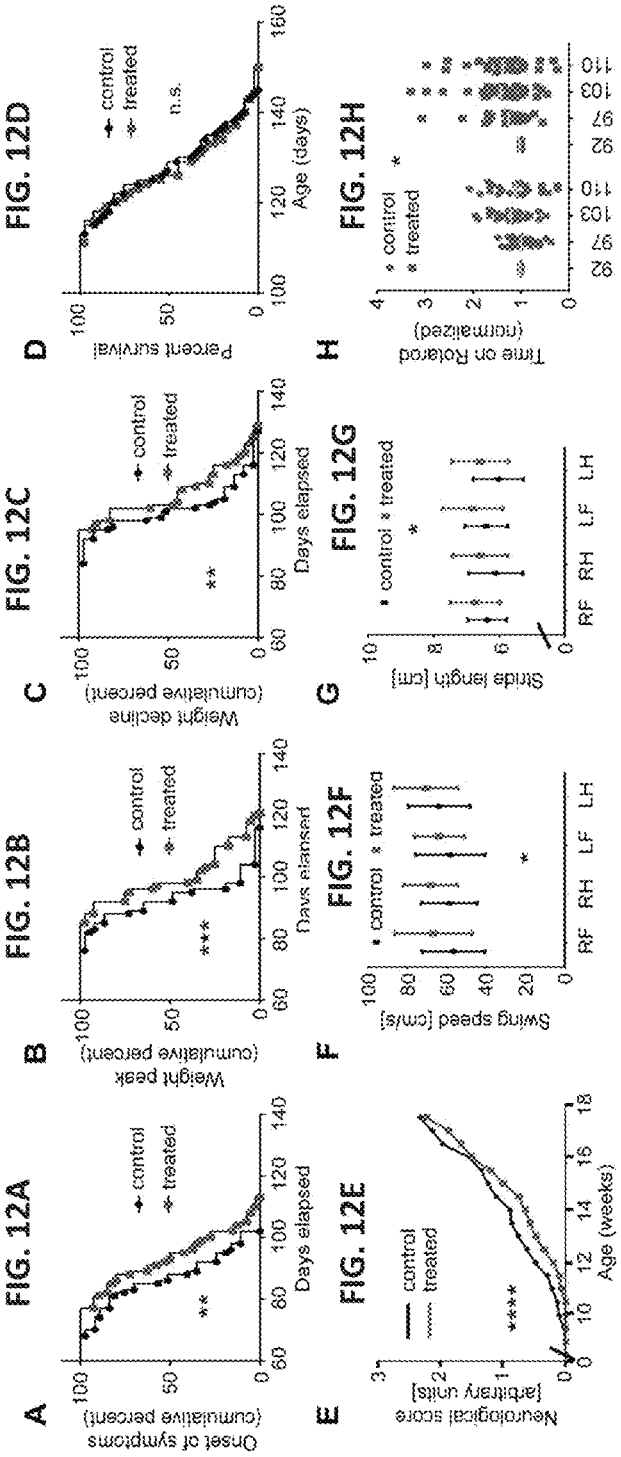

METHODS OF DIAGNOSING AND TREATING MOTOR NEURON DISEASES AND OTHER CELLULAR STRESS-RELATED DISEASES

RELATED APPLICATIONS

This application is a Continuation-in-Part (CIP) of PCT Patent Application No. PCT/IL2013/050655 filed Jul. 31, 2013, which claims the benefit of priority under 35 USC 119(e) of U.S. Provisional Patent Application No. 61/677,494 filed Jul. 31, 2012. The contents of all of the above applications are incorporated by reference as if fully set forth herein.

SEQUENCE LISTING STATEMENT

The ASCII file, entitled 60997SequenceListing.txt, created on Feb. 2, 2015, comprising 25,351 bytes, submitted concurrently with the filing of this application is incorporated herein by reference.

FIELD AND BACKGROUND OF THE INVENTION

The present invention, in some embodiments thereof, relates to methods of diagnosing and treating motor neuron diseases and other cellular stress-related diseases.

Motor neuron diseases (MND) and frontotemporal dementia belong to a group of neurological disorders attributed to the destruction of motor neurons of the central nervous system and degenerative changes in the motor neuron pathway. Such diseases are different from other neurodegenerative diseases including Parkinson's disease, Alzheimer's disease, olivopontocerebellar atrophy, etc., which are caused by the destruction of neurons other than motor neurons. Typically, MNDs are progressive, degenerative disorders that affect upper and lower motor neurons, leading to successive global muscular denervation. Generally, MNDs strike in middle age, although a wide age range of symptomatical disease onset can be observed, spanning from age 18 to 85 for several already studied mutants. Symptoms may include difficulty swallowing, limb weakness, slurred speech, impaired gait, facial weakness and muscle cramps. At the end stage of the disease, the respiratory musculature loses its innervation due to the death of motor neurons, which is usually the final cause of death of ALS patients. The cause(s) of most MNDs are not known, but environmental, toxic, viral or genetic factors are all suspects.

Motor neurons, including upper motor neurons and lower motor neurons, affect voluntary muscles, stimulating them to contract. Upper motor neurons originate in the cerebral cortex and send fibers through the brainstem and the spinal cord, and are involved in controlling lower motor neurons. Lower motor neurons are located in the brainstem and the spinal cord and send fibers out to muscles. Lower motor neuron diseases are diseases involving lower motor neuron degeneration. When a lower motor neuron degenerates, the muscle fibers it normally activates become disconnected and do not contract, causing muscle weakness and diminished reflexes. Loss of either type of neurons results in weakness, muscle atrophy (wasting) and painless weakness are the clinical hallmarks of MND (for further clinical definition see Online Mendelian Inheritance in Man®).

Amyotrophic Lateral Sclerosis (ALS) is a fatal motor neuron disease characterized by a loss of pyramidal cells in the cerebral motor cortex (i.e., giant Betz cells), anterior spinal motor neurons and brain stem motor neurons, and degeneration thereof into pyramidal cells. ALS shows, from a clinical aspect, both upper motor neurons and lower motor neurons signs, and shows rapid clinical deterioration after onset of the disease, thus leading to death within a few years.

Like many other motor neuron diseases, only a small percentage (about 10%-20%) of ALS is inherited. Genetic epidemiology of ALS has revealed at least 12 chromosome locations accountable for the inheritance of disease (ALS1 to ALS12). Among these, several genes have been identified. The first was identified in 1993 as the cytosolic Cu/Zn superoxide dismutase (SOD-1) gene that accounts for 20% of the autosomal dominant form of ALS [Rosen et al., (1993) Nature, 362(6415):59-62].

Frontotemporal Dementia is a neurodegenerative disease of humans which share in common with ALS etiopathological genetic causes, including mutations in genes such as TDP-43 and FUS. In addition a fraction of the patients' populations suffers from both Frontotemporal Dementia and ALS. Thus these diseases are on one molecular and clinical spectrum. Riluzole is the sole drug approved for ALS in U.S. and Japan.

Riluzole was originally developed as an anticonvulsant inhibiting glutamate release and has been reported in several clinical trials to exhibit only slight efficacy for the survival of ALS patients (Rowland L P and Shneider N A, 2001, N Engl J Med, 344, 1688-1700; and Turner M R and Parton M J, 2001, Semin Neurol 21: 167-175).

microRNAs (also known as miRNAs) are 20- to 24-nucleotide (nt) RNA molecule members of the family of non-coding small RNAs. microRNAs were identified in mammals, worms, fruit flies and plants and are believed to regulate the stability of their target messenger RNA (mRNA) transcripts in a tissue- and cell type-specific manner. Principally, micro-RNAs regulate RNA stability by either binding to the 3'-untranslated region (3'-UTR) of target mRNAs and thereby suppressing translation, or in similar manner to siRNAs, binding to and destroying target transcripts in a sequence-dependent manner.

microRNAs have been implicated in various neurological diseases such as ALS, Fragile X syndrome, spinal muscular atrophy (SMA), early onset parkinsonism (Waisman syndrome) and X-linked mental retardation (MRX3).

WO2010/06424 teaches the use of an agent which upregulates an activity or amount of miRNA-9 or miRNA-9* in the preparation of a medicament for the treatment of a motor neuron diseases (MNDs) including ALS.

U.S. Patent Application 20060247193 teaches administration of over 100 miRNAs for the treatment of MNDs including ALS.

U.S. Patent Application 20090246136 teaches administration of miR-206 and/or miR-1 for the treatment of MNDs including ALS.

Additional relevant background art includes U.S. Patent Application 20080176766.

Interestingly, specific mutations in genes encoding for RNA binding proteins, such as TAR DNA-binding protein 43 (TDP-43) and fused in sarcoma (FUS)[1,2] have been associated with the etiology of ALS[3-6], as well as heterogeneous nuclear ribonucleoprotein A1 (hnRNPA1; Kim et al. (2013) Nature 495(7442): 467-473) and valosin containing protein (VCP; Buchan et al. (2013) Cell 153(7): 1461-1474).

Buratti et al. 2010 (RNA Biology 7:4(420-429) describe a role of TDP-43 and FUS/TLS in RNA metabolism. Mislocalization of these proteins can alter the functioning of the Drosha processing enzyme both with regard to the general miRNA cellular population and for selected members.

Buratti et al. 2010 FEBS J. 2268-2281 shows that TDP-43 affect selected miRNA levels.

Kawahara et al. 2012 PNAS 109(9):3347-3352 shows that cytoplasmic TDP-43 interacts with the Dicer complex and promotes processing of a selected population of miRNAs via binding to the terminal loops.

Neuronal cytoplasmic protein aggregation and defective RNA metabolism were suggested to be common pathogenic mechanisms involved in ALS and possibly in other neurodegenerative disorders. Furthermore, polymorphic miRNA-mediated gene regulation has been specifically suggested as a mechanism for neurodegeneration, including motor neuron diseases[7-10]. In addition, it was recently demonstrated that loss of miRNAs bioprocessing by inactivation of Dicer1 is sufficient to cause spinal motoneuron degeneration[11].

RELATED BACKGROUND ART

U.S. 20120071539 discloses methods and compositions comprising chemical compounds that modulate the silencing of a polynucleotide of interest in a cell are provided. Such chemical compounds when used in combination with an appropriate silencing element can be used to modulate (increase or decrease) the level of the polynucleotide targeted by the silencing element. Methods of using such compositions both in therapies involving RNAi-mediated suppression of gene expression, as well as, in vitro methods that allow for the targeted modulation of expression of a polynucleotide of interest are provided. Pharmaceutical or cosmetic compositions comprising such compounds and silencing elements also are disclosed. Methods for screening a compound of interest for the ability to modulate the activity of a heterologous silencing element also are provided.

Additional background related art: U.S. Pat. No. 6,756,369.

SUMMARY OF THE INVENTION

According to an aspect of some embodiments of the present invention there is provided a method of treating a cellular stress-related disease in a subject in need thereof, the method comprising administering to the subject a therapeutically effective amount of an agent capable of enhancing processing of a pre-miRNA, thereby treating the cellular stress-related disease in the subject.

According to an aspect of some embodiments of the present invention there is provided a method of treating a motor neuron disease (MND) in a subject in need thereof, the method comprising administering to the subject a therapeutically effective amount of an agent capable of enhancing processing of a pre-miRNA, thereby treating the motor neuron disease (MND) in the subject.

According to an aspect of some embodiments of the present invention there is provided an agent capable of enhancing processing of a pre-miRNA for use in treating a motor neuron disease (MND) in a subject in need thereof.

According to some embodiments of the invention, the agent capable of enhancing processing of pre-miRNA is selected from the group consisting of a nuclear processing enhancer, a nuclear export enhancer and a cytoplasmic processing enhancer.

According to some embodiments of the invention, the cytoplasmic processing enhancer comprises a Dicer enhancer.

According to some embodiments of the invention, the Dicer enhancer comprises a quinolone.

According to some embodiments of the invention, the quinolone is selected from the group consisting of enoxacin, ciproflaxin and ofloxacin.

According to some embodiments of the invention, the Dicer enhancer is selected from the group consisting of enoxacin, ciproflaxin and ofloxacin.

According to some embodiments of the invention, the quinolone comprises enoxacin.

According to some embodiments of the invention, the method further comprises administering to the subject a therapeutically effective amount of an agent capable of decreasing cellular stress.

According to some embodiments of the invention, the therapeutically effective amount of the agent capable of decreasing cellular stress is reduced as compared to an effective amount thereof when administered in a therapeutic regimen devoid of the agent capable of enhancing processing of a pre-miRNA.

According to some embodiments of the invention, the agent capable of decreasing cellular stress is capable of inhibiting formation and/or enhancing disaggregation of stress granules.

According to some embodiments of the invention, the agent capable of decreasing cellular stress is selected to target a factor associated with the formation or disaggregation of the stress granules.

According to some embodiments of the invention, the factor is selected from the group consisting of eukaryotic translation initiation factor 2 (eIF2A), protein kinase RNA-like endoplasmic reticulum kinase (PERK), heme-regulated eIF2α kinase (HRI), Protein kinase RNA-activated (PKR), general control nonderepressible 2 (GCN2), argonaute (Ago), protein activator of the double-stranded RNA-activated protein kinase (PACT), heterogeneous nuclear ribonucleoprotein A1 (hnRNPA1), TAR DNA-binding protein 43 (TDP-43), fused in sarcoma (FUS), valosin containing protein (VCP), SMN and PRMT1.

According to some embodiments of the invention, the cellular stress is selected from the group consisting of unfolded protein response (UPR)/ER stress, oxidative stress, heat shock stress, hyperosmolarity stress, viral infection stress, irradiation stress and nutrient stress.

According to some embodiments of the invention, the cellular stress-related disease comprises a neurodegenerative disease.

According to some embodiments of the invention, the neurodegenerative disease is selected from the group consisting of Amyotrophic Lateral Sclerosis (ALS), Parkinson's disease, Multiple Sclerosis, multi-system atrophy, Alzheimer's disease, stroke, epilepsy, progressive supranuclear palsy, frontotemporal dementia and Pick's disease.

According to some embodiments of the invention, the cellular stress-related disease is selected from the group consisting of a cancer, a protein folding/misfolding disease, a myelinating cell-related disease, a neurodegenerative disease, a metabolic disease, a diabetes mellitus, a Wolcott-Rallison syndrome, an ischemia/reperfusion injury, a secondary degeneration after trauma, a stroke, a CNS intoxication, a neurodegeneration, a glaucoma, a macular degeneration, a neurodegeneration, a multiple sclerosis, a systemic lupus erythematosis, an autoimmune uveitis, a graft versus host disease, a graft rejection, an arthritis, a systemic inflammatory response syndrome (SIRS), an inflammatory bowel disease (IBD), an adult respiratory distress syndrome (ARDS), a psoriasis, an atherosclerosis, a myocardial infarction, a radiation disease, a hyperthermia, a neoplasia, a hypoxia, a hypoglycemia, a liver disease, a fulminant toxic liver, a kidney failure, an infertility, a bipolar disorder, and a viral infection.

According to some embodiments of the invention, the MND comprises amyotrophic lateral sclerosis (ALS).

According to an aspect of some embodiments of the present invention there is provided a method of treating an Amyotrophic Lateral Sclerosis (ALS) in a subject in need thereof, the method comprising administering to the subject a therapeutically effective amount of an agent capable of enhancing processing of a pre-miRNA and an anti-ALS agent, thereby treating the ALS in the subject.

According to an aspect of some embodiments of the present invention there is provided an agent capable of enhancing processing of a pre-miRNA and an anti-ALS agent for use in treating an Amyotrophic Lateral Sclerosis (ALS) in a subject in need thereof.

According to some embodiments of the invention, the anti-ALS agent comprises a Riluzole.

According to an aspect of some embodiments of the present invention there is provided a pharmaceutical composition comprising as an active ingredient an agent capable of enhancing processing of a pre-miRNA, an anti-ALS agent and a pharmaceutically acceptable carrier or diluent.

According to an aspect of some embodiments of the present invention there is provided an article of manufacture comprising an agent capable of enhancing processing of a pre-miRNA and an anti-ALS agent being packaged in a packaging material and identified in print, in or on the packaging material for use in the treatment of ALS.

According to some embodiments of the invention, the agent capable of enhancing processing of a pre-miRNA comprises a quinolone.

According to some embodiments of the invention, the quinolone comprises enoxacin.

According to an aspect of some embodiments of the present invention there is provided a method diagnosing a MND, the method comprising analyzing in a sample of a subject in need thereof:

(i) total miR expression; and optionally (ii) total pre-miR expression, wherein a down-regulation in the (i) or (i)/(ii) beyond a predetermined threshold is indicative of the MND.

According to an aspect of some embodiments of the present invention there is provided a method diagnosing a MND, the method comprising analyzing in a sample of a subject in need thereof:

(i) a miR expression; and (ii) an expression of a precursor of the miR, wherein a down-regulation in (i)/(ii) beyond a predetermined threshold is indicative of the MND.

According to some embodiments of the invention, the miR is miR-9.

According to some embodiments of the invention, the MND is selected from the group consisting of ALS, primary lateral sclerosis, progressive muscular atrophy, pseudobulbar palsy, progressive bulbar palsy, lower motor neuron disease and spinal muscular atrophy.

According to some embodiments of the invention, the motor neuron disease comprises amyotrophic lateral sclerosis (ALS).

According to some embodiments of the invention, the ALS is associated with a gene having a mutation associated with an impaired RNA metabolism.

According to some embodiments of the invention, the gene is selected from the group consisting of TDP-43 and FUS.

According to some embodiments of the invention, the ALS is an inherited ALS.

According to some embodiments of the invention, the ALS is a sporadic ALS.

According to some embodiments of the invention, the sample comprises a cerebrospinal fluid (CSF) sample or a blood sample.

According to an aspect of some embodiments of the present invention there is provided a method of identifying an agent for the treatment of a MND, the method comprising:

(a) contacting a motor neuron of an ALS patient or an ALS model with a candidate agent;

(b) analyzing prior to (a) and following (a):

(i) total miR expression in the motor neuron; and optionally (ii) total pre-miR expression in the motor neuron, wherein an up-regulation in the (i) or (i)/(ii) beyond a predetermined threshold following (a) as compared to prior to (a), is indicative of that the candidate compound is a therapeutic agent for the treatment of MND.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1B:
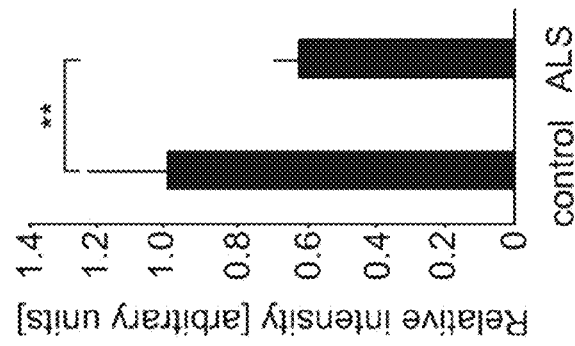
Figure 1C:
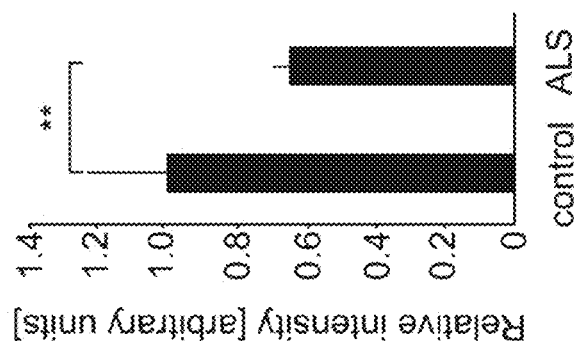
Figure 1A:
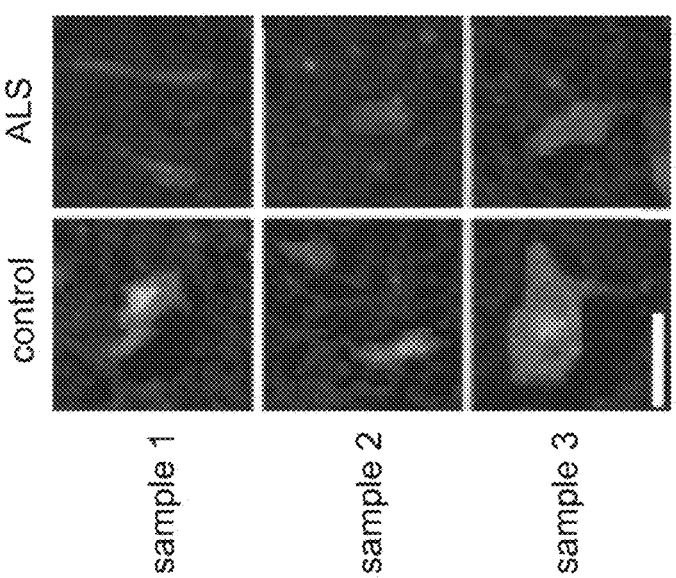
Figure 2A:
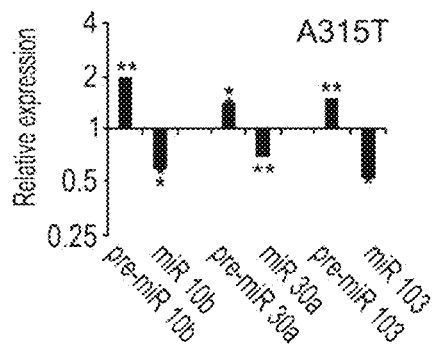
Figure 2B:
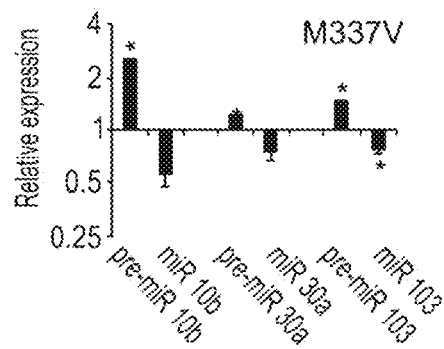
Figure 2C:
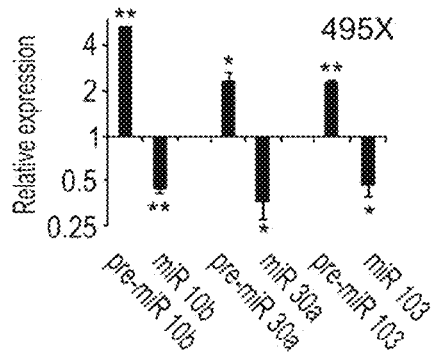
Figure 2D:
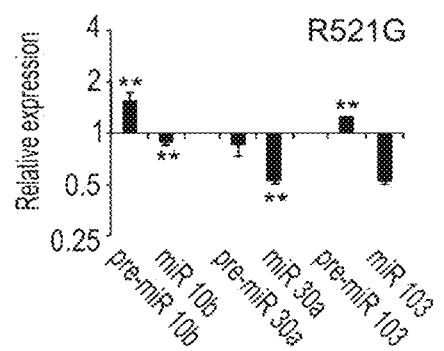
Figure 2E:
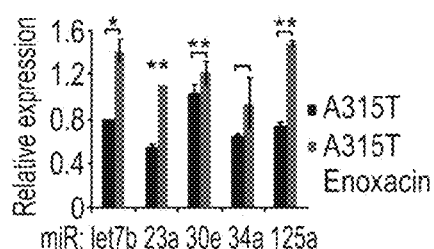
Figure 2F:
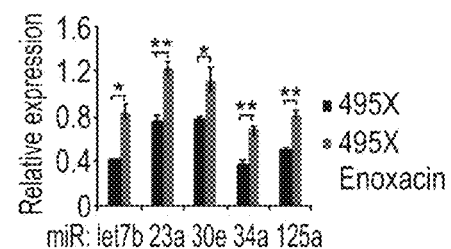
Figure 2G:
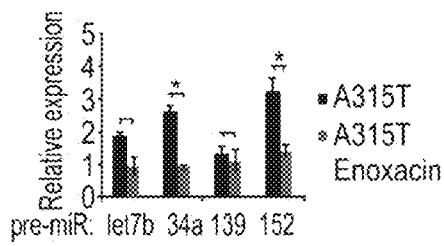
Figure 2H:
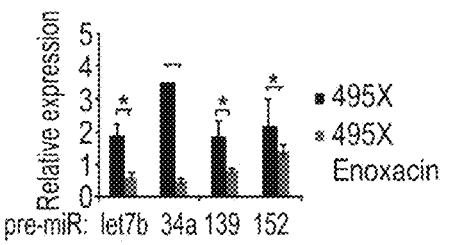

FIGS. 1A-C show that miRNAs are globally reduced in motoneurons of sporadic ALS patients. (FIG. 1A) Representative fluorescent in-situ hybridization micrographs for miR-9 in non-neurodegeneration (control) and ALS motoneurons (patients). Scale bar indicates 10 µM. Bargraph revealing miR-9 (FIG. 1B) or miR-124 (FIG. 1C) signal-intensity, quantified in 300 different motoneurons, after in-situ performed on samples from two ALS-patients and two non-ALS controls. Arbitrary units, normalized to the expression-signal of small-RNA U6.

FIGS. 2A-H show impaired miRNA processing upon expression of ALS-causing TDP-43 or FUS mutants can be rescued by Enoxacin. Transfection of Doxycyclin-inducible forms of ALS-causing (FIG. 2A) TDP-43$^{A315T}$, (FIG. 2B) TDP-43$^{M337V}$, (FIG. 2C) FUS$^{495X}$, or of (FIG. 2D) FUS$^{R521G}$ mutants, into NSC-34 cells results in downregulation of mature miRNAs, whilst pre-miRNA levels are correspondently upregulated. Depicted are bar-graph representations of relative miRNA expression levels in cells, transfected with GFP and treated with Doxycyclin, compared to the expression of the small RNAs U6 or 5S, on a $\log_2$ scale. Introduction of 100 μM Enoxacin recovers the downregulation of mature miRNA expression in HEK293 cells transfected with ALS-causing mutants: (FIG. 2E) TDP-$43^{A315T}$ or (FIG. 2F) $FUS^{495X}$ and reverses pre-miRNA upregulation by (FIG. 2G) TDP-$43^{A315T}$ or (FIG. 2H) $FUS^{495X}$. Data normalized to miRNA levels in cultures that were transfected with GFP and treated with Doxycyclin and to the expression of the small RNAs U6 or 5S. Pre-miRNA expression normalized to beta-actin. Statistics were performed using two-tailed Student's t-test with post-hoc Benjamini-Hochberg corrections. *p-value<0.05; **p-value<0.005.

Figure 3:
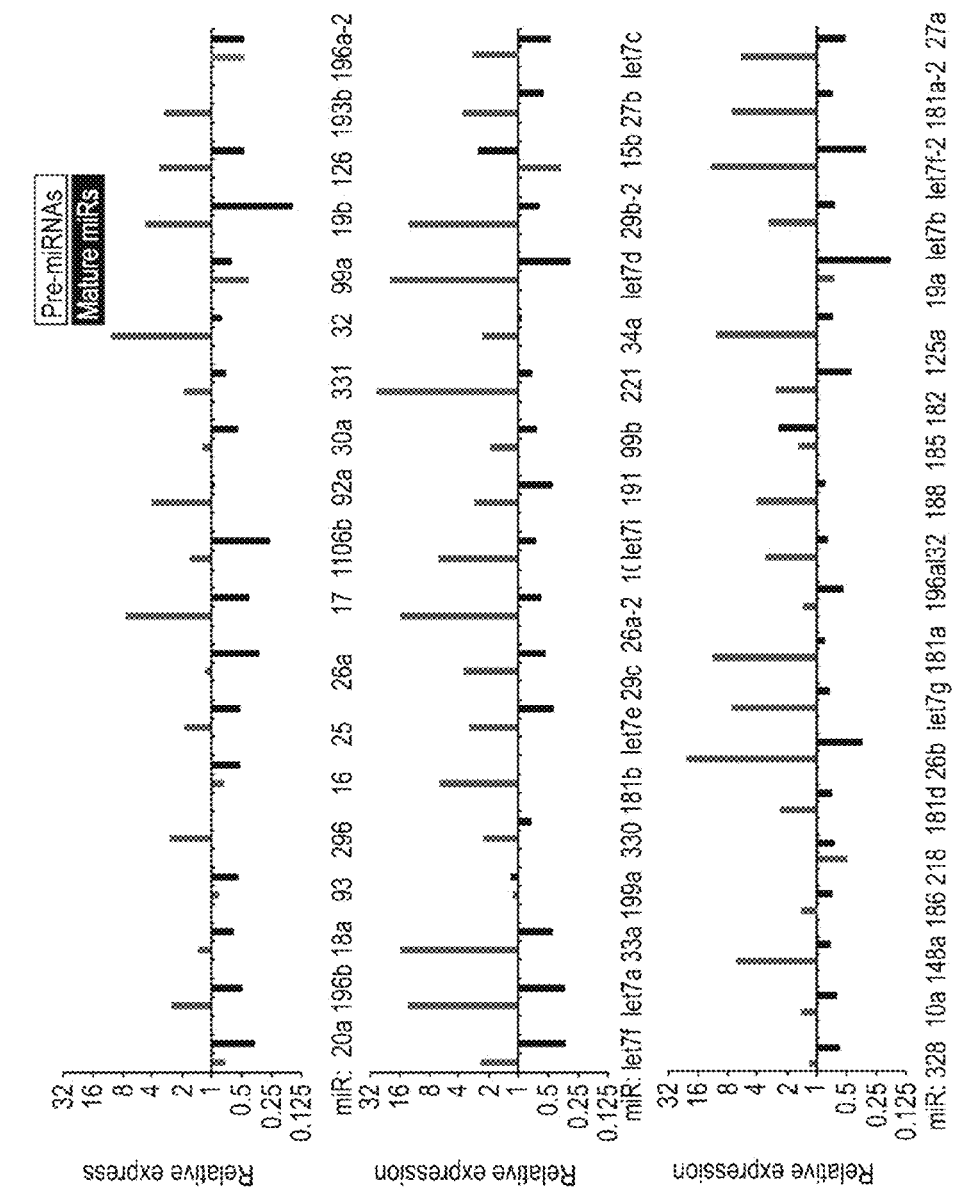

FIG. 3 shows impaired miRNA processing upon expression of ALS-causing TDP-43 or FUS mutants can be rescued by Enoxacin. The impact of FUS495X was globally studied by deep sequencing of pre-miRNAs and mature miRNAs, revealing widespread repression of Dicer activity and miRNA maturation.

FIGS. 4A-D show Enoxacin impact on disease progression. (FIG. 4A) Continuous administration of Enoxacin into the drinking water of SOD1 G93A mice had marginal effect on overall lifespan but exhibited beneficial impact on (FIG. 4B) neurological score, (FIG. 4C) gross strength in a hang-wire test and (FIG. 4D) on overall locomotive function in a computerized cat-walk assay.

Figure 5A:
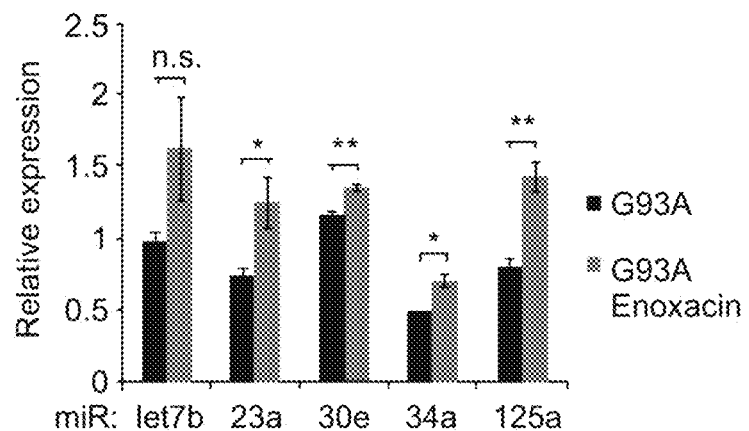
Figure 5B:
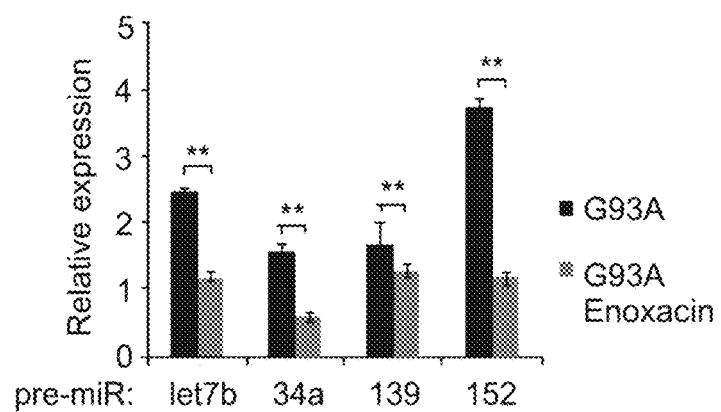

FIGS. 5A-B show that miR-expression is altered in familial forms of SOD1 mutant ALS and can be normalized in vitro by Enoxacin. Introduction of 100 μM Enoxacin recovers the downregulation of mature miRNA expression in HEK293 cells transfected with ALS-causing mutants: (FIG. 5A) $SOD1^{G93A}$ and reverses pre-miRNA upregulation by (FIG. 5B) $Sod1^{G93A}$. Data normalized to miRNA levels in cultures that were transfected with GFP and treated with Doxycyclin and to the expression of the small RNAs 5S. Pre-miRNA expression normalized to beta-actin. Statistics were performed using two-tailed Student's t-test with post-hoc Benjamini-Hochberg corrections. *p-value<0.05; **p-value<0.005.

FIGS. 6A-F show that microRNAs are down-regulated in motor neurons of human ALS patients. Volcano plots of p-values (y-axis $\log_{10}$ scale) for relative miRNA expression (x-axis $\log_2$ scale). Black dots indicate p<0.05, light gray=non significant. (FIG. 6A) Lumbar motor neurons (8 sporadic ALS nervous systems, 9 non-neurodegeneration controls). (FIG. 6B) Anterior horn tissue without motor neurons from the same individuals (10 sporadic ALS nervous systems, 9 controls), and (FIG. 6C) miRNA expression in Clarke's column (3 sporadic ALS nervous systems vs. 3 controls). (FIG. 6D) Representative micrographs with in-situ hybridization for miR-9 and miR-124, scale bar indicates 10 μM. Bar-graph displays signal-intensity, quantified in 300 different motor neurons of 2 ALS nervous systems and 2 controls, normalized to U6 in-situ hybridization signal. Error bars represent s.d. (FIG. 6E) miRNA expression in lumbar motor neurons (2 familiar ALS nervous systems, 9 controls) and respective (FIG. 6F) anterior horn tissue depleted of motor neurons.

FIGS. 7A-L show that cellular stress affects pre-miRNA processing. (FIG. 7A) miRNA expression level analysis in the motor neuron cell line NSC-34, treated with 6.25 nM Thapsigargin for 24 hrs, relative to cells treated with carrier alone (DMSO). Shown are average and s.d. of qPCR analyses of 3 independent experiments. Pre-miRNAs (light grey, normalized to Gapdh) and miRNAs (dark grey, normalized to Snord68). (FIG. 7B) mRNA levels encoding for proteins involved in the canonical stress response, normalized to the expression of beta-actin. (FIG. 7C) miRNA expression level analysis in mouse embryonic motor neurons, treated with 5 nM Thapsigargin for 72 hrs, relative to cells treated with carrier alone (DMSO). Shown are average and s.d. of qPCR analyses of three independent experiments. Pre-miRNAs (light grey, normalized to Gapdh and beta actin) and miRNAs (dark grey, normalized to Snord70). (FIG. 7D) mRNA markers of the canonical stress response, normalized to the expression of beta-actin. miRNA expression level analysis in NSC-34 cells, treated with Paraquat (PQ) (1 mM, 12 hrs, FIG. 7E) and sodium arsenite (0.5 mM, 60 min, FIG. 7F). pre-miRNA normalized to beta-actin mRNA (FIGS. 7E-F) and miRNAs to 5S (FIG. 7E) or to U6 and 5S (FIG. 7F). (FIGS. 7G-I) miRNA expression level analysis in mouse embryonic Wild-type fibroblasts (light grey) or phospho-mutant eIF2a S51A cells (black) treated with Thapsigargin (5 nM, 72 hrs) relative to carrier alone. Pre-miRNA (FIG. 7G) and mature miRNA (FIG. 7H) levels normalized to Gapdh and Snord68, respectively. (FIG. 7I) ATF4, which is induced by phosphorylation of eIF2a, was not induced in phospho-mutant eIF2a S51A cells. Significance of p-values from ANOVA tests is indicated by *p<0.05; **p<0.01. (FIGS. 7J-K) Western-Blot analysis of lysates from untreated NSC-34 cells (control) or cells treated with sodium arsenite (0.5 mM, 60 min). Phospho-specific immunodetection of eIF2a S51 phosphorylation (peIF2a) and total eIF2a levels (FIG. 7J), Dicer and Ago2 levels (FIG. 7K). (FIG. 7L) miRNA expression level analysis in mouse embryonic fibroblasts treated with Puromycin (1 μg/ml, 24 hrs), relative to cells treated with carrier alone (water). Pre-miRNAs (light grey, normalized to Gapdh) and miRNAs (dark grey, normalized to Snord68).

FIGS. 8A-C show that expression of ALS-causing genes inhibits pre-miRNA processing. (FIG. 8A) Global analysis of RNA by next-generation sequencing depicts the ratio of pre-miRNA to miRNA expression levels in NSC-34 cells, transfected with FUS 459X expression vector. Cells harvested 72 hrs post-transfection and data normalized to control plasmid transfection. Data presented for 63 pre-miRNA:mature miRNA pairs, for which robust data was gained with more than 50 reads in the control. Pre-miRNA normalized to Snord72 and Snord95 whereas mature miRNAs normalized to spike-in synthetic RNA controls. (FIG. 8B) mRNA levels encoding for protein components of the Dicer complex were measured and normalized to the expression of Gapdh (FUS R495X). (FIG. 8C) Western-Blot study of DICER and AGO2 in NSC-34 protein extract, transfected with plasmids that drive the expression of FUS or ALS-causing truncated form, FUS R495X. Experiment conducted in two biological replicates, while lanes 7,8 are technical loading replicates of lanes 1,2 respectively. GAPDH loading controls electrophorized with AGO2 (gel 2, 10% polyacrylamide) and DICER electrophorized separately (gel 1, 6% polyacrylamide).

FIGS. 9A-F show that stress granule formation controls miRNA biogenesis. (FIG. 9A) The ratio of pre-miRNA to mature miRNA levels in NSC-34 cells, transfected with plasmids as indicated and in cells treated for 72 hrs with carrier alone (water, black) or with cycloheximide (CHX, 0.02 μg/ml, gray). Data normalized to control plasmid transfection. Pre-miRNAs further normalized to Gapdh (for FUS R495X, TDP-43 A315T) or to beta-actin (SOD1 G93A) and miRNA levels normalized to Snord68. Average of three independent experiments except for pre-miRNAs in the study of FUS R495X (n=2). Targeted quantitative mass spectrometry analysis of changes in the binding of Ago2 or Dicer to a set of proteins interactors under stress (FIGS. 9B-E). Immunoprecipitated Ago2-Flag (FIG. 9B) or Dicer-Flag (FIG. 9C) from HEK 293 cells, cultured under basal conditions or treated with sodium arsenite (0.5 mM, 60 min) was subjected to targeted mass-spectrometry analysis. Data is averaged from two or three different peptide standards per protein and normalized to the levels of co-immunoprecipiated peptides from untreated cells. Statistically significant result in a student t-test, between arsenite and control treatment is denoted (*p<0.05). Targeted mass spectrometry of (FIG. 9D) Dicer cofactors or (FIG. 9E) SG components, immunoprecipitated with AGO-Flag in FUS R495X-expressing HEK 293 that were further treated for 72 hrs with carrier alone or Cycloheximide (0.02 μg/ml). (FIG. 9F) The ratio of pre-miRNA to mature miRNA levels in mouse embryonic fibroblasts, pretreated for 5 hrs with HSP90 inhibitors (17-AAG, 1 μM or Geldanamycin, 1 μM) and then incubated for 36 more hours with Thapsigargin (5 nM) in combinations with the respective HSP90 inhibitor. Bars represent the average of three independent experiments. miRNA normalized to the expression levels of Snord70, and pre-miRNA normalized to Gapdh.

FIGS. 10A-C show that Enoxacin ameliorates ALS-induced defect in pre-miRNA processing. Ratio of pre-miRNA to miRNA expression levels in NSC-34 cells, transfected with plasmids that drive the expression of FUS R459X (FIG. 10A), TDP-43 A315T (FIG. 10B) or SOD1 G93A (FIG. 10C), relative to control plasmid transfection. Analysis of cells treated for 72 hrs with carrier only (water, black bars) or upon administration of 100 μM Enoxacin into the medium (gray bars). pre-miRNA levels were measured by qPCR and normalized to the expression of Gapdh (FUS R495X, TDP-43 A315T) or beta-actin (SOD1 G93A). miRNA levels were normalized to the small RNA Snord68. Average of 3 independent experiments, except for pre-miRs in FUS R495X (n=2).

FIGS. 11A-D show that miRNAs are down-regulated in the SOD1 G93A mouse model of ALS. Multiple time-point analysis of miRNA expression in the lumbar spinal cords (L4, L5) of SOD1 G93A mutant mice relative to wild-type sibling controls (3 spinal cords per group). (FIG. 11A) qPCR analysis of miRNAs normalized to average of snoRNA202 and snoRNA234. (FIG. 11B) Levels of mRNA encoding for protein components of the Dicer complex were measured and normalized to the expression of Gapdh. (FIG. 11C) Depicted are ratios of miRNA expression in the lumbar spinal cords (L4, L5) of SOD1 G93A mice relative to wild-type sibling controls (3 animals per group, black bars) and the ratios of miRNA expression after Enoxacin treatment of SOD1 G93A mice (5 animals, 800 mg/kg body weight per day for 48 days) versus untreated mice (4 animals, red bars). qPCR analysis of miRNAs was normalized to average of snoRNA202 and snoRNA234. (FIG. 11D) Levels of mRNA encoding for protein components of the Dicer complex were measured and normalized to the expression of Gapdh. 2-way ANOVA-testing with significant p-values indicated by *p<0.05, p<0.01, *p<0.001. Error bars, s.d.

FIGS. 12A-K show that Enoxacin therapy is beneficial for neuromuscular function in SOD1 G93A mouse model of ALS. Oral application of Enoxacin 800 mg/kg-bodyweight/day (n=40) or carrier (water; n=37) to SOD1 G93A male mice started day 42 of the mouse life. (FIG. 12A) Onset of symptoms (neurological score 1); Logrank Mantel-Cox test p=0.0025; (FIG. 12B) weight peak, *p=0.0002; (FIG. 12C) onset of weight decline, defined as the loss of 1 gram body-weight after the weight peak were measured; p=0.0099; (FIG. 12D) Kaplan-Meier survival plot reveals comparable life span of SOD1 G93A mice, regardless of therapy. n.s., not significantly different. (FIG. 12E) Average neurological score per cohort (n=40 Enoxacin treated, n=37 controls), 2-way ANOVA test, **p<0.0001. (FIGS. 12F and 12G) Fully automated gait Catwalk XT analysis (Noldus) with ten matched siblings per group: (FIG. 12F) Four-paws swing speed on day 73, 2-way ANOVA *p=0.027. (FIG. 12G) Four-paws stride length on day 80, 2-way ANOVA *p=0.012. (FIG. 12H) Longitudinal Rotarod performance test at multiple time points, normalized to initial performance at day 92 of each individual (n=25 control, n=29 Enoxacin). 2-way ANOVA with repeated measures for each individual, *p=0.047. Oral application of Enoxacin 200 mg/kg-bodyweight/day or carrier (water) to SOD1 G93A male mice started day 42 of the mouse life. (FIG. 12I) Longitudinal Rotarod test at multiple time points, normalized to initial performance at day 50 of each individual (n=7 control, n=6 Enoxacin). 2-way ANOVA with Sidak's multiple comparisons revealed significant drop in the performance of untreated mice at day 120, relative to day 50 (p<0.01), whereas Enoxacin treated mice exhibit stable performance at day 120. (FIG. 12J) Hangwire assay (n=15 control, n=16 Enoxacin), control vs. Enoxacin p=0.0023 as analyzed by the 2-way ANOVA. (FIG. 12K) Fully automated infrared-based homecage locomotion analysis (InfraMot, TSE-Systems) at 30 min. intervals over a period of 46 hrs, day 129-130, (n=5 control, n=6 Enoxacin). *p=0.012, 2-sided Student's t-test. Error bars, s.d.

FIGS. 13A-D show that Enoxacin therapy is beneficial for neuromuscular function in TDP-43 A315T mouse model of ALS. Oral application of Enoxacin 200 mg/kg-bodyweight/day (n=9) or carrier (water; n=8) to TDP-43 A315T mutant female mice started at day 42 of the mouse life. (FIG. 13A) Onset of symptoms (neurological score 1); 2-way ANOVA p=0.0013. (FIG. 13B) Hangwire assay, control vs. Enoxacin p=0.0079 as analyzed by the 2-way ANOVA. (FIG. 13C) Longitudinal Rotarod test at multiple time points, normalized to initial performance at day 48 of each individual (n=7 control, n=6 Enoxacin). 2-way ANOVA with Sidak's multiple comparisons, revealed significant drop in the performance of untreated mice at day 120, relative to day 50 (*p<0.05). Enoxacin treated mice exhibited improved performance on day 62 relative to day 48 (****p<0.0001) and exhibited stable performance up to day 120 of life. (FIG. 13D) Catwalk XT analysis (Noldus) revealed better performance, as assessed by four-paws stride length on day 83, 2-way ANOVA (*p=0.045). Error bars, s.d.

DESCRIPTION OF SPECIFIC EMBODIMENTS OF THE INVENTION

The present invention, in some embodiments thereof, relates to methods of diagnosing and treating motor neuron diseases and other cellular stress-related diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Amyotrophic Lateral Sclerosis (ALS) is a neurodegenerative disease of the human motor system. ALS-causing mutations were recently discovered in genes encoding for RNA-binding proteins and were associated with dysregulated RNA metabolism (mostly downregulated miRNA levels in ALS subjects).

While conceiving the present invention, the present inventors have hypothesized that since the general (non-specific) micro RNA (miRNA) metabolism is altered in motor neuron diseases (MNDs), the reversal of this altered metabolism can be used as a novel therapeutic modality for the treatment of such diseases.

The present inventors have affirmed this by showing that microRNAs are broadly downregulated in ALS motoneurons (FIGS. 1A-C and FIGS. 2A-D), whilst their precursors are present at high levels (FIGS. 2A-D and FIG. 3). The present inventors have further shown that ALS-causing mutations in RNA binding proteins hamper the dicing of microRNA precursors, and that this activity is restored by the fluoroquinolon, enoxacin, on the genetic background of ALS-causing mutations (TDP-43, FUS and SOD1, see FIGS. 2E-H), suggesting the global nature of the observed miRNA dysregulation in the presence of various disease causing mutants. The present inventors have further illustrated in an ALS mouse model that the deterioration in mouse neuromuscular function was slower under Enoxacin treatment as assayed by neurological score (FIG. 4B), hang-wire test (FIG. 4C) and automated cat-walk study (FIG. 4D). Thus, dysregulated microRNAs provide new mechanistic insight into ALS pathogenesis and a potential therapeutic lead. Furthermore, the miRNA expression profile can be used in the diagnosis of MNDs in general and ALS in particular.

The present inventors have further demonstrated that reduction in miRNA levels is a common molecular denominator for stress related disorders and involves the formation of stress graunules. Specifically, it was shown that miRNA processing is inhibited by cellular stress via impairment of the Dicer complex activity (FIGS. 7A-L). Furthermore, it was shown that assembly of stress granules is involved in miRNA processing (FIGS. 9A-F) and that assembly of stress granules is induced by ALS-causing proteins (FIGS. 8A-C). The effect of stress granules on miRNA processing involves various factors and proteins including stress granule components and Dicer co-factors (see further details in Examples 5-7 below). Taken together, these observations establish a novel miRNA pathway downstream of the stress response and offer novel therapeutic targets for stress related disorders.

Thus, according to one aspect of the invention there is provided a method of treating a cellular stress-related disease in a subject in need thereof, the method comprising administering to the subject a therapeutically effective amount of an agent capable of enhancing processing of a pre-miRNA, thereby treating the cellular stress-related disease in the subject.

According to a specific embodiment or an alternative aspect of the invention there is provided a method of treating a motor neuron disease (MND) in a subject in need thereof, the method comprising administering to the subject a therapeutically effective amount of the agent capable of enhancing processing of a pre-miRNA, thereby treating the motor neuron disease (MND) in the subject.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition (e.g., stress-related disease or an MND).

As used herein a "stress-related disease" refers to a medical condition which onset or progression depend on cellular stress.

As used herein, the terms "cellular stress" and "stress" may be interchangeably used and are directed to a situation in which in response to a less than optimal condition which impose on a cell pressure or demand, the cell acts by changing at least one of its normal function(s). Cells may respond to cellular stress in a variety of ways ranging from activation of intracellular pathways that promote survival to activating programmed cell death that eliminates a damaged cell. The initial response of the cell to a stress condition is directed in helping the cell defend against-, and recover from the condition induced by the stress. There are numerous types of stress and the response a cell may elicit to deal with the stress condition may depend on the type and level of the stress.

Exemplary stressful conditions that affect cells, include, but are not limited to: changes in temperature (for example, heat shock stress is induced by elevated temperatures, or extreme cold stress); metabolite stress, induced by, for example, shortage/access of various metabolites in the environment and/or in the cell; pathogen-induced stress in response, for example, to infection of the cell (e.g. viral infection); oxidative stress, induced by, for example, access of free radicals within the cell; toxic stress, induced by, for example, various toxins, drugs and/or chemicals entering the cell (e.g. chemotherapeutic agents, heavy metals, toxic chemicals, e.g. chemical stress such as sodium arsenite and pateamine A); irradiation stress, induced by various radiation sources (e.g. ionizing radiation, electromagnetic irradiation); endoplasmic reticulum (ER) stress, which can be caused by accumulation of unfolded protein aggregates (unfolded protein response, UPR); hypoxia, mechanical stress, hyperosmolarity stress.

According to one embodiment, the cellular stress is an ER/UPR stress.

ER stress relates to any internal or external cellular stimulus that compromises ER homeostasis by stressing the protein folding capacity of the ER. Cells typically cope with ER stress by activating an ER stress signaling network called the Unfolded Protein Response (UPR), which includes at least three components that counteract ER stress: stress gene expression, translational attenuation, and ER-associated protein degradation (ERAD).

Regardless of the type of stress, the cellular response typically includes formation of stress granules (SGs), i.e. the appearance of distinct protein- and RNA-aggregates in the cell cytoplasm. Stress granules are typically 100-200 nm in size, they are not surrounded by a membrane and are associated with the endoplasmatic reticulum. In stress granules, the stored RNA molecules are stalled in translation pre-initiation complexes and are not translated into proteins. Stress granules can be identified using markers typically expressed thereon (e.g. YB-1) as discussed in detail in Kedersha N. and Anderson P, Methods Enzymol. (2007) 431:61-81, incorporated herein by reference, or by identification of proteins typically involved in the formation of stress granules (e.g. eIF3, G3BP, HuR, TIA-1, PABP, as described in detail below).

A cell in regarded as being in stress if there is presence of stress granules, or if there is an elevation of at least 5%, 10%, 20%, 30%, 40%, 50% or more in stress granules in the cell as compared to another cell of the same species, type, developmental stage and growth conditions only not subjected to stress.

Examples of proteins involved in the formation of stress granules include, without being limited to, proteins involved in translation pre-initiation complex e.g. eIF2a, the small ribosomal subunit (40S), poly(A)-binding protein (PABP1), eIF3, eIF4E, eIF4G; RNA-binding proteins with roles in regulation of mRNA translation or stability e.g. Ago2, ELAV like RNA-binding protein (HuR), TIA-1 and its homolog TIAR, PACT, cytoplasmic polyadenylation element binding protein (CPEB), Ataxin-2 (ATXN2), GTPase activating protein (SH3 domain) binding protein (G3BP), Tristetraprolin (TTP), Pumilio, 50-to-30 exonuclease (Xrn1), fragile X mental retardation protein (FMRP) and its autosomal homolog FXR, DEAD box polypeptide 6 (DDX6/RCK), polysomal ribonuclease 1 (PMR1/PXDNL), Zipcode-binding protein 1 (ZBP1); splicing and other mRNA metabolism related proteins e.g. hnRNPA1, SMN, FUS, VCP, PRMT1, TDP-43, STAUFEN or Fasactivated serine/threonine kinase (FAST).

In general, the present invention concerns clinical applications on human beings, therefore, according to a specific embodiment, the cell is a human cell and the gene expression product described herein is a human gene.

As mentioned, cellular stress may be responsible for initiating or causing numerous conditions and diseases. Alternatively or additionally, the progression of a disease can be affected by cellular stress.

Cellular stress-related diseases include, but are not limited to, cancer, protein folding/misfolding disease, neurodegenerative diseases, metabolic diseases including diabetes mellitus (e.g. type II diabetes), diabetic vasculopathy, Wolcott-Rallison syndrome, ischemia/reperfusion injury, stroke, atherosclerosis, neoplasia, hypoxia, hypoglycemia, secondary degeneration after trauma, CNS intoxication, glaucoma, cataract, macular degeneration, autoimmune diseases (e.g. multiple sclerosis, systemic lupus erythematosis (SLE), autoimmune uveitis), graft versus host disease, graft rejection, arthritis, systemic inflammatory response syndrome (SIRS), inflammatory bowel disease (IBD), adult respiratory distress syndrome (ARDS), psoriasis, cardiovascular diseases (e.g. myocardial infarction), radiation disease, hyperthermia, liver disease (e.g. nonalcoholic fatty liver, alcoholic liver disease, fulminant toxic liver, hepatitis), kidney failure, infertility, bipolar disorder, viral infection (e.g. HCV, HBV), bacterial infection, fungal infection, transmissible spongiform encephalopathies (TSEs) including Creutzfeldt-Jakob disease. new variant Creutzfeldt-Jakob disease, Gerstmann-Sträussler-Scheinker syndrome, fatal familial insomnia, kuru disease and age-associated diseases.

Exemplary cancers include, without being limited to, colon adenocarcinoma, esophagus adenocarcinoma, liver hepatocellular carcinoma, squamous cell carcinoma, pancreas adenocarcinoma, islet cell tumor, rectum adenocarcinoma, gastrointestinal stromal tumor, stomach adenocarcinoma, adrenal cortical carcinoma, follicular carcinoma, papillary carcinoma, breast cancer, ductal carcinoma, lobular carcinoma, intraductal carcinoma, mucinous carcinoma, phyllodes tumor, Ewing's sarcoma, ovarian adenocarcinoma, endometrium adenocarcinoma, granulose cell tumor, mucinous cystadenocarcinoma, cervix adenocarcinoma, vulva squamous cell carcinoma, basal cell carcinoma, prostate adenocarcinoma, giant cell tumor of bone, bone osteosarcoma, larynx carcinoma, lung adenocarcinoma, kidney carcinoma, urinary bladder carcinoma, Wilm's tumor, or lymphoma.

Exemplary protein folding/misfolding diseases include, without being limited to, Alzheimer's disease, Parkinson's disease, lysososmal storage diseases (LSDs), amyotrophic lateral sclerosis (ALS), Creutzfeldt-Jakob disease, cystic fibrosis, bovine spongiform encephalopathy (BSE), light chain amyloidosis (AL), Huntington's disease, spinobulbar muscular atrophy (Kennedy disease), Machado-Joseph disease, dentatorubral-pallidoluysian atrophy (Haw River Syndrome), spinocerebellar ataxia, hypercholesteremia, retinitis pigmentosa, nephrogenic diabetes insipidus or glaucoma.

Exemplary myelinating cell-related diseases include, without being limited to, multiple sclerosis (MS), Charcot-Marie-Tooth disease (CMT), Pelizaeus-Merzbacher Disease (PMD), or Vanishing White Matter Disease (VWMD).

Exemplary neurodegenerative diseases include, without being limited to, Parkinson's disease, Multiple Sclerosis (MS), Amyotrophic Lateral Sclerosis (ALS), multi-system atrophy, Alzheimer's disease, stroke, Spinal-cerebellar ataxia, Huntington's disease, progressive supranuclear palsy, progressive supernuclear palsy, granulovacuolar disease, frontotemporal dementia, corticobasal degeneration, epilepsy, autoimmune encephalomyelitis, diabetic neuropathy, glaucomatous neuropathy, Pick's disease, Lewy Body disease, Creutzfeld-Jacob Disease (CJD), variant Creutzfeld-Jacob Disease, new variant Creutzfeld-Jacob Disease, or kuru disease.

According to a specific embodiment, the cellular stress-related disease comprises a neurodegenerative disease.

According to a specific embodiment, the disease is a motor neuron disease.

The phrase "motor neuron disease (MND)" as used herein, refers to a neurological disorder that selectively destroys motor neurons. As such, diseases such as Huntington's chorea are not classified as MNDs.

According to a further aspect of the invention, the subject suffers from Frontotemporal Dementia.

Examples of motor neuron diseases include, but are not limited to Amyotrophic Lateral Sclerosis (ALS), also known as Lou Gehrig's Disease, primary lateral sclerosis, progressive muscular atrophy, pseudobulbar palsy, progressive bulbar palsy, lower motor neuron disease and spinal muscular atrophy 1 (SMA1, Werdnig-Hoffmann Disease), Spinal Muscular Atrophy Type 2 (SMA2) and Spinal Muscular Atrophy Type 3 (SMA3, Kugelberg-Welander Disease) and Charcot-Marie-Tooth Disorders.

According to a specific embodiment the MND is amyotrophic lateral sclerosis (ALS).

According to further specific embodiments, the subject is affected with MND or ALS in which changes in RNA metabolism are reported or can be determined according to the present teachings. Examples of mutations associated with changes in RNA metabolism include, but are not limited to, mutations in TDP-43, FUS, SOD1, ANG and SETX, (Chen et al., 2004; Greenway et al., 2006; Kabashi et al., 2008; Sreedharan et al., 2008; Kwiatkowski et al., 2009; Lagier-Tourenne and Cleveland, 2009; Vance et al., 2009).

As used herein, the term "subject" or "subject in need thereof" refers to a mammal e.g., a human being of any gender or age (e.g., infant, child or adult) that has been diagnosed with MND or with another cellular stress-related disease, or is predisposed to MND or to another cellular stress-related disease. The disease (e.g., ALS) may be familial (inherited) or sporadic.

According to a further embodiment, the subject does not suffer from *Chlamydia* infection, especially when the treatment modality is enoxacin.

As used herein "an agent capable of enhancing processing of a pre-miRNA" refers to a molecule or a composition which upregulates or activates any part of the miRNA processing pathway. Typically, the agent upregulates or activates the pathway downstream to the pre-miRNA production. This is because the present inventors have shown that pre-miRs are normally formed and even upregulated in cellular stress related disorders (e.g. in ALS derived cells). The agent may be referred to as an "RNAi enhancer".

Following are some key components of the miRNA processing pathway, each of which can be upregulated or activated according to the teachings of the present invention.

Nuclear Processing

A single pri-miRNA may contain from one to six miRNA precursors. These hairpin loop structures are composed of about 70 nucleotides each. Each hairpin is flanked by sequences necessary for efficient processing. The double-stranded RNA structure of the hairpins in a pri-miRNA is recognized by a nuclear protein known as DiGeorge Syndrome Critical Region 8 (DGCR8 or "Pasha" in invertebrates), named for its association with DiGeorge Syndrome. DGCR8 associates with the enzyme Drosha, a protein that cuts RNA, to form the "Microprocessor" complex. In this complex, DGCR8 orients the catalytic RNase III domain of Drosha to liberate hairpins from pri-miRNAs by cleaving RNA about eleven nucleotides from the hairpin base (two helical RNA turns into the stem). The product resulting has a two-nucleotide overhang at its 3' end; it has 3' hydroxyl and 5' phosphate groups. It is often termed as a pre-miRNA (precursor-miRNA).

Nuclear Export pre-miRNA hairpins are exported from the nucleus in a process involving the nucleocytoplasmic shuttle Exportin-5. This protein, a member of the karyopherin family, recognizes a two-nucleotide overhang left by the RNase III enzyme Drosha at the 3' end of the pre-miRNA hairpin. Exportin-5-mediated transport to the cytoplasm is energy-dependent, using GTP bound to the Ran protein.

Cytoplasmic Processing

In cytoplasm, the pre-miRNA hairpin is cleaved by the RNase III enzyme Dicer. This endoribonuclease interacts with the 3' end of the hairpin and cuts away the loop joining the 3' and 5' arms, yielding an imperfect miRNA:miRNA* duplex about 22 nucleotides in length. Overall hairpin length and loop size influence the efficiency of Dicer processing, and the imperfect nature of the miRNA:miRNA* pairing also affects cleavage. Although either strand of the duplex may potentially act as a functional miRNA, only one strand is usually incorporated into the RNA-induced silencing complex (RISC) where the miRNA and its mRNA target interact.

It should be noted that for efficient pre-miRNA processing, partners of Dicer are required. These include Argonaute (AGO), protein kinase interferon-inducible double-stranded RNA dependent activator (PACT) and TAR RNA-binding protein (TRBP). Dicer and its co-factors load the mature miRNA onto AGO in the RNA-induced silencing complex (RISC), providing sequence-specific silencing activity. Moreover, Argonaute RISC catalytic component 2 (AGO2) has dual functions in the processing of miRNA precursors and in target silencing. First, AGO2 functions as a Dicer co-factor in pre-miRNA processing, as part of the RISC-loading complex. Next, AGO2 is loaded with a guide miRNA strand, making an active RISC (Chendrimada et al, 2005; Gregory et al, 2005). Once programmed with a particular miRNA sequence, RISC acts as an effector that facilitates miRNA-dependent mRNA silencing. Therefore, miRNA processing and target-RNA repression are physically and functionally interlinked by sharing many common protein components.

Additional factors, such as heat-shock protein 90 (Hsp90), co-chaperone p23 and eukaryotic translation initiation factor 3 subunit L (eIF3L) which have a role in regulating the interactions of Dicer with Ago2, may also be involved in miRNA processing [Pare et al. (2013) Mol Biol Cell 24(15): 2303-2310].

miRNA biogenesis is also affected by RNA tailing, RNA editing, RNA methylation and modulation of RNA stability. For a more detailed explanation see Minju H. and V. Narry Kim, Nature Reviews (2014) 15: 509-524, incorporated herein by reference).

RNA tailing (untemplated nucleotidyl addition to the 3' end of RNA) modifies pre-miRNA and mature miRNA including by uridylation of the let-7 precursor family members or other miRNAs via LIN28A/LIN28B activity. Specifically, LIN28A and its paralogue LIN28B bind to the terminal loop of pri-let-7 and pre-let-7 and hamper with Drosha and Dicer processing, respectively. The LIN28 proteins also recruit the terminal uridylyl transferases TUT4 (known as ZCCHC11) or TUT7 (known as ZCCHC6) to induce oligouridylation of pre-let-7. An oligo-U tail typically blocks Dicer processing and facilitates miRNA decay. The 3'-5' exonuclease that recognizes the U tail is DIS3L2. In cells that do not express LIN28, terminal uridylyl transferases (e.g. TUT7, TUT4 or TUT2) induce monouridylation at the 3' end of group II pre-let-7 miRNAs and increase let-7 biogenesis. Thus, LIN28 acts as a molecular switch that converts TUT4 and TUT7 from biogenesis factors into negative regulators of miRNAs such as let-7 miRNAs.

Adenylation is another type of RNA tailing and occurs mainly after Dicer processing. Adenylation may stabilize or degrade the miRNA by endogenous proteins or viruses such as poxvirus-encoded VP55 (also known as PAPL). Hence, the consequences of miRNA adenylation may depend on the context.

RNA editing involves the conversion of adenosine to inosine, which is catalysed by adenosine deaminases (ADARs). RNA editing has been observed in some pri-miRNAs (e.g. miR-142, miR-151). Editing occurs in the stem region of the pri-miRNAs and makes the pri-miRNAs poor substrates for Drosha or Dicer activity, and thus limits processing thereof.

RNA methylation, including e.g. by the human RNA methyltransferase BCDIN3D, was shown to O-methylate the 5' monophosphate of pre-miRNAs (e.g. pre-mir-145 and pre-mir-23b). As human Dicer interacts with the 5'-terminal phosphate, this modification interferes with Dicer-mediated processing.

The abundance of some miRNAs is regulated at the RNA stability level. Pre-miRNAs, including e.g. miR-146a and miR-135b, are cleavage at the terminal loop of pre-miRNA by the mammalian endoribonuclease MCP-induced protein 1 (MCPIP1 also known as ZC3H12A) or by the Ser/Thr protein kinase/endoribonuclease IRE1α. IRE1α is induced by ER stress and cleaves selected pre-miRNAs (e.g. pre-mir-17, pre-mir-34a, pre-mir-96 or pre-mir-125b). This leads to translational derepression of the pro-apoptotic caspase 2 (for a detailed explanation see Minju H. and V. Narry Kim, Nature Reviews (2014) supra, incorporated herein by reference).

Active degradation of mature miRNA by small-RNA-degrading nucleases including e.g. the 5'-3' exoribonucleases XRN-1 and XRN-2, and by the human polynucleotide phosphorylase PNPase old-35 (known as PNPT1), an interferon-inducible 3"-5" exonuclease, has been previously described (see Minju H. and V. Narry Kim, Nature Reviews (2014) supra, incorporated herein by reference).

Thus, according to embodiments of the invention, the agent capable of enhancing processing of pre-miRNA is selected from the group consisting of a nuclear processing enhancer, a nuclear export enhancer and a cytoplasmic processing enhancer.

According to specific embodiments of the invention, the agent upregulates by at least 5%, 10%, 20%, 30%, 40%, 50%, 60%, 70%, 80% (e.g., 50% or more) or even more, processing of the pre-miRNA as compared to pre-miRNA processing in an untreated sample of a MND affected subject (e.g., of cells carrying MND causing mutations).

Methods of assessing miRNA processing are well known in the art. For example, analyzing the levels of total miRNA as compared to pre-miRNA can be used as a strong indicator of miRNA processing and is exemplified in the Examples section which follows.

According to a specific embodiment, the agent is selected from the group consisting of a nuclear processing enhancer, a nuclear export enhancer and a cytoplasmic processing enhancer.

According to a further embodiment the cytoplasmic processing enhancer comprises a Dicer enhancer (i.e., upregulates or activates Dicer activity).

Ge Shan et al. 2008 Nature Biotechnology 26(8):933 teach a method of identifying modulators of the RNAi pathway. Such methods can be implemented in order to identify further agents which can be used along with the present teachings.

U.S. 20090306035 teaches quinolones as RNAi enhancers and is hereby incorporated by reference in its entirety.

Quinolone (or quinolone) compounds form a class of broad-spectrum antibiotics. Quinolones are believed to act by inhibiting the bacterial DNA gyrase and/or the topoisomerase IV enzyme. In this way, quinolones inhibit DNA replication and act bacteriocidically. As such, quinolones are considered chemotherapeutic agents as opposed to a true antibiotic, because they prevent replication of the bacterial cell by interfering with the genetic replication of the bacterium. Representative, non-limiting quinolone antibiotics are provided in Table 1 of U.S. 20090306035 and some are provided infra.

The pharmacophore common to quinolone antibiotics is provided in Formula (a):

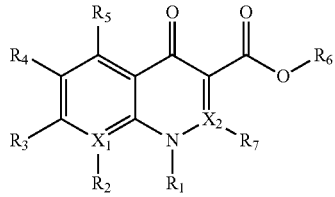

wherein:

$X_1$ and $X_2$ are each independently carbon or nitrogen;

$R_1$ is selected from the group consisting of H, alkyl, substituted alkyl, alkylamino, cycloalkyl, substituted cycloalkyl, aryl, and substituted aryl;

$R_2$ can be present or absent and when present is selected from the group consisting of H, halo, alkyl, substituted alkyl, and alkoxyl; or $R_1$ and $R_2$ together form a portion of a 4- to 6-member heterocyclic ring structure, wherein the 4- to 6-member heterocyclic ring structure comprises atoms selected from the group consisting of carbon, nitrogen, oxygen, sulfur, and combinations thereof;

$R_3$ is selected from the group consisting of H, halo, alkyl, substituted alkyl, aryl, substituted aryl, cycloalkyl, substituted cycloalkyl, cycloheteroalkyl, substituted cycloheteroalkyl, heteroaryl, and substituted heteroaryl;

$R_4$ is halo;

$R_5$ is selected from the group consisting of H, alkyl, substituted alkyl, amino, alkoxyl, hydroxyl, and halo;

$R_6$ is selected from the group consisting of H, alkyl, and substituted alkyl;

$R_7$ can be present or absent and when present is selected from the group consisting of H, alkyl, substituted alkyl, amino, alkoxyl, hydroxyl, and halo; or $R_1$ and $R_7$ together form a portion of a 4- to 6-member heterocyclic ring structure, wherein the 4- to 6-member heterocyclic ring structure comprises atoms selected from the group consisting of carbon, nitrogen, oxygen, sulfur, and combinations thereof; or a pharmaceutically or cosmetically acceptable salt thereof.

In some embodiments, the quinolone compound of Formula (a) is selected from the group consisting of enoxacin, ciprofloxacin, and ofloxacin, the structures of which are provided in Scheme I.

Scheme I. Chemical Structures of Enoxacin, ciprofloxacin, and ofloxacin

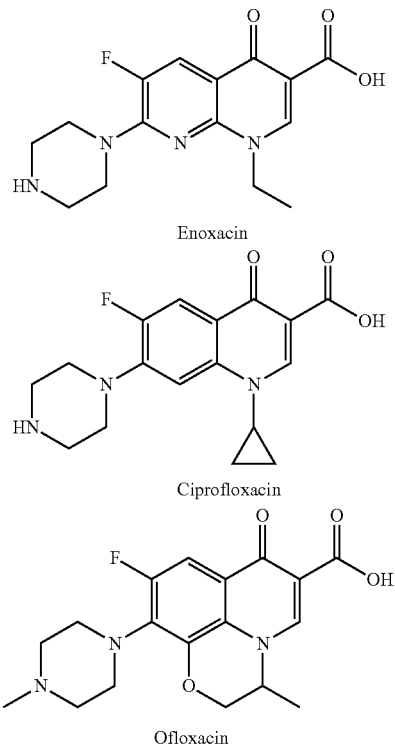

Enoxacin

Ciprofloxacin

Ofloxacin

Enoxacin, ciprofloxacin, and ofloxacin generally are classified as "second generation" quinolones. Second generation quinolones also include, but are not limited to, fleroxacin, levofloxacin, lomefloxacin, nadifloxacin, norfloxacin, pefloxacin, rufloxacin, and tosufloxacin, the chemical structures of which are provided in Scheme II.

Scheme II. Chemical Structures of Second Generation Quinolones

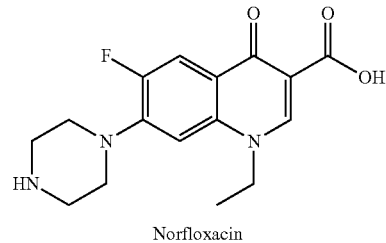

Norfloxacin

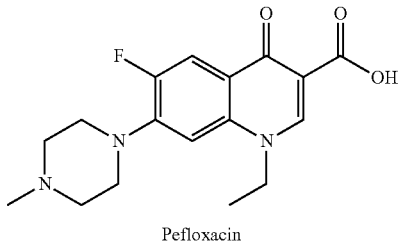
Pefloxacin
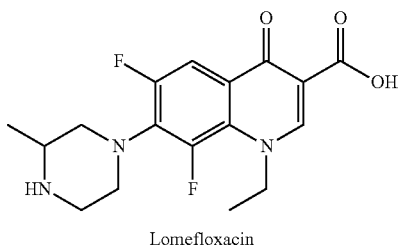
Lomefloxacin
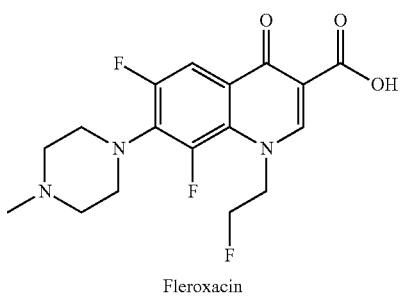
Fleroxacin
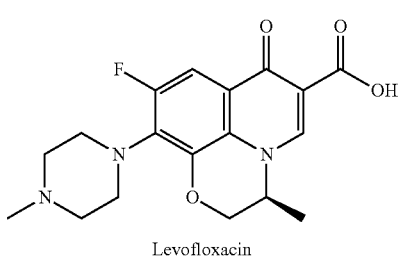
Levofloxacin
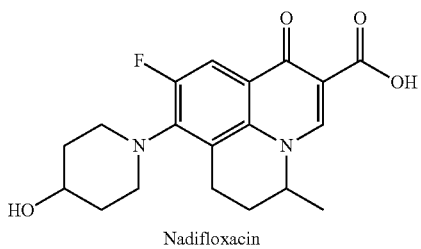
Nadifloxacin
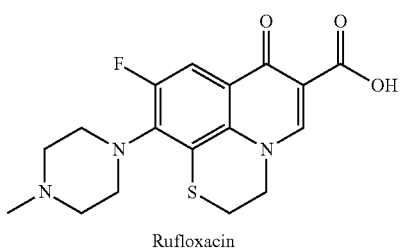
Rufloxacin
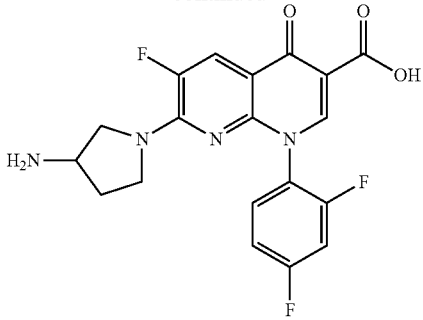
Tosufloxacin
U.S. Patent Application Number 20120071539 teaches further enhancers of RNAi.
(a) triprolidine, derivatives, and analogs thereof (formula b):
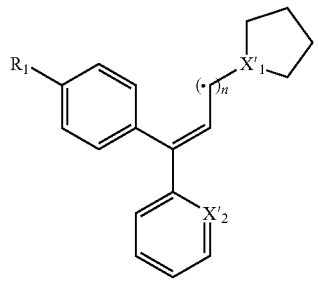
(b) dihydroptaeroxylin, derivatives, and analogs thereof (formula c):
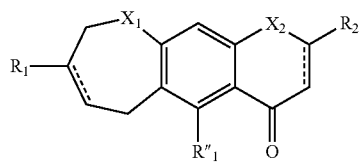
(c) fusidic acid, derivatives, and analogs thereof (formula d):
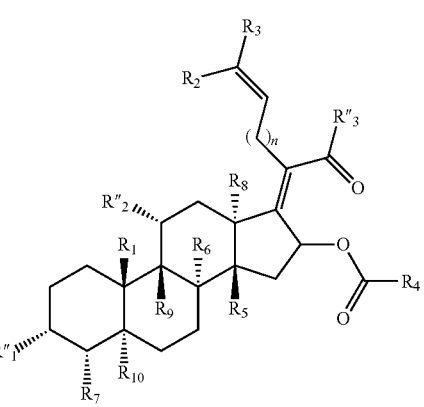

(d) fenbufen, derivatives, and analogs thereof (formula e):

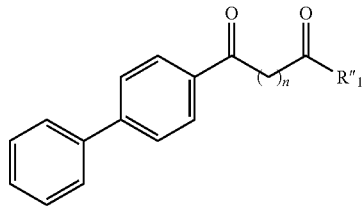

(e) 3-beta-hydroxydeoxyodihydrodeoxygedunin, derivatives, and analogs thereof (formula f):

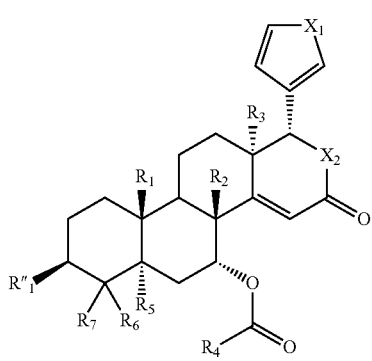

(f) deferoxamine, derivatives, and analogs thereof (formula g):

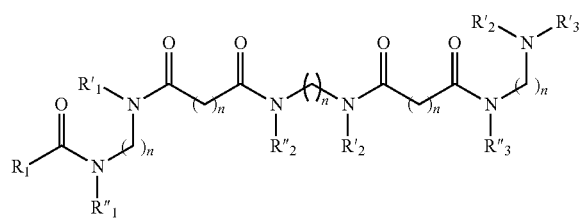

(g) thioguanine, derivatives, and analogs thereof (formula h):

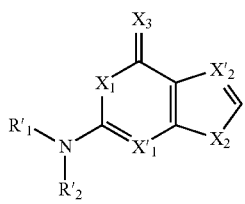

(h) 2-aminomethyl-1,4-benzodioxane, derivatives, and analogs thereof (formula i):

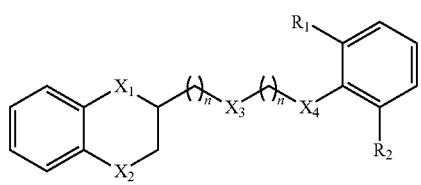

(i) 3-alpha-hydroxy-3-deoxyangolensic acid methyl ester, derivatives, and analogs thereof (formula j):

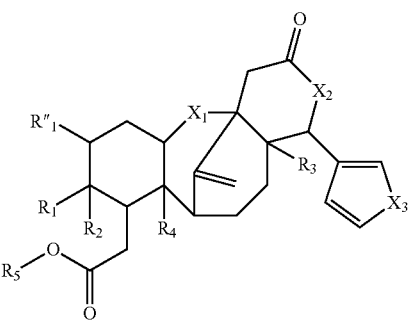

(j) lunarine, derivatives, and analogs thereof (formula k): and

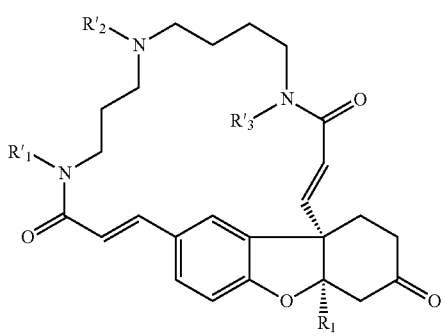

(k) bromocriptine, derivatives, and analogs thereof (formula l):

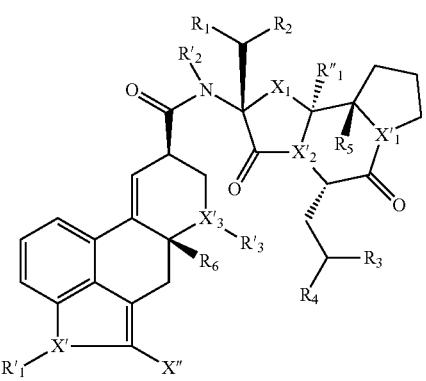

each n is independently an integer from 1 to 20;
a dashed line in a cyclic ring structure represents a bond that can be either present or absent in the ring;
each $R_1$, $R_2$, $R_3$, $R_4$, $R_5$, $R_6$, $R_7$, $R_8$, $R_9$, and $R_{10}$ is independently selected from the group consisting of H, alkyl, substituted alkyl, cycloalkyl, substituted cycloalkyl, aryl, and substituted aryl;
each $R'_1$, $R'_2$, and $R'_3$ is independently selected from the group consisting of H, alkyl, substituted alkyl, cycloalkyl, substituted cycloalkyl, aryl, substituted aryl, hydroxyl, and alkoxyl;
each $R''_1$, $R''_2$, and $R''_3$ is independently selected from the group consisting of —$OR_{11}$ and —O(C.dbd.O)—$R_{12}$, wherein $R_{11}$ and $R_{12}$ are selected from the group consisting of H, alkyl, substituted alkyl, cycloalkyl, substituted cycloalkyl, aryl, and substituted aryl;

each $X_1$, $X_2$, $X_3$, and $X_4$ is independently selected from the group consisting of $CH_2$, O, S, and $NR'_4$, wherein $R'_4$ is selected from the group consisting of H, alkyl, substituted alkyl, cycloalkyl, substituted cycloalkyl, aryl, substituted aryl, hydroxyl, and alkoxyl;

each $X'_1$, $X'_2$, and $X'_3$ is independently N or CH; and each X" is independently halogen; and pharmaceutically and cosmetically acceptable salts thereof.

In some embodiments, the RNAi enhancer is selected from the group consisting of triprolidine, dihydropaeroxylin, fusidic acid, fenbufen, 3-beta-hydroxydeoxodihydrodeoxygedunin, deferoxamine, thioguanin, 2-aminomethyl-1,4-benzodioxane, 3-alpha-hydroxy-3-deoxyangloensic acid methyl ester, lunarine, bromocriptine, and pharmaceutically and cosmetically acceptable salts thereof.

According to a specific embodiment, the RNAi enhancer is enoxacin.

Enoxacin is sold under the following trade names Almitil, Bactidan, Bactidron, Comprecin, Enoksetin, Enoxen, Enroxil, Enoxin, Enoxor, Flumark, Penetrex, Gyramid, Vinone. The compound is an oral broad-spectrum fluoroquinolone antibacterial agent used in the treatment of urinary tract infections and gonorrhea.

While the following terms are believed to be well understood by one of ordinary skill in the art, the following definitions are set forth to facilitate explanation of the presently disclosed subject matter.

When the term "independently selected" is used, the substituents being referred to (e.g., R groups, such as groups $R_1$, $R_2$, and the like, or groups $X_1$ and $X_2$), can be identical or different. For example, both $R_1$ and $R_2$ can be substituted alkyls, or $R_1$ can be hydrogen and $R_2$ can be a substituted alkyl, and the like.

A named "R" or "X" group will generally have the structure that is recognized in the art as corresponding to a group having that name, unless specified otherwise herein. For the purposes of illustration, certain representative "R" and "X" groups as set forth above are defined below. These definitions are intended to supplement and illustrate, not preclude, the definitions that would be apparent to one of ordinary skill in the art upon review of the present disclosure.

As used herein the term "alkyl" refers to C1-20 inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and alkenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C1-8 alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxy, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an allyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, such as a 3- to 7-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a straight or branched hydrocarbon of a designed number of carbon atoms containing at least one carbon-carbon double bond. Examples of "alkenyl" include vinyl, allyl, 2-methyl-3-heptene, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described.

An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to an aromatic ring system, such as, but not limited to a 5- or 6-member ring system, including one or more heteroatoms, which can be the same or different, and are selected from the group consisting of N, O and S. The heteroaryl ring can be fused or otherwise attached to one or more heteroaryl rings, aromatic or non-aromatic hydrocarbon rings, or heterocycloalkyl rings. Representative heteroaryl ring systems include, but are not limited to, pyridyl, pyrimidyl, pyrrolyl, pyrazolyl, azolyl, oxazolyl, isoxazolyl, oxadiazolyl, thiazolyl, isothiazolyl, imidazolyl, furanyl, thienyl, quinolinyl, isoquinolinyl, indolinyl, indolyl, benzothienyl, benzothiazolyl, enzofuranyl, benzimidazolyl, benzisoxazolyl, benzopyrazolyl, triazolyl, tetrazolyl, and the like.

A structure represented generally by the formula, wherein the ring structure can be aromatic or non-aromatic:

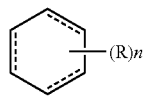

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure above where n is 0 to 2 would comprise compound groups including, but not limited to:

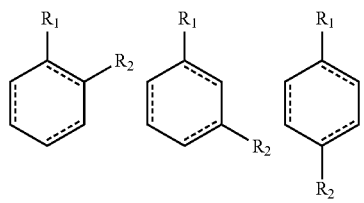

and the like.

A dashed line representing a bond in a cyclic ring structure indicates that the bond can be either present or absent in the ring. That is a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" refers to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "alkyl-thio-alkyl" as used herein refers to an alkyl-S-alkyl thioether, for example, a methylthiomethyl or a methylthioethyl group.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl. "Aryloxycarbonyl" refers to an aryl-O—CO— group. Exemplary aryloxycarbonyl groups include phenoxy- and naphthoxy-carbonyl. "Aralkoxycarbonyl" refers to an aralkyl-O—CO— group. An exemplary aralkoxycarbonyl group is benzyloxycarbonyl.

"Carbamoyl" refers to an H2N—CO— group. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted allyl as previously described.

"Acyloxyl" refers to an acyl-O— group wherein acyl is as previously described.

The term "amino" refers to the —NH2 group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylamino" refers to an —NHR group wherein R is an alkyl group and/or a substituted alkyl group as previously described. Exemplary alkylamino groups include methylamino, ethylamino, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

In some embodiments, the RNAi enhancer comprises a protein which is involved in processing of a pre-miRNA.

In some embodiments, the RNAi enhancer comprises the protein Dicer (e.g. Dicer1).

In some embodiments, the RNAi enhancer comprises a double-stranded RNA (dsRNA)-binding protein, e.g. the protein activator of PKR (PACT) and/or the trans-activation response RNA-binding protein (TRBP), or a member of the Argonaute (Ago) protein family, or hyperactive mutant versions thereof.

In some embodiments, the RNAi enhancer comprises a poly(C)-binding protein [e.g. poly(C)-binding protein 2, as taught for example by Li Y. et al., Cell Metab. 2012 Jun. 6; 15(6):895-904].

According to a specific embodiment, the RNAi enhancer comprises overexpression of any of the above mentioned proteins.

The examples section which follows illustrates that stress granules effect miRNA processing in a process involving various factors and proteins including stress granule components and Dicer co-factors (see further details in Examples 5-7 below).

Thus, the method of some embodiments of the invention further comprises administering to the subject a therapeutically effective amount of an agent capable of decreasing cellular stress.

According to specific embodiments of the invention, the agent decreases cellular stress by at least about 5%, 10%, 20%, 30%, 40%, 50%, 60%, 70%, 80%, 90% or 100% as compared to an untreated subject (e.g., a subject not receiving an agent capable of decreasing cellular stress).

Determining cellular stress can be carried out using any method known in the art, as for example, by measuring expression of RNA markers associated with stress (e.g. with ER-stress: ASNS, ATF4, CHOP and GRP78) by for example by northern blotting or RT-qPCR, by measuring cell viability (e.g. by Hoechst staining) or by identification of proteins typically involved in the formation of stress granules (e.g. eIF3, G3BP, HuR, TIA-1, PABP) by e.g. specific antibodies.

Thus, according to one embodiment, the agent capable of decreasing cellular stress is capable of inhibiting formation and/or enhancing disaggregation of stress granules.

The term "inhibiting formation" of a stress granule refers to the process of preventing formation of stress granules in a cell by at least about 5%, 10%, 20%, 30%, 40%, 50%, 60%, 70%, 80%, 90% or 100% as compared to a cell of the same species, type, developmental stage and/or growth conditions not treated with the agent.

The term "enhancing disaggregation" of a stress granule refers to the process of deconstructing or dissolution of stress granules in a cell by at least about 5%, 10%, 20%, 30%, 40%, 50%, 60%, 70%, 80%, 90% or 100% as compared to a cell of the same species, type, developmental stage and/or growth conditions not treated with the agent.

According to one embodiment, an agent capable of decreasing cellular stress is selected to target a factor associated with the formation or disaggregation of stress granules.

As used herein, the term "to target" refers to upregulate or downregulate the expression or function of a gene or an expression product thereof (e.g., a factor associated with the formation or disaggregation of stress granules). According to a specific embodiment, the down-regulating is effected by direct interaction with the nucleic acid encoding the polypeptide product (e.g., by an RNA silencing agent) or the polypeptide itself. According to an alternative or an additional embodiment, downregulating is effected by direct targeting an effector or an activator of the target.

A factor which may be targeted in accordance with the present teachings includes, but is not limited to, eIF2A, Eukaryotic translation initiation factor 2-alpha kinases including protein kinase RNA-like endoplasmic reticulum kinase (PERK), heme-regulated eIF2α kinase (HRI), Protein kinase RNA-activated (PKR), general control nonderepressible 2 (GCN2); Argonaute (Ago, e.g. Ago1, Ago2, Ago3, Ago4), protein activator of the double-stranded RNA-activated protein kinase (PACT), TIA-1 and its homolog TIAR, ELAV like RNA-binding protein (HuR), the small ribosomal subunit (40S), poly(A)-binding protein (PABP1); Eukaryotic translation initiation factors including eIF3, eIF4E, eIF4G, eIF5, cytoplasmic polyadenylation element binding protein (CPEB), Ataxin-2 (ATXN2), GTPase activating protein (SH3 domain) binding protein (G3BP), Tristetraprolin (TTP), Pumilio, 5'-to-3' exonuclease (Xrn1), fragile X mental retardation protein (FMRP) and its autosomal homolog FXR, DEAD box polypeptide 6 (DDX6/RCK), polysomal ribonuclease 1 (PMR1/PXDNL), Zipcode-binding protein 1 (ZBP1), heterogeneous nuclear ribonucleoprotein A1 (hn-RNPA1), SMN, FUS (TLS), VCP, PRMT1, TDP-43 (TAR-DBP), STAUFEN or Fas-activated serine/threonine kinase (FAST).

The agent capable of decreasing cellular stress may be selected for upregulating or downregulating the factor associated with the stress granules, a decision which is in the capacity of one of ordinary skill in the art.

Downregulation of a factor associated with the stress granules can be effected on the genomic and/or the transcript level using a variety of molecules which interfere with transcription and/or translation [e.g., RNA silencing agents (e.g., antisense, siRNA, shRNA, micro-RNA), Ribozyme, DNAzyme and a CRISPR system (e.g. CRISPR/Cas)], or on the protein level using e.g., peptides or small molecules inhibitors.

Following is a list of agents capable of downregulating expression level and/or activity of a factor associated with the stress granules.

Thus, for example, downregulation of a factor associated with the stress granules can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., a factor associated with the stress granules) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82% or 81% global homology to the target gene.

RNA interference refers to the process of sequence-specific post-transcriptional gene silencing in animals mediated by short interfering RNAs (siRNAs). The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the mRNA sequence of a factor associated with the stress granules is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

It will be appreciated from the description provided herein above, that contacting a cell under a stress condition or in risk thereto with a miRNA may be affected in a number of ways:
1. Transiently transfecting the cells with a mature double stranded miRNA.
2. Stably, or transiently transfecting the cells with an expression vector which encodes the mature miRNA.
3. Stably, or transiently transfecting the cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 5-10 or variants thereof.
4. Stably, or transiently transfecting the cells with an expression vector which encodes the pri-miRNA The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof.

Another agent capable of downregulating a factor associated with the stress granules is a DNAzyme molecule capable of specifically cleaving an mRNA transcript or DNA sequence of the factor associated with the stress granules. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www(dot)asgt(dot)org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a factor associated with the stress granules can also be effected by using an antisense polynucleotide capable of specifically hybridizing with an mRNA transcript encoding the factor associated with the stress granules.

Design of antisense molecules which can be used to efficiently downregulate a factor associated with the stress granules must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

Another agent capable of downregulating a factor associated with the stress granules is a ribozyme molecule capable of specifically cleaving an mRNA transcript encoding a factor associated with the stress granules. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating a factor associated with the stress granules is a RNA-guided endonuclease technology e.g. CRISPR system.

As used herein, the term "CRISPR system" also known as Clustered Regularly Interspaced Short Palindromic Repeats refers collectively to transcripts and other elements involved in the expression of or directing the activity of CRISPR-associated genes, including sequences encoding a Cas gene (e.g. CRISPR-associated endonuclease 9), a tracr (trans-activating CRISPR) sequence (e.g. tracrRNA or an active partial tracrRNA), a tracr-mate sequence (encompassing a "direct repeat" and a tracrRNA-processed partial direct repeat) or a guide sequence (also referred to as a "spacer") including but not limited to a crRNA sequence or a sgRNA sequence (i.e. single guide RNA).

In some embodiments, one or more elements of a CRISPR system is derived from a type I, type II, or type III CRISPR system. In some embodiments, one or more elements of a CRISPR system (e.g. Cas) is derived from a particular organism comprising an endogenous CRISPR system, such as Streptococcus pyogenes, Neisseria meningitides, Streptococcus thermophilus or Treponema denticola.

In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence (i.e. guide RNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. Thus, according to some embodiments, global homology to the target sequence may be of 50%, 60%, 70%, 75%, 80%, 85%, 90%, 95% or 99%. A target sequence may comprise any polynucleotide, such as DNA or RNA polynucleotides. In some embodiments, a target sequence is located in the nucleus or cytoplasm of a cell.

Thus, the CRISPR system comprises two distinct components, a guide RNA (gRNA) that hybridizes with the target sequence, and a nuclease (e.g. Type-II Cas9 protein), wherein the gRNA targets the target sequence and the nuclease (e.g. Cas9 protein) cleaves the target sequence or silences target genes. The guide RNA may comprise a combination of an endogenous bacterial crRNA and tracrRNA, i.e. the gRNA combines the targeting specificity of the crRNA with the scaffolding properties of the tracrRNA (required for Cas9 binding). Alternatively, the guide RNA may comprise a single guide RNA (sgRNA) capable of directly binding Cas.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. This results in disruption of the gene of interest (i.e. target sequence) e.g. via insertions or deletions.

According to one embodiment, the Cas protein (e.g. Cas9) has no nuclease activity (i.e. is catalytically inactive) and is said to be 'dead' (dCas9). Catalytically inactive Cas9 protein can be used in accordance with the present teachings to bind to DNA (based on guide RNA specificity), this typically results in blockage of RNA polymerase binding or elongation, leading to dramatic suppression of transcription. Thus, dCas9 can be used for transcription repression.

As mentioned, a tracrRNA sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracrRNA sequence to all or a portion of a tracr mate sequence that is operably linked to the guide sequence (e.g. crRNA).

In some embodiments, the tracr sequence has sufficient complementarity to a tracr mate sequence to hybridize and participate in formation of a CRISPR complex. As with the target sequence, a complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned.

Introducing CRISPR/Cas into a cell may be effected using one or more vectors driving expression of one or more elements of a CRISPR system such that expression of the elements of the CRISPR system direct formation of a CRISPR complex at one or more target sites. For example, a Cas enzyme, a guide sequence linked to a tracr-mate sequence, and a tracrRNA sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. A single promoter may drive expression of a transcript encoding a CRISPR enzyme and one or more of the guide sequence, tracr mate sequence (optionally operably linked to the guide sequence), and a tracrRNA sequence embedded within one or more intron sequences (e.g. each in a different intron, two or more in at least one intron, or all in a single intron).

Another agent capable of downregulating a factor associated with the stress granules would be any molecule which binds to and/or cleaves the factor associated with the stress granules. Such molecules can be an antagonists, or an inhibitory peptide.

It will be appreciated that a non-functional analogue of at least a catalytic or binding portion of factor associated with the stress granules can be also used as an agent which downregulates a factor associated with the stress granules.

Another agent which can be used along with some embodiments of the invention to downregulate factor associated with the stress granules is a molecule which prevents activation or substrate binding.

According to a specific embodiment, the agent capable of decreasing cellular stress comprises a cycloheximide, a mithramycin A (also known as Plicamycin; trade name Mithracin), a parthenolide, a mycophenolic acid [also known as mycophenolate mofetil, marketed under the trade names CellCept (Roche) or Myfortic (Novartis)], a sodium phenylbutyrate [marketed under the trade names: Buphenyl (Ucyclyd Pharma, Hunt Valley, USA), Ammonaps (Swedish Orphan International, Sweden), or triButyrate (Fyrlklövern Scandinavia)], a salubrinal, a GSK2606414, a Geldanamycin or a Geldanamycin analogue (e.g. 17-AAG or 17-DMAG).

According to a specific embodiment, the agent capable of decreasing cellular stress is capable of inhibiting endoplasmic reticulum (ER) stress. An exemplary agent capable of decreasing ER stress includes, without being limited to, sodium phenylbutyrate [marketed under the trade names: Buphenyl (Ucyclyd Pharma, Hunt Valley, USA), Ammonaps (Swedish Orphan International, Sweden), or triButyrate (Fyrlklövern Scandinavia)] or a salubrinal.

Additionally or alternatively, inhibiting formation and/or enhancing disaggregation of stress granules in a cell may take place by removal of the stress condition.

As mentioned above, the agent capable of decreasing cellular stress may be selected to upregulate a factor associated with disaggregation or prevention of formation of the stress granules.

Upregulation of a factor associated with the stress granules can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like).

Following is a list of agents capable of upregulating the expression level and/or activity of a factor associated with the stress granules. Such agents can also be used (when specifically designed), to upregulate a factor which enhances processing a pre-miRNA, for example, Dicer (e.g. Dicer1), PACT, TRBP, Ago (e.g. Ago2), heat-shock protein 90 (Hsp90), co-chaperone p23, eukaryotic translation initiation factor 3 (eIF3), eukaryotic translation initiation factor 5A (eIF5a), eukaryotic translation initiation factor 2, subunit 1 alpha (eIF2S1) and/or poly(C)-binding protein 2 (PCBP2) or poly(C)-binding protein 1 (PCBP1).

An agent capable of upregulating expression of a factor associated with the stress granules may be an exogenous polynucleotide sequence designed and constructed to express at least a functional portion of the factor associated with the stress granules. Accordingly, the exogenous polynucleotide sequence may be a DNA or RNA sequence encoding a molecule of a factor associated with disaggregation or prevention of formation of the stress granules.

To express exogenous factors (e.g. proteins) in mammalian cells, a polynucleotide sequence encoding the factor (e.g. protein) is preferably ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

It will be appreciated that the nucleic acid construct of some embodiments of the invention can also utilize homologues which exhibit the desired activity (i.e., association with stress granules). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the sequence of the specific factor, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

Various methods can be used to introduce the expression vector of the present invention into the patient's cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 1986; 4:504-512] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

It will be appreciated that any of the gene therapy techniques and RNA silencing techniques can be used in in vivo or ex vivo settings (the latter being effected for example by modifying the patient's cells with the agents described herein ex vivo and administering the cells back to the subject). Alternatively allogeneic settings can be used.

An agent capable of upregulating a factor associated with the stress granules may also be any compound which is capable of increasing the transcription and/or translation of an endogenous DNA or mRNA encoding the factor associated with the stress granules and thus increasing endogenous activity thereof.

An agent capable of upregulating a factor associated with the stress granules may also be an exogenous polypeptide including at least a functional portion (as described hereinabove) of the factor associated with the stress granules.

Upregulation of the factor associated with the stress granules can be also achieved by introducing at least one substrate thereof. Non-limiting examples of such agents include over-expression of phosphomimetic serine of eIF2a or over-expression of Tia1.

As mentioned above, the methods of the present invention may be used for the treatment of ALS.

According to one embodiment, the method comprises administering to the subject a therapeutically effective amount of an agent capable of enhancing processing of a pre-miRNA and an anti-ALS agent, thereby treating the ALS in the subject.

According to another embodiment, the method further comprises administering to the subject an agent capable of decreasing cellular stress.

Thus, any of the above described agents capable of decreasing cellular stress may be selected to upregulate or downregulate a factor associated with disaggregation or prevention of formation of the stress granules (e.g. eIF2A, PERK, HRI, PKR, GCN2, Ago, e.g. Ago2, PACT, TIA-1 and its homolog TIAR, HuR, 40S, PABP1, eIF3, eIF4E, eIF4G, CPEB, ATXN2, G3BP, TTP, Pumilio, Xrn1, FMRP, FXR, DDX6/RCK, PMR1/PXDNL, ZBP1, hnRNPA1, SMN, FUS, VCP, PRMT1, TDP-43, STAUFEN or FAST).

Any anti-ALS agent capable of alleviating, treating or slowing ALS disease progression may be used in accordance with the present teachings.

An exemplary anti-ALS agent which may be used in accordance with the present teachings is Riluzole (e.g. Rilutek®).

According to a specific embodiment, the method comprises administering to the subject a quinolone (e.g. enoxacin) and an anti-ALS agent (e.g. Riluzole).

It will be appreciated that when administering more than one agent to the subject, the agents may be administered concomitantly or at separate times (e.g. within minutes, hours, days, weeks or months of each other).

The agents of some embodiments of the invention can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Notably, small molecules such as Enoxacin are known to be able to cross the blood brain barrier without further chemical modifications.

Alternately, one may administer the pharmaceutical composition in a local rather than systemic manner, for example, via injection of the pharmaceutical composition directly into a tissue region of a patient (e.g., brain or spinal cord).

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

The pharmaceutical composition can be for chronic use (e.g., oral chronic).

Alternatively, the pharmaceutical composition can be for acute use.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the agent) effective to prevent, alleviate or ameliorate symptoms of a disorder (e.g., cellular stress-related disease, MND e.g., ALS) or prolong the survival of the subject being treated.

According to one embodiment, the therapeutically effective amount of the agent capable of decreasing cellular stress is reduced as compared to an effective amount thereof when administered in a therapeutic regimen devoid of the agent capable of enhancing processing of a pre-miRNA. This may be a result of a synergistic effect between the agent capable of decreasing cellular stress and the agent capable of processing the pre-miRNA.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Animal models of amyotrophic lateral sclerosis (ALS) provide a unique opportunity to study this incurable and fatal human disease both clinically and pathologically. Nonetheless, postmortem ALS tissue remains the "gold standard" against which pathologic findings in animal models must be compared. Four natural disease models have been most extensively studied, including three mouse models: motor neuron degeneration (Mnd), progressive motor neuronopathy (pmn), wobbler, and one canine model: hereditary canine spinal muscular atrophy (HCSMA). The wobbler mouse has been the most extensively studied of these models with analyses of clinical, pathological (perikaryon, axon, muscle), and biochemical features. Experimentally induced ALS animal models have allowed controlled testing of various neurotoxic, viral and immune-mediated mechanisms. Molecular techniques have recently generated mouse models in which genes relevant to the human disease or motor neuron biology have been manipulated. Transgenic mouse overexpressing the mutated SOD1 gene of FALS patients, provide significant insights into mechanisms of motor neuron degeneration in this disease (reviewed by Pioro Clin Neurosci. 1995-1996; 3(6):375-85).

Of specific relevance is a new transgenic mouse model with mutant TDP-43 appears to be similar to human sporadic amyotrophic lateral sclerosis, opening up new opportunities for research on targeted therapies, described in Talan Neurology Today: 19 Nov. 2009—Volume 9—Issue 22—p 10-11.

According to a specific embodiment, the mouse model is the A315T stop mouse model (Wegorzewska, 2009 PNAS 106, p. 18809-14) from Jackson Laboratories Inc.).

Another exemplary mouse model are the transgenic SOD1 (superoxide dismutase 1) mice (described in the Examples section which follows) which express a G93A mutant form of human SOD1. SOD1 mice (TgN-SOD1-G93A-1Gur) exhibit a phenotype similar to amyotrophic lateral sclerosis (ALS) in humans (Gurney, 1994, Science 264 p. 1772-5).

Additional animal models for screening potential anti-stress agents can be found in Jaggi A S et al., Neurol Sci. (2011) 32(6):993-1005.

Mouse doses vary from 10-1000 mg/kg/day, 10-500 mg/kg/day, 50-200 mg/kg/day, 50-100 mg/kg/day. The doses can be effectively transformed to human uses by employing FDA conversion tables.

The intermediate dose of 100 mg/kg orally in drinking water per day was previously described to be active and non-toxic in mice, leading to mean serum peak concentrations of 4 mg/l [Enoxacin pharmacokinetics and efficacy in CF-1 mice, Chartand S. A. et al, Journal of Antimicrobial Chemotherapy (1987) 19, 221-224]. This corresponds to a dose of 12.5 µM Enoxacin. Given the fact that the dose is applied continuously and well absorbed, a certain tissue specific accumulation can be assumed. Enoxacin was previously described to cross the blood brain barrier.

Comparable serum peak concentrations were observed in humans, where a single Enoxacin of 600 mg led to a plasma peak concentration of 3.7 mg/ml. Depending on the necessary tissue penetrance, common doses of Enoxacin vary between 2×200 mg/day and 2×400 mg/day, the later has been regarded as a standard dose for many years. Given this, our employed dose fits perfectly in the necessary serum peak concentration range of antimicrobial efficacy of the drug, whether this is sufficient for miRNA enhancing activity in vivo motorneurons needs to be yet evaluated. Wise R, Lockley R, Webberly M, Adhami Z N. The pharmacokinetics and tissue penetration of enoxacin and norfloxacin. J Antimicrob Chemother. 1984 September; 14 Suppl C:75-81. PubMed PMID: 6238932. Wolf R, Eberl R, Dunky A, Mertz N, Chang T, Goulet J R, Latts J. The clinical pharmacokinetics and tolerance of enoxacin in healthy volunteers. J Antimicrob Chemother. 1984 September; 14 Suppl C:63-9. PubMed PMID: 6389476.

Thus according to a specific embodiment, human doses are 100-2000 mg/day, 100-1000 mg/day, 400-800 mg/day or 200-600 mg/day. The dose can be divided to multiple unit doses forms given once, twice or more per day.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide optimal levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The pharmaceutical compositions of the present invention may further comprise as an active ingredient an anti-ALS agent.

An exemplary anti-ALS agent comprises Riluzole (e.g. Rilutek®).

According to a specific embodiment, the pharmaceutical composition comprises a quinolone (e.g. enoxacin) and an anti-ALS agent (e.g. Riluzole).

According to an embodiment, the pharmaceutical compositions and/or therapeutic regimen of the present invention may further comprise additional factors which enhance processing of a pre-miRNA, including for example, Dicer (e.g. Dicer1), PACT, TRBP, Ago (e.g. Ago2), heat-shock protein 90 (Hsp90), co-chaperone p23, eukaryotic translation initiation factor 3 (eIF3), eukaryotic translation initiation factor 5A (eIF5a), eukaryotic translation initiation factor 2, subunit 1 alpha (eIF2S1) and/or poly(C)-binding protein 2 (PCBP2) or poly(C)-binding protein 1 (PCBP1).

The pharmaceutical compositions of the present invention may further comprise as an active ingredient an agent capable of decreasing cellular stress (e.g. an agent capable of inhibiting formation and/or enhancing disaggregation of stress granules).

The active ingredients of the pharmaceutical composition may be co-formulated or may be in separate formulations.

The active ingredients of the pharmaceutical composition may be in a single or in separate containers.

According to one embodiment, the pharmaceutical composition may comprise a cycloheximide, a mithramycin A (also known as Plicamycin; trade name Mithracin), a parthenolide, a mycophenolic acid [also known as mycophenolate mofetil, marketed under the trade names CellCept (Roche), Myfortic (Novartis)], a sodium phenylbutyrate [marketed under the trade names: Buphenyl (Ucyclyd Pharma, Hunt Valley, USA), Ammonaps (Swedish Orphan International, Sweden), triButyrate (Fyrlklövern Scandinavia)] a salubrinal, a GSK2606414, a Geldanamycin or a Geldanamycin analogue (e.g. 17-AAG or 17-DMAG).

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to one embodiment, there is provided an article of manufacture comprising an agent capable of enhancing processing of a pre-miRNA and an anti-ALS agent being packaged in a packaging material and identified in print, in or on the packaging material for use in the treatment of ALS.

According to a specific embodiment, the article of manufacture comprises a quinolone (e.g. enoxacin) and an anti-ALS agent (e.g. Riluzole).

According to one embodiment, there is provided an article of manufacture comprising in separate containers an agent capable of enhancing processing of a pre-miRNA and an agent capable of decreasing cellular stress, wherein the article comprises an identification in print for use in the treatment of a cellular stress-related disease.

The present findings that the general miRNA metabolism is impaired in MND, suggests further diagnostic implications of these diseases.

Thus, according to an additional aspect of the invention there is provided a method of diagnosing a MND, the method comprising analyzing in a sample of a subject in need thereof:

(i) total miR expression; and optionally (ii) total pre-miR expression, wherein a down-regulation in said (i) or (i)/(ii) beyond a predetermined threshold is indicative of the MND.

Alternatively or additionally, there is provided a method of diagnosing a MND, the method comprising analyzing in a sample of a subject in need thereof:

(i) a miR expression; and (ii) an expression of a precursor of said miR, wherein a down-regulation in (i)/(ii) beyond a predetermined threshold is indicative of the MND.

As used herein the phrase "total miRNA" refers to non-specific miRNA quantification per cell/cells/tissue. According to a specific embodiment only the levels of the mature miRNA and not its precursor are measured, so as to quantify only the portion of the miRNA in the cell/cells/tissue.

As used herein the phrase "total pre-miRNA" refers to non-specific miRNA quantification per cell/cells/tissue. According to a specific embodiment only the levels of the pre-miRNA and not its mature product (miRNA) are measured, so as to quantify only the portion of the pre-miRNA in the cell/cells/tissue.

Thus, the ratio between miRNA (mature) and pre-miRNA is crucial to the etiology of the disease.

Therefore, the present invention further contemplates analyzing the levels of a specific miRNA which lack thereof (or insufficient level thereof) has been associated with MND or ALS, provided that this is effected also by quantifying the precursor level of the specific miRNA tested.

Such miRNAs are provided in U.S. Patent Applications 20060247193 and 20090246136, each of which is hereby incorporated by reference in its entirety.

According to a specific embodiment, the specific miRNA selected from the group consisting of miR-9, miR-206, miR-1, miR-2-1, miR-5, miR-7, miR-8, miR-11, miR-12, miR-13, miR-14, miR-15, miR-16, miR-17, miR-18, miR-19, miR-20, miR-21, miR-22, miR-23, miR-24, miR-25, miR-26, miR-27, miR-28, miR-29, miR-30, miR-31, miR-32, miR-33, miR-34, miR-92, miR-93, miR-94, miR-95, miR-96, miR-97, miR-98, miR-99, miR-100, miR101, miR-103, miR-104, miR-105, miR-106, miR-107, miR-109, miR-110, miR-111, miR-112, miR-113, miR-114, miR-116, miR-119, miR-122, miR-125, miR-126, miR-127, miR-129, miR-130, miR-132, miR-133, miR-134, miR-136, miR-138, miR-140, miR-141, miR-144, miR-145, miR-146, miR-147, miR-148, miR-149, miR-150, miR-151, miR-153, miR-154, miR-157, miR-158, miR-160, miR-162, miR-164, miR-172, miR-173, miR-174, miR-175, miR-176, miR-177, miR-178, miR-179, miR-180, miR-182, miR-183, miR-184, miR-185, miR-186, miR-187, miR-188, miR-189, miR-191, miR-192, miR-193, miR-195, miR-196, miR-197, miR-199, miR-201, miR-203, miR-205, and miR-224 or a precursor thereof.

As used herein, the term "diagnosing" refers to classifying a pathology (e.g., a disease, disorder, syndrome, medical condition and/or a symptom thereof), determining a severity of the pathology, monitoring the progression of a pathology, forecasting an outcome of the pathology and/or prospects of recovery (e.g., prognosis).

As used herein "a biological sample" refers to a sample of fluid or tissue sample derived from a subject. Examples of fluid samples include, but are not limited to, blood, plasma, serum, spinal fluid, lymph fluid, tears, saliva, sputum and milk. An example of a tissue sample includes a brain tissue sample or a nerve tissue sample (e.g. for post-mortem diagnosis).

Methods of obtaining such biological samples are known in the art including but not limited to standard blood retrieval procedures and lumbar puncture.

As used herein, the term "subject" refers to a mammal, such as a human being as described above. The subject may be healthy or showing preliminary signs of a MND, such as muscle fatigue. Alternatively, the subject may have a genetic predisposition to the disease.

Determining the total miRNA level with and without determining the precursor level is performed using methods which are well known in the art. A brief exemplary description is provided herein. RNA is extracted such as by using an RNA isolation kit e.g., Trireagent (Molecular Research Center Inc.). Reverse transcription for consecutive parallel analysis of pre-miRNA and miRNA expression is done using miScript I & II Kits (Quiagen). Quantitative analysis of miRNA and pre-miRNA expression performed with StepOnePlus Real-Time PCR System (Life technologies Inc.). All experiments are preferably performed independent biological repeats. qPCR is preferably performed in technical duplicates.

Following analysis of the total miRs and optionally pre-miR, the results are typically recorded and the subject is informed. The diagnosis may be substantiated with other means including those that make up the El Escorial criteria. Other diagnostic methods that can be used in conjunction with the method of the present invention are those that involve transcranial magnetic stimulation (TMS). This non-invasive procedure creates a magnetic pulse inside the brain that stimulates motor activity in a certain area of the body. Electrodes taped to different areas of the body pick up and record the electrical activity in the muscles.

It will be appreciated that the diagnostic method of the present invention may also be substantiated with other tests to rule out the involvement of other diseases or to measure the extent of muscle involvement. Below is a list of such tests:

1. Electromyography (EMG) is used to diagnose muscle and nerve dysfunction and spinal cord disease. It is also used to measure the speed at which impulses travel along a particular nerve. EMG records the electrical activity from the brain and/or spinal cord to a peripheral nerve root (found in the arms and legs) that controls muscles during contraction and at rest. Very fine wire electrodes are inserted one at a time into a muscle to assess changes in electrical voltage that occur during movement and when the muscle is at rest. The electrodes are attached to a recording instrument. Testing usually lasts about an hour or more, depending on the number of muscles and nerves to be tested.

2. EMG is usually done in conjunction with a nerve conduction velocity study. This procedure also measures electrical energy to test the nerve's ability to send a signal. A technician tapes two sets of flat electrodes on the skin over the muscles. The first set of electrodes is used to send small pulses of electricity (similar to a jolt from static electricity) to stimulate the nerve that directs a particular muscle. The second set of electrodes transmits the responding electrical signal to a recording machine. The physician then reviews the response to verify any nerve damage or muscle disease.

3. Laboratory screening tests of blood, urine, or other substances can rule out muscle diseases and other disorders that may have symptoms similar to those of MND. For example, analysis of the fluid that surrounds the brain and spinal cord can detect a number of disorders, including PPS. Blood tests may be ordered to measure levels of the protein creatine kinase (which is needed for the chemical reactions that produce energy for muscle contractions); high levels may help diagnose muscle diseases such as muscular dystrophy.

4. Magnetic resonance imaging (MRI) uses computer-generated radio waves and a powerful magnetic field to produce detailed images of body structures including tissues, organs, bones, and nerves. These images can help diagnose brain and spinal cord tumors, eye disease, inflammation, infection, and vascular irregularities that may lead to stroke. MRI can also detect and monitor degenerative disorders such as multiple sclerosis and can document brain injury from trauma. MRI is often used to rule out diseases other than the MNDs that affect the head, neck, and spinal cord.

5. Muscle or nerve biopsy can help confirm nerve disease and nerve regeneration. A small sample of the muscle or nerve is removed under local anesthetic and studied under a microscope. The sample may be removed either surgically, through a slit made in the skin, or by needle biopsy, in which a thin hollow needle is inserted through the skin and into the muscle. A small piece of muscle remains in the hollow needle when it is removed from the body. Although this test can provide valuable information about the degree of damage, it is an invasive procedure that may itself cause neuropathic side effects. Many experts do not believe that a biopsy is always needed for diagnosis.

The present invention further contemplates a method of identifying an agent for the treatment of a MND, the method comprising:

(a) contacting a motor neuron of an ALS patient or an ALS model with a candidate agent;

(b) analyzing prior to (a) and following (a):

(i) total miR expression in said motor neuron; and optionally (ii) total pre-miR expression in said motor neuron, wherein an up-regulation in said (i) or (i)/(ii) beyond a predetermined threshold following (a) as compared to prior to (a), is indicative of that the candidate compound is a therapeutic agent for the treatment of MND.

The motor neuron may be isolated from any animal, including a mouse, a rat or a human. Alternatively, the motor neuron may be part of a motor neuron cell line—such as for example the murine motor neuron cell line, NSC19 [Smirnova I V Spine (Phila Pa. 1976). 1998 Jan. 15; 23(2): 151-8].

Yet alternatively, the motor neuron may be differentiated from a stem cell. According to one embodiment the stem cell is an embryonic stem cell (ESC). Such embryonic stem cells may be isolated from transgenic animals (e.g. mice) that serve as models for MNDs. For example embryonic stem cells may be isolated from a Tg(Hlxb9-GFP)1Tmj Tg(SMN2)89Ahmb Smn1$^{tm1Msd}$/J mouse (Jackson lab stock number 006570). Alternatively, embryonic stem cells may be isolated from transgenic animals, comprising a cholinergic-specific knock-out of DICER. This model for MND is further described herein below.

Various methods are known for differentiation of embryonic stem cells into motor neurons, such as for example those described by Wichterle, H., et al., [Cell 110, 385-97 (2002)].

Exemplary candidate agents include small molecule agents, polynucleotide agents, chemicals, antibiotic compounds known to modify gene expression, modified or unmodified polynucleotides (including oligonucleotides), polypeptides, peptides, small RNA molecules and miRNAs.

It will be appreciated that the methods of contacting according to this aspect of the present invention typically depend on the type of candidate agent being tested. Thus, for example a polynucleotide agent is typically contacted with the motor neuron together with a transfection agent. A small chemical is typically placed in the motor neuron culture medium without additional agents.

To be considered a therapeutic agent, the candidate agents of the present invention typically upregulates (i) or (i)/(ii) beyond a predetermined threshold following (a) as compared to prior to (a).

Following selection of a candidate agent as a therapeutic agent for the treatment of an MND, the agent may be tested—for example on an animal model for the disease and ultimately the agent may be tested in humans. Validation of therapeutic efficacy may then lead to the preparation of the candidate agent as a pharmaceutical composition.

Such a method, beyond its significance to research and pharmaceutical industry, is also valuable in the field of personalized medicine. Cells of the subject are contacted with a candidate treating agent (e.g., enoxacin) and compliance to treatment is dependent on upregulation in (i) or (i)/(ii) following contacting.

As used herein the term "about" refers to ±10%.

The terms "comprises", "comprising", "includes", "including", "having" and their conjugates mean "including but not limited to".

The term "consisting of" means "including and limited to".

The term "consisting essentially or means that the composition, method or structure may include additional ingredients, steps and/or parts, but only if" the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Experimental Procedures

Human Tissue miRNA Analysis

In situ-hybridization was performed on 7 μm sections of frozen spinal tissue from lumbar regions, following[10], Hybridization of sections with 4 pmol of 5' and 3' DIG-labeled anti-miR-9 and anti-miR-124 LNA probe followed manufacturer instructions (Exiqon).

For miRNA studies in cultured cells, reverse transcription for consecutive parallel analysis of pre-miRNA and miRNA expression was performed using miScript I & II Kits (Quiagen). Quantitative analysis of miRNA and pre-miRNA expression performed with StepOnePlus Real-Time PCR System (Life technologies Inc.). All experiments were performed in at least 3 independent biological repeats and qPCR performed in technical duplicates.

For in vivo experiments, transgenic SOD1 (superoxide dismutase 1) mice were used which express a G93A mutant form of human SOD1. SOD1 mice (TgN-SOD1-G93A-1Gur) exhibit a phenotype similar to amyotrophic lateral sclerosis (ALS) in humans. 20 mice were fed with Enoxacin (at a dose of 200 mg/kg) from the age of 50 days in drinking water. Mouse life span and neuromuscular function were monitored. Neuromuscular function was assessed by neurological score that tests the mouse muscle tonus reflexes and overall in-cage locomotive activity as previously described in Alves C J et al. [Alves C J et al., Brain Res. (2011) Jun. 7; 1394:90-104]. Hang-wire test was utilized which measures gross physical strength of forelimbs, hindlimbs, capacity to adduct when hand on a pole and to walk. Automated Catwalk gait analysis system was utilized which is based on camera monitored computerized locomotion testing automated system by Noldus Information Technology, The Netherlands.

Statistical analysis was performed using the two-tailed Student's t-test with post-hoc Benjamin-Hochberg corrections. Values were considered statistically significant when $p<0.05$. Results are representative of at least 3 independent experiments and presented with standard deviations. qPCR data statistics for the human miRNA study was obtained using the DataAssist Software (Life Technologies).

Example 2 miRNA Expression is Altered in ALS

Previous reports have indicated that a general (non-specific) microRNA (miRNA) metabolism is altered in ventral lumbar spinal cord (SC) tissue in sporadic ALS (sALS) subjects as compared to controls [Campos-Melo D. et al. Mol Brain. (2013) 6:26]. In the present study, the present inventors have tested the hypothesis that the altered miRNA expression in ALS subjects is related to a mutation in miRNA bioprocessing and may be reversed by proper treatment.

First, the observation that miRNAs are globally down-regulated in ALS subjects was substantiated by miRNA in-situ hybridization[10], which revealed comparable downregulation of miR-9 and miR-124 in patient tissue, relative to control (FIGS. 1A-C). These data suggest that miRNAs are broadly downregulated in ALS motoneurons. To gain mechanistic insight into miRNA dysregulation in ALS, the present inventors transfected HEK293 or NSC-34 cells with vectors for expression of ALS-causing mutant forms of FUS and TDP-43 and examined miRNA expression. Transfection of the mixed motor-neuron cell line, NSC-34, with vectors for expression of ALS-causing mutant forms of TDP-43 and FUS revealed that mature miRNA expression was downregulated in all cases (FIGS. 2A-D and FIG. 3). These data reveal that the presence of toxic ALS-causing mutants is sufficient to disrupt miRNA processing. Canonical miRNA bioprocessing involves the digestion of pre-miRNA precursors by the Drosha/Dgcr8 complex in the nucleus and subsequently by Dicer1 in the cytoplasm. Therefore specific impairment of the bioprocessing system may be revealed by the accumulation of intermediate miRNA forms. Quantitative analysis of pre-miRNAs in NSC-34 cells extracts, revealed that while mature miRNAs were downregulated, the levels of their cognate pre-miRNA precursors were in fact upregulated by the expression of ALS-causing mutant-forms of TDP-43 or FUS (FIGS. 2A-D and FIG. 3). Noteworthy, the impairment of pre-miRNA processing into mature miRNAs seems to correlate with the reported clinical severity, reported for different FUS and TDP-43 mutants. Attempts to measure pre-miRNAs in human LCM samples were unsuccessful, probably due to the very low expression levels of these intermediate precursors. This reciprocity, whereby mature miRNAs levels are low and per-miRNA precursors are higher than in the control, suggested inhibition of pre-miRNA processing by Dicer1[11].

The present inventors reasoned that Dicing of pre-miRNAs is inhibited by the expression of ALS-causing versions of TDP-43 or FUS and thus searched for changes in mRNA encoding for miRNA-processing factors in gene expression and splicing data from the same patients[9]. However, these interrogations did not reveal any change in the expression of these factors in ALS patients relative to controls. To provide functional experimental support to the role of Dicing in disturbed miRNA processing by ALS-causing mutant forms of TDP-43 and FUS, the present inventors sought employ Enoxacin, a Fluoroquinolone antibiotic, which is known to increase miRNA levels via enhancement of Dicer1 activity[12]. Indeed, introduction of Enoxacin onto HEK293 cells reversed the negative impact of ALS-causing TDP-43 or FUS mutants on miRNA maturation (FIGS. 2E-H). Thus, impaired miRNA bioprocessing in ALS may be reversible by a non-toxic Fluoroquinolone.

This observation encouraged a hypothesis that Enoxacin may be beneficial also in vivo, in the classic SOD1 G93A model of ALS (high copy number, missed genetic background). Therefore the present inventors set to perform a preclinical study by feeding a cohort of mice with Enoxacin from the age of 50 days in drinking water. This preliminary study failed to clearly show—mechanism involved in several forms of ALS that may be of therapeutic usage in the future, employing existing or yet to be developed more potent molecules modulating miRNA maturation or activity.

Since miRNAs are detectable in bodily-fluids including in cerebrospinal-fluid, this may allow future development of miRNA-based markers for ALS. Additionally, these observations advance understanding of molecular mechanisms acting in other forms of neurodegeneration, as dysregulation of miRNAs was suggested in several other brain diseases.

Acknowledging that loss of miRNA and Dicer1 activity in motoneurons is sufficient for causing motoneuron disease in mice[7], strongly suggests that the global miRNA downregulation reported here may affect motoneuron survival also in human ALS patients. Thus, the present findings suggest a common mechanism involved in several forms of ALS that may be of therapeutic usage in the future, if potent molecules modulating miRNA maturation or activity could be developed.

Example 3

Further Experimental Procedures

Human Tissue miRNA Analysis

Human nervous tissues were acquired by way of an Investigational Review Board and Health Insurance Portability and Accountability Act compliant process. Sporadic ALS nervous systems were from patients who had met El Escorial criteria for definite ALS. Sporadic ALS nervous systems were from patients who had bulbar or arm-onset disease and caudal progression and thus the lumbar regions had relatively abundant residual motor neurons. Tissue collections were as previously described: completed within 4-6 hours of death, the motor system was dissected, embedded in OCT and stored at −80° C. RNA quality was assessed using microelectrophoresis on an Agilent 2100 Bioanalyzer as previously described. Microdissected cell punches were captured on CapSure™ Macro LCM Caps (Arcturus Bioscience). 35-50 cryosections were cut at a thickness of 9 µm in a −18° C. cryotome and placed onto uncharged glass slides. The sections were returned to −80° C. for a minimum of three hours. They were stained with cresyl violet acetate in a 10-step, timed, nuclease-free immersion process. Motor neurons were microdissected using a Pixcell IIe Laser Capture Microdis section (LCM) System (Arcturus Bioscience) and CapSure™ Macro LCM Caps (Applied Biosystems). Each LCM session collected 500-1000 motor neuron punches and lasted less than 2.5 hours. Total RNA was isolated using the RNAqueous Micro kit (Life Technologies) per manufacturer's procedure. RNA quality was assessed by spectrophotometic analysis using a Nanodrop ND-1000 spectrophotometer and an Agilent 2100 Bioanalyzer. Expression of 667 microRNAs was assessed using the microRNA TaqMan® qPCR Megaplex pools array on an ABI 7900HT Fast Real-Time PCR System (Life Technologies). Technical replicates were run after pre-amplification using the manufacturer's protocol. Data analysis was performed with DataAssist™ Software. Relative quantification was calculated by comparing to arithmetic mean of two small RNA control genes (U6, RNU48).

In situ-hybridization was performed on 7 µm sections of frozen spinal tissue from lumbar regions, briefly fixed in 4% paraformaldehyde and incubated in 2 µg/ml Proteinase K. Slides were then incubated for 10 minutes in 0.13 M 1-methylimidazole (Sigma), 300 mM NaCl, pH 8.0 and further fixed in EDC (Sigma) following Pena et al. [Pena et al. (2009) Nat Methods 6(2): 139-141], acetylated for 30 minutes in a solution of freshly prepared 0.1 M triethanolamine and 0.5% (v/v) acetic anhydride. Hybridization of sections with 4 pmol of 5' and 3' DIG-labeled miR-9 and miR-124 LNA probes followed manufacturer instructions (Exiqon).

Tissue Culture, Vectors and Small Molecules

HEK293 cells (American Type Culture Collection) and NSC-34 cells (Cellutions Biosystems Inc.) were cultured in high-glucose DMEM (Gibco), L-Glutamin 1%, 10% fetal calf serum and 1% Penicillin/Streptavidin. Mouse embryonic fibroblasts (MEFs) were cultured in DMEM (Gibco), 15% fetal calf serum, L-Glutamin, 1% Penicillin/Streptavidin, and Sodium Pyruvate. Stably Ago2-Flag expressing HEK293 and eIF2a S51A mouse embryonic fibroblasts were also used. Mouse embryonic motor neurons were harvested as described in Milligan & Gifondorwa [Milligan and Gifondorwa (2011) Methods Mol Biol 793: 77-85].

FUS expression vector, Wild-type R495X, R525L and R521G were used. TDP-43 expression vector, Wild-type, A315T and M337V were also used. Wild-type SOD1 expression vector and the mutants SOD1 G93A were further used as well as Dicer plasmids.

Enoxacin was from Sigma-Aldrich (E3764-5G) or Buckton-Scott (Germany). 17-AAG, Geldanamycin and Thapsigargin were from Sigma-Adrich, Israel. Cycloheximide Paraquat and Puromycin were obtained from Sigma-Aldrich, Israel.

RNA Analysis

RNA was extracted using Tri reagent (Molecular Research Center Inc.) or Qiazol with consecutive use of the miRNeasy Mini Kit (Qiagen). Pre-miRNA and miRNA reverse transcription was performed using miScript Kits No. I & II (Qiagen). Quantitative analysis of miRNA and pre-miRNA expression performed in more than 3 independent biological repeats and additionally in technical duplicates with StepOnePlus quantitative Real-Time PCR System and 2-sided ANOVA-test performed with DataAssist Software (Life technologies Inc.). Next-generation sequencing of mouse precursor miRNAs and mature miRNAs was performed on two independent experimental repeats, as described in Newman et al. [Newman et al. (2011) RNA 17(10): 1795-1803]. miRNAs were normalized to spiked-in controls and pre-miRNAs were normalized to Snord72 and Snord95.

Mass-spectrometry and Western Blot Studies

Stably Ago2-Flag expressing cells were grown in 10 cm or 3.5 cm plates and transfected using Lipofectamin (Invitrogen) with plasmids as listed. Expression of proteins was induced by Doxycyclin (Sigma, 1 µg/ml) 6 hrs after transfection and cells were harvested after 72 hrs.

For western blot analysis, 6% and 10% SDS-polyacrylamide gel electrophoresis of cell lysate was followed by electrotransfer to nitrocellulose membranes (Biorad), 60 minutes. Blocking was performed with 5% milk-powder in TBS, 0.05% Tween 20, at room temperature. Primary antibody incubation was performed at concentration of 1:1000 overnight with anti-peIF2 alpha Ser 52 (Santa Cruz, sc-101670), eIF2 alpha (Santa-Cruz, sc-11386), anti-GAPDH (Abcam, mAbcam9484), anti-Dicer (Abcam, mAbcam13502) and anti-Ago2 monoclonal 2A8 antibody. Peroxidase-conjugated secondary antibodies were incubated for 45 minutes at room temperature.

For mass-spectrometry, HEK293 that either stably express Ago2-FLAG (n=3 for each group) or Dicer-Flag transfected cells (48 hrs post-transfection, n=4 for each group) were untreated or stressed with 0.5 mM sodium arsenite for 60 minutes before harvest. IP was performed with the FLAG-IPT1 Kit (Sigma-Aldrich). Negative controls were HEK293 cells not containing a FLAG-construct. Samples containing the eluted proteins and the FLAG peptide were filtered using 3 kDa molecular weight cut-off spin columns (Amicon, Millipore). Buffer was exchanged to 50 mM ammonium bicarbonate (Sigma-Aldrich) in the same step. Proteins were reduced by addition of dithiothreitol (Sigma-Aldrich) to a final concentration of 5 mM and incubation for 30 minutes at 60° C., and alkylated with 10 mM iodoacetamide (Sigma-Aldrich) in the dark for 30 minutes at 21° C. The proteins were then digested using trypsin (Promega; Madison, Wis., USA) at a ratio of 1:50 (w/w trypsin/protein) for 16 hrs at 37° C. Digestion was stopped by addition of 1% trifluroacetic acid (TFA). Samples were stored in −80° C. until analysis. Each sample was spiked with the mixture of 51 heavy isotopically labeled peptides (JPT Technologies). Heavy labels included U-$^{13}C_6$; U-$^{15}N_4$ for peptides terminating with Arg and U-$^{13}C_6$; U-$^{15}N_2$ for Lys. ULC/MS grade solvents were used for all chromatographic steps. Each sample was loaded using splitless nano-ultra performance liquid chromatography (10 k psi nanoAcquity; Waters, Milford, Mass., USA). Mobile phase was: A) water+0.1% formic acid and B) acetonitrile+0.1% formic acid. Desalting of samples was performed online using a reverse-phase C18 trapping column (180 µm i.d., 20 mm length, 5 µm particle size; Waters). The peptides in samples were separated using a C18 T3 HSS nano-column (75 µm i.d., 250 mm length, 1.8 µm particle size; Waters) at 0.3 µL/minute. Peptides were eluted from the column and into the mass spectrometer using the following gradient: 3% to 30% B in 90 min, 30% to 35% in 10 min, 35% to 90% B in 5 min, maintained at 90% for 5 minutes and then back to initial conditions. The analytical column was coupled with a quadrupole orbitrap mass spectrometer (Q Exactive, Thermo Scientific), via a nanoESI interface. Parallel reaction monitoring of mass spectrometry (MS) was according to Peterson et al. [Peterson et al. (2012) Mol Cell Proteomics 11(11): 1475-1488] at maximum injection time of 300 msec, resolution of 35,000 and target automatic gain control (AGC) of 2e5. Samples were analyzed in a random order, measuring the light and heavy forms of each target peptide. Data was processed with Skyline software as taught in MacLean et al. [MacLean et al. (2010) Bioinformatics 26(7): 966-968]. Extracted ion chromatograms were integrated and the ratio of the light to heavy forms was calculated. Student's T-Test was used, after logarithmic transformation, for statistical calculations of the differential peptide expression.

In Vivo Enoxacin Study

All experiments were performed according to Weizmann Institute of Science guidelines and IACUC approval (protocol No. 03040512-1). Mice, B6SJL-Tg(SOD1*G93A) 1Gur/J, that were first reported in Gurney et al. [Gurney et al. (1994) Science 264(5166): 1772-1775], carry a hemizygous high transgene copy number of the SOD1 G93A mutant on a B6SJL hybrid background (Jackson Laboratories, 002726). The TDP-43 A315T mouse line [described in Wegorzewska et al, (2009) Proc Natl Acad Sci USA 106 (44): 18809-18814] has a C57BL/6J background (Jackson Laboratories, 010700). All experiments were performed sibling-matched, except the mice in the 200 mg/kg body weight SOD1 G93A Enoxacin group, in which mice were randomly assigned to treatment groups. Animals were group-housed on a 12 hour light-dark cycle. Food and water was provided ad libitum. Food pellets at cage floor, long sipper tubes on bottles and nutrient gel were used to ease accessibility to nutrition when mice deteriorated according to Gill et al. [Gill et al. (2009) PLoS One 4(8): e6489]. RotaRod™ performance (San Diego Instruments) was evaluated at ramp speed 4, 40 rpm. Data was presented as the average latency to fall off the rotarod of three independent rounds per time point, and was normalized to average initial performance at pre-symptomatic stage for each individual for each time point. A fully automated gait analysis with the Catwalk XT™ (Noldus) system was performed. Data was obtained of more than 4 independent rounds on the apparatus. For Hangwire muscle strength assessment, mice were allowed forelimb grip onto a 2-mm thick horizontal metal wire, suspended 80 cm above surface. Ability to successfully raise hindlimbs to grip the wire and crawling to the end of the wire was scored: 1=Successful four-paw grip and crawling to the end of the wire within less than 60 seconds. 2=Four-paw grip for more than 15 seconds without crawling. 3=Failure to successfully establish hindlimb grip in 60 seconds. 4=Inability to sustain forelimb grip for 60 seconds. Each mouse was evaluated in 2 sessions on 2 consecutive days, consisting of 3 trials each, with a 15 minute inter-trial interval. The second day was used to obtain the data as displayed. Neurological score was assessed according to [Gill et al. (2009), supra]: 0=more than 2 second extension of hindlimbs away from lateral midline when mouse is suspended by its tail 2-3 times. 1=collapse or partial leg collapse towards midline or hind leg trembling during tail suspension. 2=toes curl under at least twice during a 12 inch walk, or any part of foot is dragging along cage/table bottom. 3=rigid paralysis or minimal joint movement, foot not being used for forward motion. 4=humane endpoint, mouse cannot right itself within 30 seconds on either side. The locomotion of animals was quantified over a period of 46 hrs in the home cage, by automated sensing of body-heat image using an InfraMot (TSE-Systems). Individual animal movements were summed up every 30 minutes. Animal statistics: Homecage locomotion was analyzed using the 2-sided Student's t-test. Rotarod performance was evaluated using the 2-way ANOVA with repeated measures for each individual. Weight peak, weight decline, onset of symptoms and survival were calculated with GraphPad Prism 6 using the Logrank (Mantel-Cox) test. All other tests employed 2-way ANOVA.

All primers are described in Table 1, below, and additional pre-miRNA sequences are from Jiang et al. [Jiang et al. (2005) Nucleic Acids Res 33(17): 5394-5403]. Peptide sequences for mass spectrometry are described in Table 2, below.

TABLE 1 primer sequences (mouse and human)

| SEQ ID NO: | Mouse primer sequences: | |
|---|---|---|
| 1 | pre-miR 10b fw- | CCTGTAGAACCGAATTTGTG |
| 2 | pre-miR 10b rv- | TCGAATCTGTGACTATGTGG |
| 3 | pre-miR 30a fw- | GTAAACATCCTCGACTGGAAGCT |
| 4 | pre-miR 30a rv- | GCTGCAAACATCCGACTGAA |
| 5 | pre-miR 103-2 fw- | GTCTTCGTGCTTTCAGCTTC |
| 6 | pre-miR 103-2 rv- | TTCTTGGTTCTTTCATAGCC |
| 7 | U6- | GATGACACGCAAATTCGTGAA |
| 8 | 5S- | AATACCGGGTGCTGTAGGCTT |
| 9 | snoRNA 234 (Snord70)- | GCTGTACTGACTTGATGAAAGTA |
| 10 | snoRNA 202 (Snord68)- | CTTTTGGAACTGAATCTAAGTGA |
| 11 | mmu-miR-10b- | TACCCTGTAGAACCGAATTTGTG |
| 12 | mmu-miR-30a- | TGTAAACATCCTCGACTGGAAG |
| 13 | mmu-miR-30c-5p- | UGUAAACAUCCUACACUCUCAGC |

TABLE 1-continued primer sequences (mouse and human)

| 14 | mmu-miR-103-3p- | AGCAGCATTGTACAGGGCTATGA |
|---|---|---|
| 15 | mmu-miR-132-3p- | TAACAGTCTACAGCCATGGTCG |
| 16 | mmu-miR-132-5p- | AACCGTGGCTTTCGATTGTTAC |
| 17 | mmu-miR-138-5p- | AGCTGGTGTTGTGAATCAGGCCG |
| 18 | mmu-miR-143-3p- | TGAGATGAAGCACTGTAGCTC |
| 19 | mmu-miR-218-5p- | TTGTGCTTGATCTAACCATGT |
| 20 | mmu-miR-221-5p- | ACCTGGCATACAATGTAGATTTCTGT |
| 21 | mmu-let-7b-5p- | TGAGGTAGTAGGTTGTGTGGTT |
| 22 | mmu-let-7a-5p- | TGAGGTAGTAGGTTGTATAGTT |
| 23 | mmu-let-7d-5p- | AGAGGTAGTAGGTTGCATAGTT |
| 24 | Dicer1 fw- | CTGCCAAGTTTAGCCCAGCGGA |
| 25 | Dicer1 rv- | CCTGTAGCTCCGGCCAACACC |
| 26 | AGO2 fw- | AGCCGGCCCCGTTCTTGCTT |
| 27 | AGO2 rv- | CTCCCGGTGGTGCCGAAGTC |
| 28 | PACT fw- | AGCGATTCGAGGGGCGTCCA |
| 29 | PACT rv- | GCCCAAACTGAAGGTCCCGCTG |
| 30 | TARBP2 fw- | ATGACTTGCCGGGTGGAGCG |
| 31 | TARBP2 rv- | CGGGAGCTCACGCCAATGAA |
| 32 | ATF4 fw- | CGGGTGTCCCTTTCCTCTTC |
| 33 | ATF4 rv- | TGAAGAGCGCCATGGCTTAG |
| 34 | CHOP fw- | ACCTGAGGAGAGAGTGTTCCA |
| 35 | CHOP rv- | CAAGGTGAAAGGCAGGGACT |
| 36 | ASNS fw- | CCTTTTATCAGGGGCCTGG |
| 37 | ASNS rv- | ACTTGGGCCTCCTTGAGTTG |
| 38 | GRP78 fw- | CTATTCCTGCGTCGGTGTGT |
| 39 | GRP78 rv- | ATTCCAAGTGCGTCCGATGA |
| 40 | Beta-actin fw- | CACACCCGCCACCAGTTCG |
| 41 | Beta-actin rv- | GACCCATTCCCACCATCACACC |
| 42 | GAPDH fw- | TGGCAAAGTGGAGATTGTTGCC |
| 43 | GAPDH rv- | AAGATGGTGATGGGCTTCCCG |

| SEQ ID NO: | Human primer sequences: | |
|---|---|---|
| 44 | Beta-actin fw- | ACAGAGCCTCGCCTTTGCCG |
| 45 | Beta-actin rv- | ACCCATGCCCACCATCACGC |
| 46 | hsa-miR 20b- | CAAAGTGCTCATAGTGCAGGTAG |
| 47 | hsa-pre-miR 20b fw- | GTACCAAAGTGCTCATAGTGCAG |
| 48 | hsa-pre-miR 20b rv- | GTACTGGAAGTGCCCATACTACTACA |
| 49 | hsa-miR 21- | TAGCTTATCAGACTGATGTTGA |
| 50 | hsa-pre-miR 21 fw- | GCTTATCAGACTGATGTTGACTG |

TABLE 1-continued primer sequences (mouse and human)

| | | |
|---|---|---|
| 51 | hsa-pre-miR 21 rv- | CAGCCCATCGACTGGTG |
| 52 | hsa-miR 30e- | TGTAAACATCCTTGACTGGAAG |
| 53 | hsa-pre-miR 30e fw- | GTAAACATCCTCGACTGGAAGCT |
| 54 | hsa-pre-miR 30e rv- | GCTGCAAACATCCGACTGAA |
| 55 | hsa-miR-125a-5p- | TCCCTGAGACCCTTTAACCTGTGA |
| 56 | pre-miR 125 fw- | AGCCTAACCCGTGGATTT |
| 57 | pre-miR 125 rv- | TCCCTGAGACCCTAACTTGTGA |
| 58 | AGO2 fw- | CTGACAAGAACGAGCGGGTTGGG |
| 59 | AGO2 rv- | CGAAGGCCTGCTTGTCCCCTG |
| 60 | DICER fw- | GCTTGGGCATGCTGTGATTTTCCA |
| 61 | DICER rv- | AGGGGTTGCAAAGCAGGGCT |
| 62 | PACT fw- | AAAGACCTCGCTCACCCCGC |
| 63 | PACT rv- | TCCCCAAACTGTCTTCCGGCCC |
| 64 | TRBP fw- | TTGGTGCTCTGCAGGAGCTGGT |
| 65 | TRBP rv- | GCCGCATTCCGCTTTGCCAAT |
| 66 | CHOP fw- | GAACCTGAGGAGAGAGTGTTCA |
| 67 | CHOP rv- | AGTTTACCTGCTTTCAGGTGTG |
| 68 | Grp78 fw- | CCCGAGAACACGGTCTTTGA |
| 69 | Grp78 rv- | TTCAACCACCTTGAACGGCA |
| 70 | 5S- | AATACCGGGTGCTGTAGGCTT |

TABLE 2

Peptide sequences for mass spectrometry

| protein symbol | protein name | relevant function | SILAC peptides | SEQ ID NO: |
|---|---|---|---|---|
| PCBP1 | Poly(rC)-binding protein 1 | stress granules/P-bodies | AITIAGVPQSVTEiCVK | 71 |
| | | | LVVPATQiCGSLIGK | 72 |
| | | | IITLTGPTNAIFK | 73 |
| PCBP2 | Isoform 2 of Poly(rC)-binding protein 2 | stress granules/P-bodies | IITLAGPTNAIFK | 74 |
| | | | IANPVEGSTDR | 75 |
| | | | ESTGAQVQVAGDMLPNSTER | 76 |
| TNR6B | Trinucleotide repeat-containing gene 6B protein | P-bodies | STDAPSQSTGDR | 77 |
| | | | MDIDDGTSAWGDPNSYNYK | 78 |
| | | | SMQDGWGESDGPVTGAR | 79 |
| IF2A | Eukaryotic translation initiation factor 2 subunit 1 | stress granules | GYIDLSK | 80 |
| | | | VVTDTDETELAR | 81 |
| | | | GVFNVQMEPK | 82 |
| I3L504 | Eukaryotic translation initiation factor 5A-1 | stress granules | VHLVGIDIFTGK | 83 |
| | | | IVEMSTSK | 84 |
| eIF3L | Isoform 2 of Eukaryotic translation initiation factor 3 subunit L | stress granules | VYEIQDIYENSWTK | 85 |
| | | | VSSDVIDQK | 86 |
| | | | VFSDEVQQQAQLSTIR | 87 |
| HS90B | Heat shock protein HSP 90-beta | stress granules/RISC loading complex | IDIIPNPQER | 88 |
| | | | NPDDITQEEYGEFYK | 89 |
| | | | ELISNASDALDK | 90 |
| P23 | Prostaglandin E synthase 3, P23, TEBP | stress granules/RISC loading complex | SILiCiCLR | 91 |
| | | | LNWLSVDFNNWK | 92 |
| | | | DVNVNFEK | 93 |
| Dicer | dicer 1, ribonuclease type III | Dicer/RISC loading | SNAETATDLVVLDR | 94 |
| | | | FYVADVYTDLTPLSK | 95 |
| | | | ELPDGTFYSTLYLPINSPLR | 96 |
| TRBP | TAR (HIV-1) RNA binding protein 2 pseudogene | Dicer/RISC loading complex | TPVYDLLK | 97 |
| | | | DGNEVEPDDDHFSIGVGSR | 98 |
| PACT | protein kinase, interferon-inducible double stranded RNA dependent activator | Dicer/RISC loading complex | SDVQIHVPTFTFR | 99 |
| | | | VTVGDITiCTGEGTSK | 100 |
| | | | NQLNPIGSLQELAIHHGWR | 101 |

TABLE 2-continued

Peptide sequences for mass spectrometry

| protein symbol | protein name | relevant function | SILAC peptides | SEQ ID NO: |
|---|---|---|---|---|
| AGO2 | argonaute RISC catalytic component 2 | Dicer/RISC loading | VLQPPSILYGGR SVSIPAPAYYAHLVAFR SASFNTDPYVR | 102 103 104 |
| PAgo2 Ser-387 | phosphorylated Serine 387 on argonaute RISC catalytic component 2 | Dicer/RISC loading complex | SApSFNTDPYVR | 105 |

Example 4 microRNAs are Down-regulated in Motor Neurons of Human ALS Patients

It was previously demonstrated that conditional inactivation of Dicer in motor neurons is sufficient to cause spinal motor neuron degeneration in vivo [Haramati et al. (2010) Proc Natl Acad Sci USA 107(29): 13111-13116] and additional works further suggest the potential involvement of miRNAs in ALS pathogenesis [Buratti et al. (2010) FEBS J., supra]. In the present work, miRNA expression was examined in human ALS, thus miRNAs were quantified in lumbar motor neurons of sporadic ALS (sALS) and familial ALS (fALS) patients via laser-capture microdissection (LCM). Global down-regulation of miRNAs was observed in sALS motor neurons, relative to controls that did not have neurodegeneration. Furthermore, RNA extracted from surrounding, motor neuron-depleted ventral-horn tissue of sALS patients or from neurons of Clarke's column (non-motor neuron), within the same nervous systems, did not exhibit global changes in miRNA expression (FIGS. 6A-C). These observations were substantiated by miRNA in-situ hybridization, which revealed down-regulation of miR-9 and miR-124 in patient tissue, relative to control tissue and to the hybridization signal of U6 RNA (FIG. 6D). Next, it was investigated whether miRNAs display a similar profile in mutSOD1 fALS cases. Indeed, analyzing two nervous systems carrying familial SOD1 A4V mutation revealed similar down-regulation of miRNAs (FIGS. 6E-F). This data suggests that changes in miRNA expression, which were previously reported in ALS spinal cord extracts [Campos-Melo et al, (2013) supra], are primarily due to changes in miRNA expression in motor neurons. Attempts to measure pre-miRNAs in human LCM samples were unsuccessful, probably due to the low abundance of these intermediate precursors. Noteworthy, expression and splicing data for changes in mRNAs encoding miRNA-processing factors from the relevant ALS patients did not reveal any change, relative to controls [Rabin et al. (2009) Hum Mol Genet 19(2): 313-328]. Since miRNAs are globally down-regulated in sALS cases that are genetically unrelated, reduced miRNA expression appears to be a common denominator of various forms of ALS.

Example 5

Cellular Stress Affects Pre-miRNA Processing

Stress and cytoplasmic stress granules (SGs) emerge as major pathogenic mechanisms of ALS [Kim et al. (2014) Nat Genet 46(2): 152-160]. Stress pathways are thought to control miRNA activity [Etude and Hornstein, EMBO J. (2014) July 1; 33(13):1428-37], but the idea that cellular stress might broadly regulate miRNA biogenesis was not yet tested. This hypothesis was tested herein by measurement of the relative expression levels of mature miRNAs and their precursors, pre-miRNAs, which provides a proxy for the efficacy of Dicer complex activity. Induction of ER-stress in the hybrid motor neuron cell line NSC-34 by Thapsigargin (6.25 nM; 24 hrs) was sufficient to down-regulate mature miRNAs levels and to up-regulate miRNA precursors levels, relative to control, revealing inhibition of pre-miRNA processing (FIG. 7A), concomitant with up-regulation of RNA markers of ER-stress: ASNS, ATF4, CHOP and GRP78 (FIG. 7B). ER-stress affected miRNA biogenesis also in primary mouse motor neurons subjected to low doses of Thapsigargin (5 nM, 72 hrs; FIG. 7C), under conditions that up-regulated markers of ER-stress (FIG. 7D). Two other chemicals were tested that drive oxidative stress, namely Paraquat (PQ, 12 hrs, 1 mM) and sodium arsenite (1 hr, 0.5 mM). Induction of oxidative stress in NSC-34 cells caused up-regulation of pre-miRNA levels relative to control and down-regulation of mature miRNAs (FIGS. 7E-F). Therefore, several different cellular stress pathways negatively regulate miRNA biogenesis.

In order to characterize stress-related cascades that regulate miRNA biogenesis, mouse embryonic fibroblasts (MEFs) were utilized. Application of Thapsigargin (5 nM, 72 hrs) onto wild-type MEFs resulted in both accumulation of pre-miRNAs and relative depletion of the corresponding mature miRNA species (FIGS. 7G-H; light grey bars). Thus, the sensitivity of Dicer activity to cellular stress was not limited to NSC-34 cells or neurons. Differential cellular stress signaling cascades converge into the phosphorylation of serine-51 of translation initiation factor 2 alpha (eIF2a) [Hinnebusch et al. (2005) Nat Struct Mol Biol 12(10): 835-838]. To assess the impact of eIF2a signaling on miRNA biogenesis efficacy, MEFs were employed in which serine-51 was mutated into alanine as previously described [Costa-Mattioli et al. (2007) Cell 129(1): 195-206]. The present analysis demonstrated partial recovery from Thapsigargin-induced Dicer inhibition in cells harboring the S51A mutation (FIGS. 7G-H; black bars), which concomitantly failed to upregulate ATF4 mRNA levels (FIG. 7I). Therefore, phosphorylation of eIF2a controls, at least in part, miRNA biogenesis under stress. Treating NSC-34 cells with arsenite was sufficient to induce the phosphorylation of eIF2a (0.5 mM; 1 hr, FIG. 7J). In conclusion, cellular stress affects Dicer complex activity through phospho-eIF2a (Ser51) signaling.

Cytoplasmic SGs, the structural correlate of the stress response are observed in neurodegenerative specimen [Liu-Yesucevitz et al. (2010) PLoS One 5(10): e13250] and their assembly plays a role in the pathogenesis of ALS [Daigle et al. (2013) Hum Mol Genet 22(6): 1193-1205]. Next the hypothesis that SGs directly control the efficacy of miRNA biogenesis was assessed, by exposing MEFs to SG-inducer, Puromycin, which drives dismantling of translating polysomes. Puromycin (1 µg/ml, 24 hrs) decreased the efficacy of pre-miRNA biogenesis (FIG. 7L), suggesting that induction of SGs per se might impair Dicer complex activity.

Example 6

Expression of ALS-causing Genes Inhibits Pre-miRNA Processing

The assembly of SGs is facilitated by ALS-causing proteins TDP-43, FUS, hnRNPA2B1 and hnRNPA1 [[Kim et al. (2013) supra; Daigle et al. (2013) supra]. To assess the impact of ALS-causing mutants on miRNA biogenesis, next-generation sequencing of pre-miRNAs was utilized as previously taught [Newman et al. (2011), supra] as well as miRNAs in cells transfected with a truncated form of FUS R495X that leads to a relatively severe ALS clinical phenotype in humans. The study focused on pre-miRNA: mature miRNA couples that were expressed in NSC-34 above noise levels (more than 50 reads). Analysis of 63 couples revealed increased expression of the majority of pre-miRNA species and concomitant decrease in corresponding mature miRNAs (FIG. 8A). However, the expression levels of mRNAs encoding Ago2, Dicer, PACT and TRBP were unchanged in comparison to control transfected cells (FIG. 8B) and Dicer and Ago2 protein levels were comparable (FIG. 8C).

Example 7

Stress Granule Formation Controls miRNA Biogenesis

Next, it was tested if an inhibitor of SG formation can modulate the inhibition of miRNA biogenesis, imposed by ALS-causing mutants. FUS R495X was employed as well as two additional mutants that drive ALS in humans, namely, TDP-43 A315T and SOD1 G93A. This qPCR analysis of five representative pre-miRNA:miRNA pairs revealed that the expression of ALS-causing mutants inhibits miRNA biogenesis in NSC-34 cells (FIG. 9A). However, cycloheximide (CHX), an established inhibitor of SG formation, prevented the reduction in Dicer complex activity (FIG. 9A), supporting the view that SG formation was required for inhibition of miRNA biogenesis. Noteworthy, it is unlikely that the effect of CHX was due to a general inhibition of protein synthesis since Puromycin, which equally inhibits translation, had an opposite effect (FIG. 7L). Furthermore, CHX impact is consistent with its protective roles in cultured motor neurons [Yang et al. (2013) Cell Stem Cell 12(6):713-26].

To gain further mechanistic insight, targeted mass-spectrometry analysis was performed of Ago2 and Dicer protein interactions. This study examined a set of proteins that were shown to immunoprecipitate with either Ago2 or Dicer in a preliminary unbiased screen. Targeted mass-spectrometry revealed enhanced interactions of Ago2 with Dicer in cells that were treated with sodium arsenite, relative to basal conditions (FIGS. 9B-C). In line with the present observations, increased Ago2 binding to Dicer was previously shown to decrease its Dicer activity [Tahbaz et al. (2004) EMBO Rep 5(2): 189-194]. As Dicer complex composition impacts miRNA biogenesis, additional Ago2 and Dicer interactions were measured. HSP90 and co-chaperone p23 have a known role in regulating the interactions of Dicer with Ago2 [Pare et al. (2013) Mol Biol Cell 24(15): 2303-2310], consistent with the present measurements of increased interaction with Dicer under stress (FIG. 9C). These increased interactions may contribute to stabilization of an intermediate configuration of a Dicer-Ago2-P23-HSP90 complex and this way to inhibition of Dicer catalytic activity.

In addition, stress increased Ago2 and/or Dicer protein interactions with SG components (FIGS. 9B-C), eiF2S1, eIF3 and eIF5a, and with poly(rC) binding proteins PCBP1 (hnRNP E1) and PCBP2 (hnRNP E2) (FIGS. 9B-C). These PCBPs are iron chaperones that are found in stress granules and P-bodies. PCBP2 binds to miRNA precursors and presents them to Dicer for more efficient miRNA processing. Therefore, PCBPs binding to Ago2 and Dicer exposes more complex regulation of miRNA biogenesis under stress. Finally, Ago2 is phosphorylated on serine-378 under stress, consistent with more than 10 fold increase Ago2 phosphorylation on serine-387 in the present system (FIG. 9B). Taken together, these observations point towards substantial changes in the assembly of the Dicer/RISC loading complex and its interactions with endogenous co-factors that modify Dicer activity.

Next, the impact of FUS R495X expression in NSC-34 cells was examined by mass-spectrometry. It was revealed that FUS R495X increased the interaction of Ago2 with Dicer and eIF3L. Furthermore, blocking SGs formation by application of CHX, reduced mutant-induced interaction of Ago2 with Dicer and eIF3L (FIGS. 9D-E).

Also it was tested whether HSP90 activity is functionally involved in miRNA processing under stress, as previously suggested [Pare et al. (2009) Mol Biol Cell 20(14): 3273-3284]. To this end, cells were exposed to Thapsigargin-induced stress in the presence or absence of two different HSP90 inhibitors. Geldanamycin and 17-AAG both aggravated Thapsigargin-induced inhibition of miRNA biogenesis (FIG. 9F), emphasizing the involvement of HSP90 in Dicer complex activity.

Example 8

Enoxacin Ameliorates ALS-induced Defects in Pre-miRNA Processing

Because of the impairment in pre-miRNA processing, and because Ago2 and Dicer protein expression levels were unchanged, the hypothesis was that enhancing Dicing complex activity might reverse the negative effect of the ALS-causing mutant proteins on miRNAs. To address this experimentally, Enoxacin, a fluoroquinolone antibiotic commonly used for the treatment of urinary tract and airway infections, was employed. Enoxacin is known to increase pre-miRNA processing [Melo et al. (2011) Proc Natl Acad Sci USA 108(11): 4394-4399] via increasing the binding affinity of TRBP and pre-miRNAs, thereby increasing pre-miRNA processing.

Intriguingly, the impaired ratio of pre-miRNAs to miRNAs that was evident in NSC-34 cells upon transfection with vectors expressing ALS-causing FUS R495X (FIG. 10A), TDP-43 A315T (FIG. 10B) or SOD1 G93A (FIG. 10C) was ameliorated by applying Enoxacin (100 µM for 72 hrs) to transfected cultures. Because Enoxacin was able to reverse the miRNA biogenesis defect, these results further support the emerging view that Dicer catalytic activity is reduced in ALS.

Example 9 miRNAs are Down-regulated in the SOD1 G93A Mouse Model of ALS

Figures 11A, 11B:
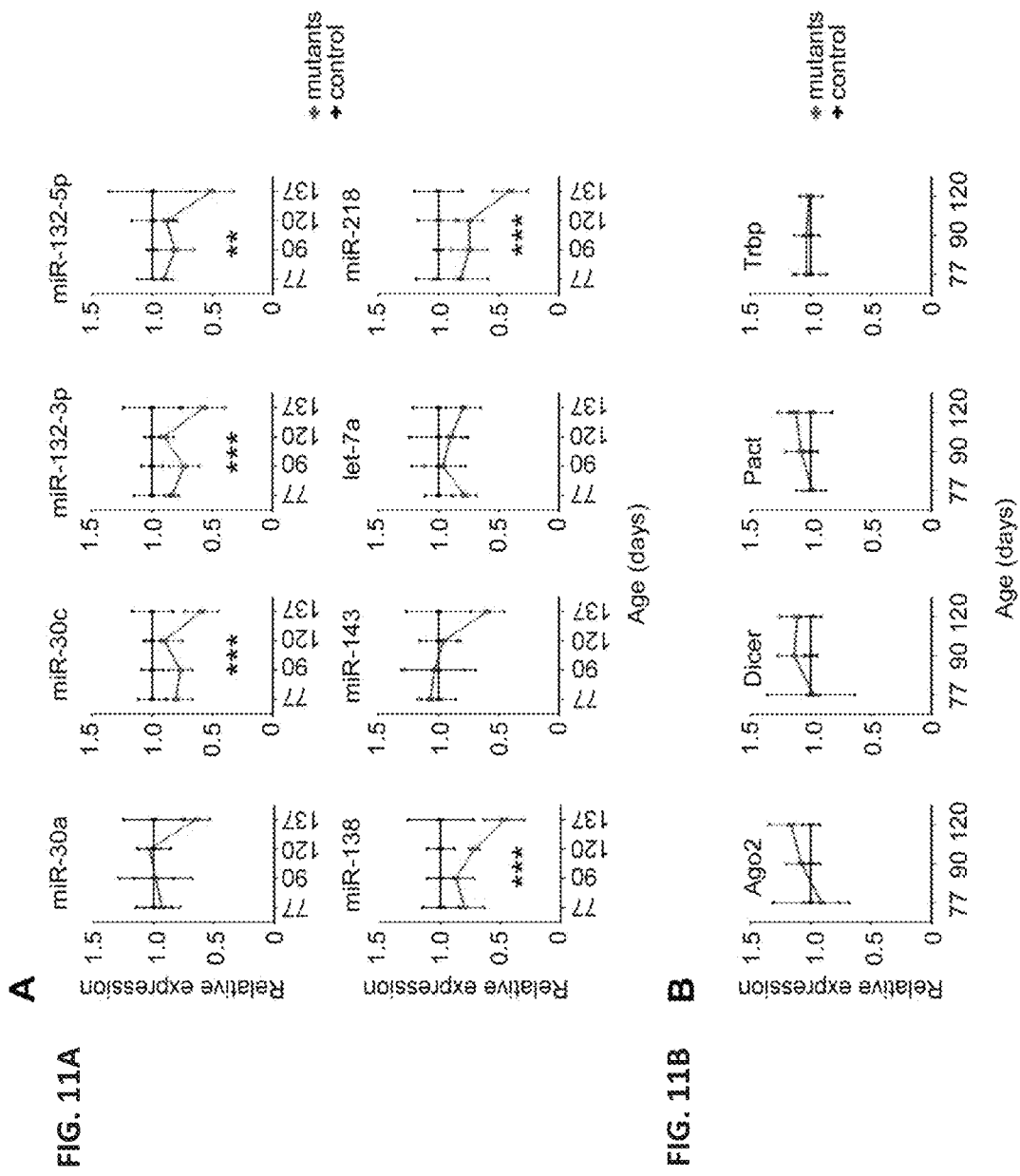
Figure 11D:
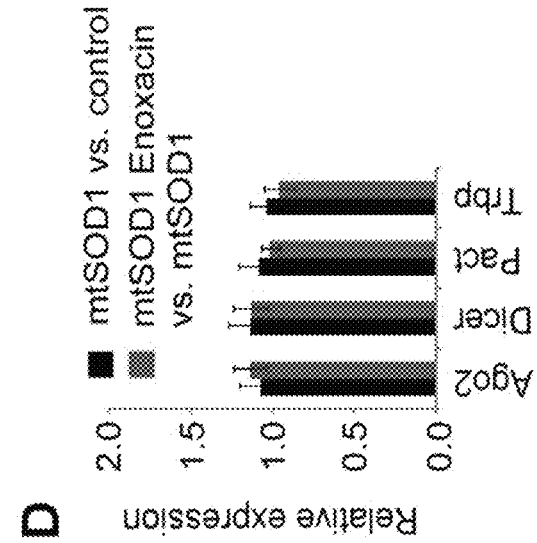
Figure 11C:
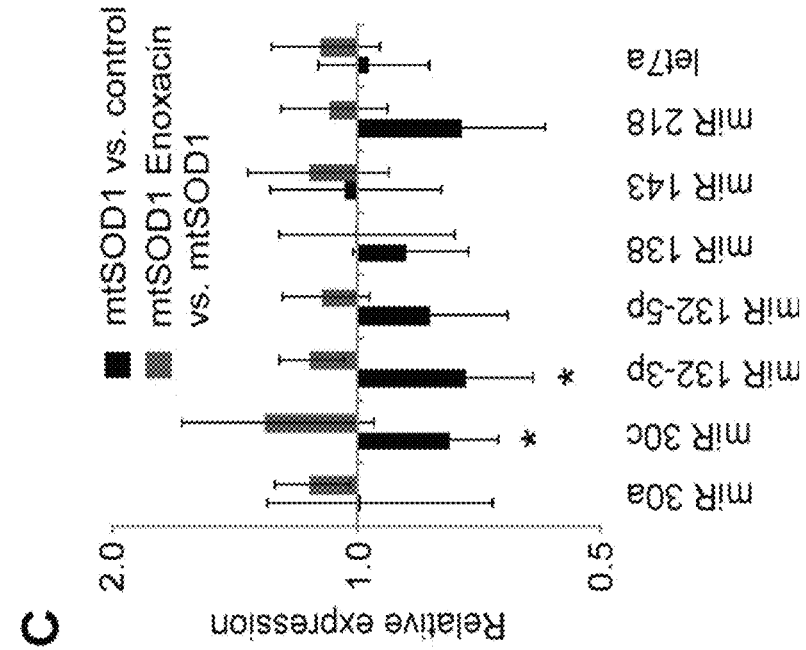

The experiments were then extended to the SOD1 G93A mouse model of ALS (B6SJL-Tg (SOD1*G93A)1Gur/J mouse strain previously described Gurney et al. [Gurney et al. (1994) supra]. miRNA levels were progressively down-regulated (FIG. 11A) and mRNA levels of Ago2, Dicer, PACT and TRBP remained unchanged (FIG. 11B). The tendency of miRNA down-regulation in the SOD1 G93A spinal cords is in accordance with mtSOD1 patient data and reminiscent of data from NSC-34 cells transfected with ALS-causing vectors. To potentially enhance Dicer complex activity also in vivo, SOD1 G93A mice were treated with Enoxacin and were assessed for miRNA levels. Oral application of Enoxacin or carrier (water) to two sibling-matched cohorts was started on day 42 of the mouse life. Spinal cords were harvested at day 90 after 48 days of treatment. The qPCR analysis revealed that the negative effect of the ALS-causing SOD1 G93A mutant on miRNAs was compensated by Enoxacin (FIG. 11C). Intriguingly, Enoxacin-dependent recovery of miRNA expression levels seemed to correlate with the differential impairment in Dicer activity, such that miRNA species that were more affected by ALS were more responsive to Enoxacin, without overt over-compensation. mRNA levels of Ago2, Dicer, PACT and TRBP remained unchanged (FIG. 11D).

Example 10

Enoxacin Therapy is Beneficial for Neuromuscular Function in SOD1 G93A Mouse Model of ALS Recently, Enoxacin was shown to increase the expression of miRNAs in the frontal cortex of rats with beneficial impact on depression. To test whether enhancing Dicer catalytic activity in vivo will be beneficial for ALS, SOD1 G93A mice were treated with Enoxacin and were assessed for their neuromuscular function as previously taught Gurney et al. [Gurney et al. (1994) supra]. Oral application of Enoxacin (n=40) or carrier (water, n=37) to two sibling-matched cohorts was started on day 42 of the mouse life. A delay of about 7 days was observed at the onset of neurological symptoms (FIG. 12A). Consistently, weight peak and onset of weight decline, which is defined by the loss of 1 gram body weight after the weight peak, were delayed in Enoxacin-treated mice (FIGS. 12B-C). Kaplan-Meier survival analysis yielded no significant differences between the two groups (FIG. 12D). However, evaluation of neurological status by employing a common scoring system [Gill et al. (2009), supra], revealed that the Enoxacin-treated cohort was superior to untreated controls (FIG. 12E).

To further evaluate motor function an automated quantitative gait analysis was performed using the CatWalk system [Neumann et al. (2009) J Neurosci Methods 176(1): 34-44]. Swing speed was significantly higher and stride length was significantly increased in the Enoxacin-treated group, relative to untreated controls (ten matched siblings per group, FIGS. 12F-G). Additionally, a significantly improved performance of the Enoxacin-treated group in comparison to untreated siblings was revealed in a Rotarod test (n=25 control, n=29 Enoxacin, FIG. 12H). Taken together, Enoxacin had a beneficial effect on multiple clinical parameters of the ALS SOD1 G93A mouse model. Rotarod testing revealed the beneficial impact of Enoxacin, at symptomatic age (day 120), even at a lower dose of Enoxacin (7 Enoxacin treated animals, 6 untreated controls, FIG. 12I). Furthermore, a significant improvement in gross strength, relative to controls, was observed by a hangwire assay (16 animals treated with Enoxacin, 15 untreated controls, FIG. 12J). Finally, a fully automated infra-red based homecage locomotion system was employed. Enoxacin-treated animals (n=6) moved significantly more than untreated controls (n=5) (FIG. 12K).

Although Enoxacin did not extend the lifespan of the SOD1 G93A model, an array of different assays revealed improved neuromuscular function, suggesting a beneficial profile. Noteworthy, Riluzole, the only FDA-approved drug for ALS, lacks survival benefit in SOD1G93A mice [Li et al. (2013) PLoS One 8(6): e65976]. Therefore, as previously suggested [Scott et al. (2008) Amyotroph Lateral Scler 9(1): 4-15], the predictive value of the aggressive SOD1 G93A model may be limited due to its 23 transgene copies in testing novel pharmacological interventions.

Example 11

Figure 13B:
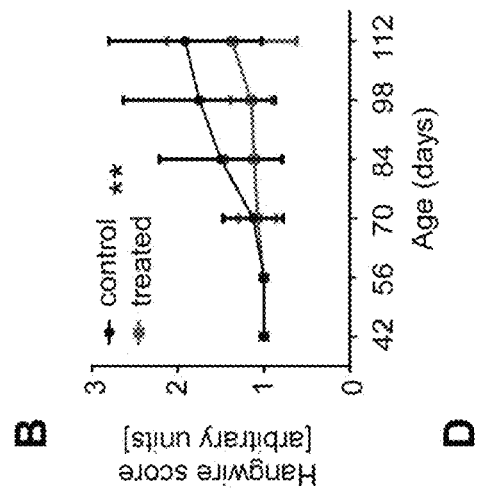
Figure 13D:
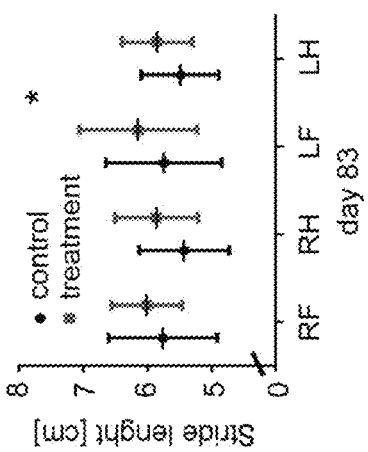
Figure 13A:
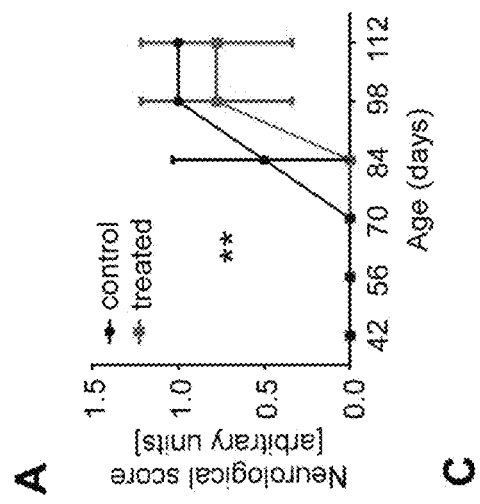
Figure 13C:
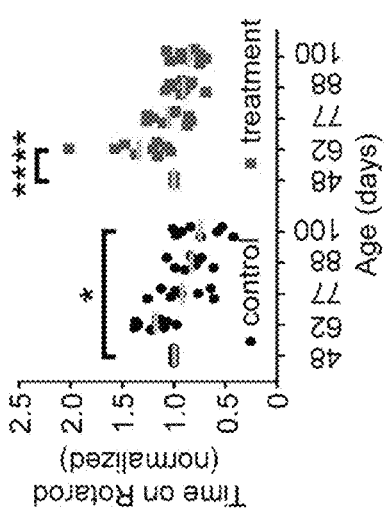

Enoxacin Therapy is Beneficial for Neuromuscular Function in TDP-43 A315T Mouse Model of ALS Based on the observations that pre-miRNA processing defect may be a common denominator of many forms of ALS, the molecular impact of Enoxacin was tested in an additional SOD1-independent ALS mouse, the TDP-43 A315T transgene previously described [Wegorzewska et al (2009) supra]. The neurological score of Enoxacin-treated female TDP-43 A315T mice was better than that of untreated controls (9 treated animals, 8 untreated controls; treatment started on day 42; FIG. 13A). Enoxacin treated group performed better than the untreated control group in the Rotarod test (FIG. 13C). Furthermore, average stride length was longer (FIG. 13D) and gross strength was improved (FIG. 13B) in the Enoxacin-treated group, relative to untreated controls. Of note, characterization of the TDP-43 A315T mice was performed until the onset of clinical gastro-intestinal pathology, which lead to early death of TDP-43 A315T mice and precluded the full development of ALS.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1 Sreedharan, J. et al., TDP-43 mutations in familial and sporadic amyotrophic lateral sclerosis. *Science* 319 (5870), 1668 (2008).

2 Kabashi, E. et al., TARDBP mutations in individuals with sporadic and familial amyotrophic lateral sclerosis. *Nat Genet* 40 (5), 572 (2008).

3 Bosco, D. A. et al., Mutant FUS proteins that cause amyotrophic lateral sclerosis incorporate into stress granules. *Hum Mol Genet* (2010).

4 Kwiatkowski, T. J., Jr. et al., Mutations in the FUS/TLS gene on chromosome 16 cause familial amyotrophic lateral sclerosis. *Science* 323 (5918), 1205 (2009); Vance, C. et al., Mutations in FUS, an RNA processing protein, cause familial amyotrophic lateral sclerosis type 6. *Science* 323 (5918), 1208 (2009).

5 Buratti, E. and Baralle, F. E., The multiple roles of TDP-43 in pre-mRNA processing and gene expression regulation. *RNA Biol* 7 (4) (2010); Kawahara, Y. and Mieda-Sato, A., TDP-43 promotes microRNA biogenesis as a component of the Drosha and Dicer complexes. *Proc Natl Acad Sci USA* 109 (9), 3347 (2012).

6 Lagier-Tourenne, C., Polymenidou, M., and Cleveland, D. W., TDP-43 and FUS/TLS: emerging roles in RNA processing and neurodegeneration. *Hum Mol Genet* 19 (R1), R46 (2010).

7 Haramati, S. et al., miRNA malfunction causes spinal motor neuron disease. *Proc Natl Acad Sci USA* 107 (29), 13111 (2010).

8 Abelson, J. F. et al., Sequence variants in SLITRK1 are associated with Tourette's syndrome. *Science* 310 (5746), 317 (2005); Rademakers, R. et al., Common variation in the miR-659 binding-site of GRN is a major risk factor for TDP43-positive frontotemporal dementia. *Hum Mol Genet* 17 (23), 3631 (2008); Georges, M., Coppieters, W., and Charlier, C., Polymorphic miRNA-mediated gene regulation: contribution to phenotypic variation and disease. *Curr Opin Genet Dev* 17 (3), 166 (2007); Chen, K. and Rajewsky, N., Natural selection on human microRNA binding sites inferred from SNP data. *Nat Genet* 38 (12), 1452 (2006).

9 Rabin, S. J. et al., Sporadic ALS has compartment-specific aberrant exon splicing and altered cell-matrix adhesion biology. *Hum Mol Genet* 19 (2), 313 (2010).

10 Pena, J. T. et al., miRNA in situ hybridization in formaldehyde and EDC-fixed tissues. *Nat Methods* 6 (2), 139 (2009).

11 Gregory, R. I. et al., The Microprocessor complex mediates the genesis of microRNAs. *Nature* 432 (7014), 235 (2004).

12 Shan, G. et al., A small molecule enhances RNA interference and promotes microRNA processing. *Nat Biotechnol* 26 (8), 933 (2008); Melo, S. et al., Small molecule enoxacin is a cancer-specific growth inhibitor that acts by enhancing TAR RNA-binding protein 2-mediated microRNA processing. *Proc Natl Acad Sci USA* 108 (11), 4394 (2011).

13 Brooks, B. R., Miller, R. G., Swash, M., and Munsat, T. L., El Escorial revisited: revised criteria for the diagnosis of amyotrophic lateral sclerosis. *Amyotroph Lateral Scler Other Motor Neuron Disord* 1 (5), 293 (2000).

Additional References (Cited in the Specification)

Chen, Y. Z., Bennett, C. L., Huynh, H. M., Blair, I. P., Puls, I., Irobi, J., Dierick, I., Abel, A., Kennerson, M. L., Rabin, B. A. et al. (2004) 'DNA/RNA helicase gene mutations in a form of juvenile amyotrophic lateral sclerosis (ALS4)', *Am J Hum Ge net* 74(6): 1128-35.

Chendrimada T P, Gregory R I, Kumaraswamy E, Norman J, Cooch N, Nishikura K, Shiekhattar R (2005) *TRBP recruits the Dicer complex to AGO2 for microRNA processing and gene silencing*. Nature 436: 740-744

Ge, W. W., Wen, W., Strong, W., Leystra-Lantz, C. and Strong, M. J. (2005) 'Mutant copper-zinc superoxide dismutase binds to and destabilizes human low molecular weight neurofilament mRNA', *J Biol Chem* 280(1): 118-24.

Greenway, M. J., Andersen, P. M., Russ, C., Ennis, S., Cashman, S., Donaghy, C., Patterson, V., Swingler, R., Kieran, D., Prehn, J. et al. (2006) 'ANG mutations segregate with familial and 'sporadic' amyotrophic lateral sclerosis', *Nat Genet* 38(4): 411-3.

Gregory R I, Chendrimada T P, Cooch N, Shiekhattar R (2005) *Human RISC couples microRNA biogenesis and posttranscriptional gene silencing*. Cell 123: 631-640

Kabashi, E., Valdmanis, P. N., Dion, P., Spiegelman, D., McConkey, B. J., Vande Velde, C., Bouchard, J. P., Lacomblez, L., Pochigaeva, K., Salachas, F. et al. (2008) 'TARDBP mutations in individuals with sporadic and familial amyotrophic lateral sclerosis', *Nat Genet* 40(5): 572-4.

Kwiatkowski, T. J., Jr., Bosco, D. A., Leclerc, A. L., Tamrazian, E., Vanderburg, C. R., Russ, C., Davis, A., Gilchrist, J., Kasarskis, E. J., Munsat, T. et al. (2009) 'Mutations in the FUS/TLS gene on chromosome 16 cause familial amyotrophic lateral sclerosis', *Science* 323 (5918): 1205-8.

Lagier-Tourenne, C. and Cleveland, D. W. (2009) 'Rethinking ALS: the FUS about TDP-43', *Cell* 136(6): 1001-4.

Lagier-Tourenne, C., Polymenidou, M. and Cleveland, D. W. (2010) 'TDP-43 and FUS/TLS: emerging roles in RNA processing and neurodegeneration', *Hum Mol Genet* 19(R1): R46-64.

Lemmens, R., Moore, M. J., Al-Chalabi, A., Brown, R. H., Jr. and Robberecht, W. (2010) 'RNA metabolism and the pathogenesis of motor neuron diseases', *Trends Neurosci* 33(5): 249-58.

Lu, L., Zheng, L., Viera, L., Suswam, E., Li, Y., Li, X., Estevez, A. G. and King, P. H. (2007) 'Mutant Cu/Zn-superoxide dismutase associated with amyotrophic lateral sclerosis destabilizes vascular endothelial growth factor mRNA and downregulates its expression', *J Neurosci* 27(30): 7929-38.

Sreedharan, J., Blair, I. P., Tripathi, V. B., Hu, X., Vance, C., Rogelj, B., Ackerley, S., Durnall, J. C., Williams, K. L., Buratti, E. et al. (2008) 'TDP-43 mutations in familial and sporadic amyotrophic lateral sclerosis', *Science* 319 (5870): 1668-72.

Strong, M. J. (2010) 'The evidence for altered RNA metabolism in amyotrophic lateral sclerosis (ALS)', *J Neurol Sci* 288(1-2): 1-12.

Vance, C., Rogelj, B., Hortobagyi, T., De Vos, K. J., Nishimura, A. L., Sreedharan, J., Hu, X., Smith, B., Ruddy, D., Wright, P. et al. (2009) 'Mutations in FUS, an RNA processing protein, cause familial amyotrophic lateral sclerosis type 6', *Science* 323(5918): 1208-11.

What is claimed is:

1. A method of treating Amyotrophic Lateral Sclerosis (ALS) in a subject in need thereof, the method comprising administering to the subject a therapeutically effective amount of enoxacin, thereby treating the ALS in the subject.

2. The method of claim 1, further comprising administering to the subject an anti-ALS agent.

* * * * *

SEQUENCE LISTING

<160> NUMBER OF SEQ ID NOS: 105

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
cctgtagaac cgaatttgtg                                              20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
tcgaatctgt gactatgtgg                                              20

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 3
gtaaacatcc tcgactggaa gct                                          23

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
gctgcaaaca tccgactgaa                                              20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
gtcttcgtgc tttcagcttc                                              20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
ttcttggttc tttcatagcc                                              20

<210> SEQ ID NO 7
<211> LENGTH: 21
<212> TYPE: DNA
<213> ORGANISM: Artificial sequence

```
<220> FEATURE:
<223> OTHER INFORMATION: Single strand DNA oligonucleotide

<400> SEQUENCE: 7
gatgacacgc aaattcgtga a                                              21

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
aataccgggt gctgtaggct t                                              21

<210> SEQ ID NO 9
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 9
gctgtactga cttgatgaaa gta                                            23

<210> SEQ ID NO 10
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 10
cttttggaac tgaatctaag tga                                            23

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11
taccctgtag aaccgaattt gtg                                            23

<210> SEQ ID NO 12
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 12
tgtaaacatc ctcgactgga ag                                             22

<210> SEQ ID NO 13
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 13
tgtaaacatc ctacactctc agc                                            23
```

```
<210> SEQ ID NO 14
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 14
agcagcattg tacagggcta tga                                              23

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
taacagtcta cagccatggt cg                                               22

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 16
aaccgtggct ttcgattgtt ac                                               22

<210> SEQ ID NO 17
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 17
agctggtgtt gtgaatcagg ccg                                              23

<210> SEQ ID NO 18
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 18
tgagatgaag cactgtagct c                                                21

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 19
ttgtgcttga tctaaccatg t                                                21

<210> SEQ ID NO 20
<211> LENGTH: 26
<212> TYPE: DNA
<213> ORGANISM: Artificial sequence
<220> FEATURE:
<223> OTHER INFORMATION: Single strand DNA oligonucleotide
```

```
<400> SEQUENCE: 20
acctggcata caatgtagat ttctgt                                      26

<210> SEQ ID NO 21
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 21
tgaggtagta ggttgtgtgg tt                                          22

<210> SEQ ID NO 22
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 22
tgaggtagta ggttgtatag tt                                          22

<210> SEQ ID NO 23
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 23
agaggtagta ggttgcatag tt                                          22

<210> SEQ ID NO 24
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 24
ctgccaagtt tagcccagcg ga                                          22

<210> SEQ ID NO 25
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 25
cctgtagctc cggccaacac c                                           21

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
agccggcccc gttcttgctt                                             20
```

```
<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
ctcccggtgg tgccgaagtc                                              20

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
agcgattcga ggggcgtcca                                              20

<210> SEQ ID NO 29
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 29
gcccaaactg aaggtcccgc tg                                           22

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
atgacttgcc gggtggagcg                                              20

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 31
cgggagctca cgccaatgga a                                            21

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
cgggtgtccc tttcctcttc                                              20

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide
```

-continued

<400> SEQUENCE: 33
tgaagagcgc catggcttag					20

<210> SEQ ID NO 34
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 34
acctgaggag agagtgttcc a					21

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
caaggtgaaa ggcagggact					20

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36 cctttatca gggggcctgg					20

<210> SEQ ID NO 37
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 37
acttgggcct ccttgagttg					20

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
ctattcctgc gtcggtgtgt					20

<210> SEQ ID NO 39
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 39
attccaagtg cgtccgatga					20

```
<210> SEQ ID NO 40
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 40
cacacccgcc accagttcg                                                 19

<210> SEQ ID NO 41
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 41
gacccattcc caccatcaca cc                                             22

<210> SEQ ID NO 42
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 42
tggcaaagtg gagattgttg cc                                             22

<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 43
aagatggtga tgggcttccc g                                              21

<210> SEQ ID NO 44
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 44
acagagcctc gcctttgccg                                                20

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
acccatgccc accatcacgc                                                20

<210> SEQ ID NO 46
<211> LENGTH: 23
<212> TYPE: DNA
<213> ORGANISM: Artificial sequence
<220> FEATURE:
<223> OTHER INFORMATION: Single strand DNA oligonucleotide
```

```
<400> SEQUENCE: 46
caaagtgctc atagtgcagg tag                                              23

<210> SEQ ID NO 47
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 47
gtaccaaagt gctcatagtg cag                                              23

<210> SEQ ID NO 48
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 48
gtactggaag tgcccatact actaca                                           26

<210> SEQ ID NO 49
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 49
tagcttatca gactgatgtt ga                                               22

<210> SEQ ID NO 50
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 50
gcttatcaga ctgatgttga ctg                                              23

<210> SEQ ID NO 51
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 51
cagcccatcg actggtg                                                     17

<210> SEQ ID NO 52
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 52
tgtaaacatc cttgactgga ag                                               22
```

<210> SEQ ID NO 53
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 53
gtaaacatcc tcgactggaa gct                                    23

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
gctgcaaaca tccgactgaa                                        20

<210> SEQ ID NO 55
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 55
tccctgagac cctttaacct gtga                                   24

<210> SEQ ID NO 56
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 56
agcctaaccc gtggattt                                          18

<210> SEQ ID NO 57
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 57
tccctgagac cctaacttgt ga                                     22

<210> SEQ ID NO 58
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 58
ctgacaagaa cgagcgggtt ggg                                    23

<210> SEQ ID NO 59
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 59
cgaaggcctg cttgtcccct g                                              21

<210> SEQ ID NO 60
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 60
gcttgggcat gctgtgattt tcca                                           24

<210> SEQ ID NO 61
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 61
aggggttgca aagcagggct                                                20

<210> SEQ ID NO 62
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 62
aaagacctcg ctcaccccgc                                                20

<210> SEQ ID NO 63
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 63
tccccaaact gtcttccggc cc                                             22

<210> SEQ ID NO 64
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 64
ttggtgctct gcaggagctg gt                                             22

<210> SEQ ID NO 65
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 65
gccgcattcc gctttgccaa t                                              21

```
<210> SEQ ID NO 66
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 66
gaacctgagg agagagtgtt ca                                              22

<210> SEQ ID NO 67
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 67
agtttacctg ctttcaggtg tg                                              22

<210> SEQ ID NO 68
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 68
cccgagaaca cggtctttga                                                 20

<210> SEQ ID NO 69
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 69
ttcaaccacc ttgaacggca                                                 20

<210> SEQ ID NO 70
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 70
aataccgggt gctgtaggct t                                               21

<210> SEQ ID NO 71
<211> LENGTH: 16
<212> TYPE: PRT
<213> ORGANISM: Artificial sequence
<220> FEATURE:
<223> OTHER INFORMATION: peptide sequence from mass spectrometry
<220> FEATURE:
<221> NAME/KEY: MISC_FEATURE
<222> LOCATION: (14)..(14)
<223> OTHER INFORMATION: Iodocarbamylated cystein

<400> SEQUENCE: 71

Ala Ile Thr Ile Ala Gly Val Pro Gln Ser Val Thr Glu Cys Val Lys
1               5                   10                  15
```

```
<210> SEQ ID NO 72
<211> LENGTH: 14
<212> TYPE: PRT
<213> ORGANISM: Artificial sequence
<220> FEATURE:
<223> OTHER INFORMATION: peptide sequence from mass spectrometry
<220> FEATURE:
<221> NAME/KEY: MISC_FEATURE
<222> LOCATION: (8)..(8)
<223> OTHER INFORMATION: Iodocarbamylated cystein

<400> SEQUENCE: 72

Leu Val Val Pro Ala Thr Gln Cys Gly Ser Leu Ile Gly Lys
1               5                   10

<210> SEQ ID NO 73
<211> LENGTH: 13
<212> TYPE: PRT
<213> ORGANISM: Artificial sequence
<220> FEATURE:
<223> OTHER INFORMATION: peptide sequence from mass spectrometry

<400> SEQUENCE: 73

Ile Ile Thr Leu Thr Gly Pro Thr Asn Ala Ile Phe Lys
1               5                   10

<210> SEQ ID NO 74
<211> LENGTH: 13
<212> TYPE: PRT
<213> ORGANISM: Artificial sequence
<220> FEATURE:
<223> OTHER INFORMATION: peptide sequence from mass spectrometry

<400> SEQUENCE: 74

Ile Ile Thr Leu Ala Gly Pro Thr Asn Ala Ile Phe Lys
1               5                   10

<210> SEQ ID NO 75
<211> LENGTH: 11
<212> TYPE: PRT
<213> ORGANISM: Artificial sequence
<220> FEATURE:
<223> OTHER INFORMATION: peptide sequence from mass spectrometry

<400> SEQUENCE: 75

Ile Ala Asn Pro Val Glu Gly Ser Thr Asp Arg
1               5                   10

<210> SEQ ID NO 76
<211> LENGTH: 20
<212> TYPE: PRT
<213> ORGANISM: Artificial sequence
<220> FEATURE:
<223> OTHER INFORMATION: peptide sequence from mass spectrometry

<400> SEQUENCE: 76

Glu Ser Thr Gly Ala Gln Val Gln Val Ala Gly Asp Met Leu Pro Asn
1               5                   10                  15

Ser Thr Glu Arg
            20

<210> SEQ ID NO 77
<211> LENGTH: 12
<212> TYPE: PRT
<213> ORGANISM: Artificial sequence
<220> FEATURE:
<223> OTHER INFORMATION: peptide sequence from mass spectrometry
```

<400> SEQUENCE: 77

Ser Thr Asp Ala Pro Ser Gln Ser Thr Gly Asp Arg
1               5                   10

<210> SEQ ID NO 78
<211> LENGTH: 19
<212> TYPE: PRT
<213> ORGANISM: Artificial sequence
<220> FEATURE:
<223> OTHER INFORMATION: peptide sequence from mass spectrometry

<400> SEQUENCE: 78

Met Asp Ile Asp Asp Gly Thr Ser Ala Trp Gly Asp Pro Asn Ser Tyr
1               5                   10                  15

Asn Tyr Lys

<210> SEQ ID NO 79
<211> LENGTH: 17
<212> TYPE: PRT
<213> ORGANISM: Artificial sequence
<220> FEATURE:
<223> OTHER INFORMATION: peptide sequence from mass spectrometry

<400> SEQUENCE: 79

Ser Met Gln Asp Gly Trp Gly Glu Ser Asp Gly Pro Val Thr Gly Ala
1               5                   10                  15

Arg

<210> SEQ ID NO 80
<211> LENGTH: 7
<212> TYPE: PRT
<213> ORGANISM: Artificial sequence
<220> FEATURE:
<223> OTHER INFORMATION: peptide sequence from mass spectrometry

<400> SEQUENCE: 80

Gly Tyr Ile Asp Leu Ser Lys
1               5

<210> SEQ ID NO 81
<211> LENGTH: 12
<212> TYPE: PRT
<213> ORGANISM: Artificial sequence
<220> FEATURE:
<223> OTHER INFORMATION: peptide sequence from mass spectrometry

<400> SEQUENCE: 81

Val Val Thr Asp Thr Asp Glu Thr Glu Leu Ala Arg
1               5                   10

<210> SEQ ID NO 82
<211> LENGTH: 10
<212> TYPE: PRT
<213> ORGANISM: Artificial sequence
<220> FEATURE:
<223> OTHER INFORMATION: peptide sequence from mass spectrometry

<400> SEQUENCE: 82

Gly Val Phe Asn Val Gln Met Glu Pro Lys
1               5                   10

<210> SEQ ID NO 83
<211> LENGTH: 12
<212> TYPE: PRT
<213> ORGANISM: Artificial sequence

```
<220> FEATURE:
<223> OTHER INFORMATION: peptide sequence from mass spectrometry

<400> SEQUENCE: 83

Val His Leu Val Gly Ile Asp Ile Phe Thr Gly Lys
1               5                   10

<210> SEQ ID NO 84
<211> LENGTH: 8
<212> TYPE: PRT
<213> ORGANISM: Artificial sequence
<220> FEATURE:
<223> OTHER INFORMATION: peptide sequence from mass spectrometry

<400> SEQUENCE: 84

Ile Val Glu Met Ser Thr Ser Lys
1               5

<210> SEQ ID NO 85
<211> LENGTH: 14
<212> TYPE: PRT
<213> ORGANISM: Artificial sequence
<220> FEATURE:
<223> OTHER INFORMATION: peptide sequence from mass spectrometry

<400> SEQUENCE: 85

Val Tyr Glu Ile Gln Asp Ile Tyr Glu Asn Ser Trp Thr Lys
1               5                   10

<210> SEQ ID NO 86
<211> LENGTH: 9
<212> TYPE: PRT
<213> ORGANISM: Artificial sequence
<220> FEATURE:
<223> OTHER INFORMATION: peptide sequence from mass spectrometry

<400> SEQUENCE: 86

Val Ser Ser Asp Val Ile Asp Gln Lys
1               5

<210> SEQ ID NO 87
<211> LENGTH: 16
<212> TYPE: PRT
<213> ORGANISM: Artificial sequence
<220> FEATURE:
<223> OTHER INFORMATION: peptide sequence from mass spectrometry

<400> SEQUENCE: 87

Val Phe Ser Asp Glu Val Gln Gln Gln Ala Gln Leu Ser Thr Ile Arg
1               5                   10                  15

<210> SEQ ID NO 88
<211> LENGTH: 10
<212> TYPE: PRT
<213> ORGANISM: Artificial sequence
<220> FEATURE:
<223> OTHER INFORMATION: peptide sequence from mass spectrometry

<400> SEQUENCE: 88

Ile Asp Ile Ile Pro Asn Pro Gln Glu Arg
1               5                   10

<210> SEQ ID NO 89
<211> LENGTH: 15
<212> TYPE: PRT
<213> ORGANISM: Artificial sequence
```

```
<220> FEATURE:
<223> OTHER INFORMATION: peptide sequence from mass spectrometry

<400> SEQUENCE: 89

Asn Pro Asp Asp Ile Thr Gln Glu Glu Tyr Gly Glu Phe Tyr Lys
1               5                   10                  15

<210> SEQ ID NO 90
<211> LENGTH: 12
<212> TYPE: PRT
<213> ORGANISM: Artificial sequence
<220> FEATURE:
<223> OTHER INFORMATION: peptide sequence from mass spectrometry

<400> SEQUENCE: 90

Glu Leu Ile Ser Asn Ala Ser Asp Ala Leu Asp Lys
1               5                   10

<210> SEQ ID NO 91
<211> LENGTH: 7
<212> TYPE: PRT
<213> ORGANISM: Artificial sequence
<220> FEATURE:
<223> OTHER INFORMATION: peptide sequence from mass spectrometry
<220> FEATURE:
<221> NAME/KEY: MISC_FEATURE
<222> LOCATION: (5)..(6)
<223> OTHER INFORMATION: Iodocarbamylated cysteins

<400> SEQUENCE: 91

Ser Ile Leu Cys Cys Leu Arg
1               5

<210> SEQ ID NO 92
<211> LENGTH: 12
<212> TYPE: PRT
<213> ORGANISM: Artificial sequence
<220> FEATURE:
<223> OTHER INFORMATION: peptide sequence from mass spectrometry

<400> SEQUENCE: 92

Leu Asn Trp Leu Ser Val Asp Phe Asn Asn Trp Lys
1               5                   10

<210> SEQ ID NO 93
<211> LENGTH: 8
<212> TYPE: PRT
<213> ORGANISM: Artificial sequence
<220> FEATURE:
<223> OTHER INFORMATION: peptide sequence from mass spectrometry

<400> SEQUENCE: 93

Asp Val Asn Val Asn Phe Glu Lys
1               5

<210> SEQ ID NO 94
<211> LENGTH: 14
<212> TYPE: PRT
<213> ORGANISM: Artificial sequence
<220> FEATURE:
<223> OTHER INFORMATION: peptide sequence from mass spectrometry

<400> SEQUENCE: 94

Ser Asn Ala Glu Thr Ala Thr Asp Leu Val Val Leu Asp Arg
1               5                   10
```

```
<210> SEQ ID NO 95
<211> LENGTH: 15
<212> TYPE: PRT
<213> ORGANISM: Artificial sequence
<220> FEATURE:
<223> OTHER INFORMATION: peptide sequence from mass spectrometry

<400> SEQUENCE: 95

Phe Tyr Val Ala Asp Val Tyr Thr Asp Leu Thr Pro Leu Ser Lys
1               5                   10                  15

<210> SEQ ID NO 96
<211> LENGTH: 20
<212> TYPE: PRT
<213> ORGANISM: Artificial sequence
<220> FEATURE:
<223> OTHER INFORMATION: peptide sequence from mass spectrometry

<400> SEQUENCE: 96

Glu Leu Pro Asp Gly Thr Phe Tyr Ser Thr Leu Tyr Leu Pro Ile Asn
1               5                   10                  15

Ser Pro Leu Arg
            20

<210> SEQ ID NO 97
<211> LENGTH: 8
<212> TYPE: PRT
<213> ORGANISM: Artificial sequence
<220> FEATURE:
<223> OTHER INFORMATION: peptide sequence from mass spectrometry

<400> SEQUENCE: 97

Thr Pro Val Tyr Asp Leu Leu Lys
1               5

<210> SEQ ID NO 98
<211> LENGTH: 19
<212> TYPE: PRT
<213> ORGANISM: Artificial sequence
<220> FEATURE:
<223> OTHER INFORMATION: peptide sequence from mass spectrometry

<400> SEQUENCE: 98

Asp Gly Asn Glu Val Glu Pro Asp Asp His Phe Ser Ile Gly Val
1               5                   10                  15

Gly Ser Arg

<210> SEQ ID NO 99
<211> LENGTH: 13
<212> TYPE: PRT
<213> ORGANISM: Artificial sequence
<220> FEATURE:
<223> OTHER INFORMATION: peptide sequence from mass spectrometry

<400> SEQUENCE: 99

Ser Asp Val Gln Ile His Val Pro Thr Phe Thr Phe Arg
1               5                   10

<210> SEQ ID NO 100
<211> LENGTH: 15
<212> TYPE: PRT
<213> ORGANISM: Artificial sequence
<220> FEATURE:
<223> OTHER INFORMATION: peptide sequence from mass spectrometry
```

```
<220> FEATURE:
<221> NAME/KEY: MISC_FEATURE
<222> LOCATION: (8)..(8)
<223> OTHER INFORMATION: Iodocarbamylated cystein

<400> SEQUENCE: 100

Val Thr Val Gly Asp Ile Thr Cys Thr Gly Glu Gly Thr Ser Lys
1               5                   10                  15

<210> SEQ ID NO 101
<211> LENGTH: 19
<212> TYPE: PRT
<213> ORGANISM: Artificial sequence
<220> FEATURE:
<223> OTHER INFORMATION: peptide sequence from mass spectrometry

<400> SEQUENCE: 101

Asn Gln Leu Asn Pro Ile Gly Ser Leu Gln Glu Leu Ala Ile His His
1               5                   10                  15

Gly Trp Arg

<210> SEQ ID NO 102
<211> LENGTH: 12
<212> TYPE: PRT
<213> ORGANISM: Artificial sequence
<220> FEATURE:
<223> OTHER INFORMATION: peptide sequence from mass spectrometry

<400> SEQUENCE: 102

Val Leu Gln Pro Pro Ser Ile Leu Tyr Gly Gly Arg
1               5                   10

<210> SEQ ID NO 103
<211> LENGTH: 17
<212> TYPE: PRT
<213> ORGANISM: Artificial sequence
<220> FEATURE:
<223> OTHER INFORMATION: peptide sequence from mass spectrometry

<400> SEQUENCE: 103

Ser Val Ser Ile Pro Ala Pro Ala Tyr Tyr Ala His Leu Val Ala Phe
1               5                   10                  15

Arg

<210> SEQ ID NO 104
<211> LENGTH: 11
<212> TYPE: PRT
<213> ORGANISM: Artificial sequence
<220> FEATURE:
<223> OTHER INFORMATION: peptide sequence from mass spectrometry

<400> SEQUENCE: 104

Ser Ala Ser Phe Asn Thr Asp Pro Tyr Val Arg
1               5                   10

<210> SEQ ID NO 105
<211> LENGTH: 11
<212> TYPE: PRT
<213> ORGANISM: Artificial sequence
<220> FEATURE:
<223> OTHER INFORMATION: peptide sequence from mass spectrometry
<220> FEATURE:
<221> NAME/KEY: MISC_FEATURE
<222> LOCATION: (3)..(3)
<223> OTHER INFORMATION: phosphorylated Serine
```

```
<400> SEQUENCE: 105

Ser Ala Ser Phe Asn Thr Asp Pro Tyr Val Arg
1               5                   10
```